(12) United States Patent
Corbett et al.

(10) Patent No.: US 6,353,111 B1
(45) Date of Patent: Mar. 5, 2002

(54) TRANS OLEFINIC GLUCOKINASE ACTIVATORS

(75) Inventors: Wendy Lea Corbett, Randolph; Ramakanth Sarabu, Cedar Grove; Achyutharao Sidduri, Livingston, all of NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/727,624

(22) Filed: Dec. 1, 2000

Related U.S. Application Data

(60) Provisional application No. 60/170,783, filed on Dec. 15, 1999.

(51) Int. Cl.[7] .............. C07D 277/44; C07C 271/00
(52) U.S. Cl. ................. 548/195; 560/24; 560/38; 562/443; 564/155
(58) Field of Search .............. 548/195; 560/24, 560/38; 562/443; 564/155

(56) References Cited

U.S. PATENT DOCUMENTS

| | | | |
|---|---|---|---|
| 5,113,013 A | 5/1992 | Powell et al. | 562/495 |
| 5,169,951 A | 12/1992 | Sutter et al. | 548/212 |

OTHER PUBLICATIONS

Chemical Abstract for JP 71–99504, 1971.
Baker et al., J. Org. Chem., 17, p. 164–176 (1952).
Clark et al., Tetrahedron Lett., vol. 30, pp. 2133–2136 (1989).
Chipkin et al., Joslin's Diabetes, Lea and Febiger, Philadelphia, PA (1994) (C.R. Khan and G. C. Wier, eds.).
Kau et al., J. of Labelled Compd Rad., vol. 22, pp.1045–1060 (1985).
Baleja, Synth. Comm., 14, pp. 215–218 (1984).
Knochel et al., Tetrahedron, vol. 49, pp. 29–48 (1993).
Liang et al., Biochem. J., 309, pp.167–173 (1995).
Meglasson et al., Amer. J. Physiol., 246, pp. E1–E13 (1984).
Katayama et al., Chem. Lett., pp. 2073–2076 (1991).
Lucas et al., Org. Synth. Coll., vol. II, pp. 351–352 (1943).
Bunnett et al., Org. Synth. Coll., vol. V, pp. 478–480 (1973).
Printz et al., Ann. Rev. Nutrition (Oslon, Bier and McCormick, eds.), vol. 13, pp. 463–496 (1993).
Ono et al., Chem. Lett., pp.1393–1394 (1988).
Grupe et al., Cell, vol. 83, pp. 69–78 (1995).
Colowick, The Enzymes, vol. 9 (P. Boyer, ed.) Academic Press, New York, pp. 1–48 (1973).
Beugelmans et al., Tetrahedron Lett., vol. 36, pp. 1279–1282 (1995).
Knochel et al., Chem Rev., vol. 93, pp. 2117–2188 (1993).
Oae et al., Bull. Chem. Soc. Jpn., vol. 53, pp. 2023–2026 (1980).
Suzuki et al., Bull. Chem. Soc. Jpn., vol. 53, pp. 1765–1766 (1980).
Singh et al., J. Chem. Res.–S, (6), pp. 204–205 (1985).
Novak et al., Synthesis, 7, pp. 597–598 (1983).
Wöhrle et al., Synthesis, pp. 194–196 (1993).
Soai et al., Synthesis, pp.48–49 (1987).
Glaser et al., New England J. Med., vol. 338, pp. 226–230 (1998).
Chen et al., J. Chem. Soc., Chem. Comm., pp. 1389–1391 (1993).
Clark et al., J. Chem. Soc. Chem. Commun., pp. 1409–1410 (1987).
Giam et al., J. Chem. Soc., Chem. Comm., pp. 756–757 (1980).
Eapen et al., J. Org. Chem., vol. 49, pp. 478–482 (1984).
Zhu et al., J. Org. Chem., vol. 60, pp. 6389–6396 (1995).
Ferre et al., FASEB J., vol. 10, pp. 1213–1218 (1996).
Reddy et al., Organometallics, 3, pp. 630–632 (1984).

*Primary Examiner*—Zinna Northington Davis
(74) *Attorney, Agent, or Firm*—George W. Johnston; Dennis P. Tramaloni; F. Aaron Dubberley

(57) ABSTRACT

2,3-Di-substituted trans olefinic N-heteroaromatic or urido propionamides with said substitution at the 2-position being a substituted phenyl group and at the 3-position being a cycloalkyl ring, said propionamides being glucokinase activators which increase insulin secretion in the treatment of type II diabetes.

75 Claims, No Drawings

TRANS OLEFINIC GLUCOKINASE ACTIVATORS

PRIORITY TO PROVISIONAL APPLICATION(s) UNDER 35 U.S.C. §119(e)

This application claims priority under 35 U.S.C. §119(e) of provisional application Ser. No. 60/170,783, filed Dec. 15, 1999.

BACKGROUND OF THE INVENTION

Glucokinase (GK) is one of four hexokinases that are found in mammals [Colowick, S. P., in *The Enzymes*, Vol. 9 (P. Boyer, ed.) Academic Press, New York, N.Y., pages 1–48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97–115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10–15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463–496, 1993]. These findings contributed over a decade ago to the hypothesis that GK functions as a glucose sensor in β-cells and hepatocytes (Meglasson, M. D. and Matschinsky, F. M. *Amer. J. Physiol.* 246, E1–E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69–78, 1995; Ferrie, T., Riu, E., Bosch, F. et al., *FASEB J.*, 10, 1213–1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167–173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226–230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

This invention provides a compound, comprising an amide of the formula:

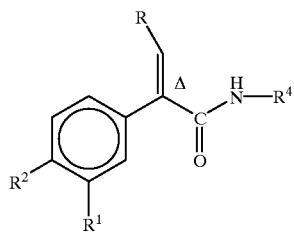

I wherein $R^1$ and $R^2$ are independently hydrogen, halo, amino, nitro, perfluoro-lower alkyl, lower alkyl thio, perfluoro-lower alkyl thio, lower alkyl sulfonyl, perfluoro-lower alkyl sulfonyl, lower alkyl sulfonyl methyl or lower alkyl sulfinyl;

R is —$(CH_2)_m$—$R_3$ or lower alkyl containing from 2 to 4 carbon atoms;

$R^3$ is cycloalkyl having from 3 to 8 carbon atoms;

$R^4$ is

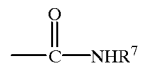

or an unsubstituted or a mono-substituted five- or six-membered heteroaromatic ring connected by a ring carbon atom to the amine group shown, which five- or six-membered heteroaromatic ring contains from 1 to 2 heteroatoms selected from the group consisting of sulfur, or nitrogen, with one heteroatom being nitrogen which is adjacent to the connecting ring carbon atom; said mono-substituted heteroaromatic ring being monosubstituted at a position on a ring carbon atom other than adjacent to said connecting carbon atom with a substituent selected from the group consisting of halo or

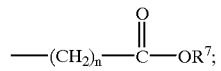

m is 0 or 1;

n is 0, 1, 2, 3 or 4;

$R^7$ is hydrogen or lower alkyl; and

Δ denotes a trans configuration across the double bond;

or a pharmaceutically acceptable salt thereof.

The compounds of formula I are glucokinase activators are useful for increasing insulin secretion in the treatment of type II diabetes.

DETAILED DESCRIPTION OF THE INVENTION

This invention provides a compound, comprising an amide of the formula:

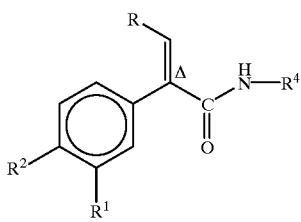

wherein $R^1$ and $R^2$ are independently hydrogen, halo, amino, nitro, perfluoro-lower alkyl, lower alkyl thio, perfluoro-lower alkyl thio, lower alkyl sulfinyl, lower alkyl sulfonyl, lower alkyl sulfonyl methyl or perfluoro-lower alkyl sulfonyl;

R is —$(CH_2)_m$—$R_3$ or lower alkyl containing from 2 to 4 carbon atoms;

$R^3$ is cycloalkyl having from 3 to 8 carbon atoms;

$R^4$ is

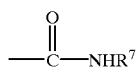

or an unsubstituted or a mono-substituted five- or six-membered heteroaromatic ring connected by a ring carbon atom to the amine group shown, which five- or six-membered heteroaromatic ring contains from 1 to 2 heteroatoms selected from the group consisting of sulfur or nitrogen, with one heteroatom being nitrogen which is adjacent to the connecting ring carbon atom; said mono-substituted heteroaromatic ring being monosubstituted at a position on a ring carbon atom other than adjacent to said connecting carbon atom with a substituent selected from the group consisting of halo or

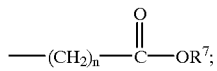

m is 0 or 1;

n is 0, 1, 2, 3 or 4;

$R^7$ is hydrogen or lower alkyl;

Δ denotes a trans configuration across the double bond; or a pharmaceutically acceptable salt thereof which are useful as glucokinase activators for increasing insulin secretion in the treatment of type II diabetes. In accordance with this invention, it has been found that the compounds of formula I having the trans configuration across the double bond have this glucokinase activity. On the other hand, the compounds of formula I which have a cis configuration across the double bond do not have this glucokinase activity.

When the term "cis" is utilized in this application, it designates that the two largest substituents attached across the double bond are on the same side of the double bond. The term "trans" as utilized in this application, designates that the largest substituents attached across the double bond are on opposite sides of the double bond and have the "E"-configuration.

As used throughout this application, the term "lower alkyl" includes both straight chain and branched chain alkyl groups having from 1 to 7 carbon atoms, such as methyl, ethyl, propyl, isopropyl, preferably methyl and ethyl, most preferably methyl. As used herein, the term "halogen or halo" unless otherwise stated, designates all four halogens, i.e. fluorine, chlorine, bromine and iodine. As used herein, "perfluoro-lower alkyl" means any lower alkyl group wherein all of the hydrogens of the lower alkyl group are substituted or replaced by fluoro. Among the preferred perfluoro-lower alkyl groups are trifluoromethyl, pentafluoroethyl, heptafluoropropyl, etc., most preferred is trifluoromethyl.

As used herein the term "aryl" signifies mononuclear aromatic hydrocarbon groups such as phenyl, tolyl, etc. which can be unsubstituted or substituted in one or more positions with halogen, nitro, lower alkyl, or lower alkoxy substituents and polynuclear aryl groups, such as naphthyl, anthryl, and phenanthryl, which can be unsubstituted or substituted with one or more of the aforementioned groups. Preferred aryl groups are the substituted and unsubstituted mononuclear aryl groups, particularly phenyl. As used herein, the term "lower alkoxy" includes both straight chain and branched chain alkoxy groups having from 1 to 7 carbon atoms, such as methoxy, ethoxy, propoxy, isopropoxy, preferably methoxy and ethoxy. The term "arylalkyl" denotes an alkyl group, preferably lower alkyl, in which one of the hydrogen atoms can be replaced by an aryl group. Examples of arylalkyl groups are benzyl, 2-phenylethyl, 3-phenylpropyl, 4-chlorobenzyl, 4-methoxybenzyl and the like.

As used herein, the term "lower alkanoic acid" denotes lower alkanoic acids containing from 2 to 7 carbon atoms such as propionic acid, acetic acid and the like. The term "lower alkanoyl" denotes monovalent alkanoyl groups having from 2 to 7 carbon atoms such as propionoyl, acetyl and the like. The term "aroic acids" denotes aryl alkanoic acids where aryl is as defined above and alkanoic contains from 1 to 6 carbon atoms. The term "aroyl" denotes aroic acids wherein aryl is as defined hereinbefore, with the hydrogen group of the COOH moiety removed. Among the preferred aroyl groups is benzoyl.

During the course of the reaction the various functional groups such as the free carboxylic acid or hydroxy groups will be protected via conventional hydrolyzable ester or ether protecting groups. As used herein the term "hydrolyzable ester or ether protecting groups" designates any ester or ether conventionally used for protecting carboxylic acids or alcohols which can be hydrolyzed to yield the respective hydroxyl or carboxyl group. Exemplary ester groups useful for those purposes are those in which the acyl moieties are derived from a lower alkanoic, aryl lower alkanoic, or lower alkane dicarboxcyclic acid. Among the activated acids which can be utilized to form such groups are acid anhydrides, acid halides, preferably acid chlorides or acid bromides derived from aryl or lower alkanoic acids. Example of anhydrides are anhydrides derived from monocarboxylic acid such as acetic anhydride, benzoic acid anhydride, and lower alkane dicarboxcyclic acid anhydrides, e.g. succinic anhydride as well as chloro formates e.g. trichloro, ethylchloro formate being preferred. A suitable ether protecting group for alcohols are, for example, the tetrahydropyranyl ethers such as 4-methoxy-5,6-dihydroxy-2H-pyranyl ethers. Others are aroylmethylethers such as benzyl, benzhydryl or trityl ethers or α-lower alkoxy lower alkyl ethers, for example, methoxymethyl or allylic ethers or alkyl silylethers such as trimethylsilylether.

The term "amino protecting group" designates any conventional amino protecting group which can be cleaved to yield the free amino group. The preferred protecting groups are the conventional amino protecting groups utilized in peptide synthesis. Especially preferred are those amino protecting groups which are cleavable under mildly acidic conditions from about pH 2.0 to 3. Particularly preferred amino protecting groups such as t-butoxycarbonyl carbamate, benzyloxycarbonyl carbamate, 9-flurorenylmethyl carbamate. The heteroaromatic ring defined by $R^4$ can be an unsubstituted or mono-substituted five- or six-membered heteroaromatic ring having from 1 to 2 heteroatoms selected from the group consisting of nitrogen, or sulfur and connected by a ring carbon to the amine of the amide group shown. The heteroaromatic ring contains a first nitrogen heteroatom adjacent to the connecting ring carbon atom and if present, the other heteroatoms can be sulfur, or nitrogen. Among the preferred heteroaromatic rings are pyridinyl, pyrimidinyl and thiazolyl; most preferred are pyridinyl and thiazolyl. These heteroaromatic rings which constitute $R^4$ are connected via a ring carbon atom to the amide group to form the amides of formula I. The ring carbon atom of the heteroaromatic ring which is connected via the amide linkage to form the compound of formula I cannot contain any substituent. When $R^4$ is an unsubstituted or mono-substituted five- or six-membered heteroaromatic ring, the preferred rings are those which contain a nitrogen heteroatom adjacent to the connecting ring carbon and a second heteroatom adjacent to the connecting ring carbon or adjacent to said first heteroatom.

The term "pharmaceutically acceptable salts" as used herein include any salt with both inorganic or organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, para-toluene sulfonic acid and the like. The term "pharmaceutically acceptable salts" also includes any pharmaceutically acceptable base salt such as amine salts, trialkyl amine salts and the like. Such salts can be formed quite readily by those skilled in the art using standard techniques.

The compound of formula I of this invention constitutes two preferred species, i.e., the compound of formula

I-A

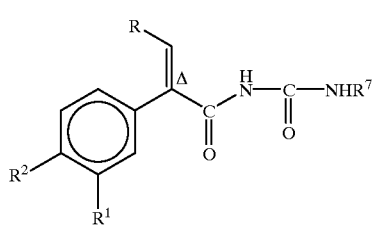

wherein Δ, R, $R^1$ and $R^2$ and $R^7$ are as above and the compound of the formula

I-B

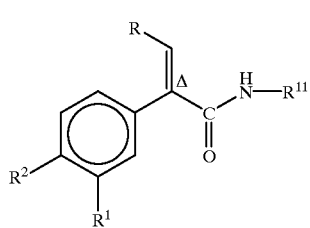

wherein R, $R^2$, $R^1$ and Δ are as above; and
$R^{11}$ is an unsubstituted or a mono-substituted five- or six-membered heteroaromatic ring connected by a ring carbon atom to the amine group shown, which five- or six-membered heteroaromatic ring contains from 1 to 2 heteroatoms selected from the group consisting of sulfur or nitrogen, with one heteroatom being nitrogen which is adjacent to the connecting ring carbon atom; said mono-substituted heteroaromatic ring being mono-substituted at a position on a ring carbon atom other than adjacent to said connecting carbon atom with a substituent selected from the group consisting of halo or

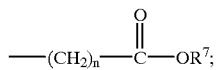

n is 0, 1, 2, 3 or 4; and
$R^7$ is hydrogen or lower alkyl.

In accordance with one embodiment of the compound of formula I-A, R can be a cycloalkyl group which contains from 3 to 8 carbon atoms, preferably cyclohexyl (compound I-A1). Among the various embodiments of the cyclohexyl amides of compound I-A1 are included, those compounds where one of $R^1$ and $R^2$ is hydrogen, halo, lower alkyl sulfonyl or perfluoro lower alkyl and the other of said $R^1$ and $R^2$ is halo, lower alkyl sulfonyl or perfluoro lower alkyl and particularly those compounds one of $R^1$ and $R^2$ is hydrogen or lower alkyl sulfonyl or perfluoro lower alkyl sulfonyl and the other is lower alkyl sulfonyl or perfluoro lower alkyl. Another embodiment of the compound of formula I-A are those compounds where R is a lower alkyl group containing from 2 to 4 carbon atoms (the compounds of formula I-A2). Among the embodiments of the compounds of formula I-A2 are those compounds where one of $R^1$ and $R^2$ is hydrogen, halo, lower alkyl sulfonyl or perfluoro lower alkyl and the other of said $R^1$ and $R^2$ is halo, lower alkyl sulfonyl or perfluoro lower alkyl.

An embodiment of the compound of formula I-B are those compounds where $R^{11}$ is an unsubstituted or mono-substituted thiazole ring. When $R^{11}$ is an unsubstituted thiazole ring, R can be a lower alkyl group containing from 2 to 4 carbon atoms. (compound I-B1) Among the embodiments of the compounds of the formula I-B1 are those compounds where one of $R^1$ or $R^2$ is hydrogen, lower alkyl sulfonyl, lower alkyl sulfonyl methyl, perfluoro lower alkyl, halo, nitro and the other of said $R^1$ or $R^2$ is lower alkyl sulfonyl, lower alkyl sulfonyl methyl, perfluoro lower alkyl, halo or nitro and preferably those compounds of formula IB-1 where one of $R^1$ and $R^2$ is hydrogen, lower alkyl sulfonyl and the other of said $R^1$ and $R^2$ is lower alkyl sulfonyl.

An embodiment of the compound of formula I-B are whose compounds where R is a cycloalkyl having from 3–8 carbon atoms (compound IB-2).

Among the embodiments of compounds of formula I-B2 are those compounds where the cycloalkyl group is cyclopentyl (IB-2a). The embodiment of compounds I-B2(a) are those compounds of formula IB-2(a) where $R^{11}$ is an unsubstituted thiazole ring (compounds IB-2a(1)). Among the embodiments of the compound IB-2a(1) are those compounds where one of said $R^1$ and $R^2$ is hydrogen, lower alkyl sulfonyl, lower alkyl sulfonyl methyl, perfluoro lower alkyl, halo or nitro and the other of said $R^1$ and $R^2$ is lower alkyl sulfonyl, lower alkyl sulfonyl methyl, perfluoro lower alkyl, halo or nitro and particularly preferred embodiments of the compounds IB-2(a)(1) are those compounds wherein:

a) one of $R^1$ or $R^2$ is lower alkyl sulfonyl and the other is hydrogen, nitro, lower alkyl sulfonyl, halo or perfluoro lower alkyl;

b) one of $R^1$ and $R^2$ is halo, hydrogen or perfluoro lower alkyl and the other is perfluoro lower alkyl or halogen; and c) one of $R^1$ and $R^2$ is lower alkyl sulfonyl methyl and the other is hydrogen, lower alkyl sulfonyl methyl or halogen.

Among the embodiments of compound of the formula IB-2a are those compounds where $R^{11}$ is a mono-substituted thiazolyl ring which includes compounds where $R^{11}$ is a halo substituted thiazole ring (compounds of the formula IB-2(a)(2)). Among the embodiments of the compounds of formula IB-2(a)(2) are those compounds where one of $R^1$ and $R^2$ is lower alkyl sulfonyl, hydrogen or halo and the other is lower alkyl sulfonyl or halo.

Another embodiment of compounds IB-2 are those compounds where R is cyclohexyl (compounds IB-2(b)). Among the embodiments of compounds IB-2(b) are those compounds where $R^1$ is an unsubstituted thiazolyl ring (compound IB-2(b)(1). Among the preferred compounds of IB-2(b) are those compounds where one of $R^1$ or $R^2$ is hydrogen, lower alkyl sulfonyl, lower alkyl sulfonyl methyl, perfluoro lower alkyl, halo, nitro and the other is lower alkyl sulfonyl, lower alkyl sulfonyl methyl, perfluoro lower alkyl, halo or nitro and particularly (a) where one of $R^1$ or $R^2$ is lower alkyl sulfonyl and the other is hydrogen, nitro, lower alkyl sulfonyl, halo or perfluoro lower alkyl;

(b) where one of $R^1$ and $R^2$ is halo, hydrogen or perfluoro lower alkyl and the other is perfluoro lower alkyl or halogen; and (c) where one of $R^1$ and $R^2$ is lower alkyl sulfonyl methyl and the other is hydrogen, lower alkyl sulfonyl methyl or halogen.

Another embodiment of the compound IB-2(b) are those compounds where $R^{11}$ is a mono-substituted thiazolyl ring and particularly a halo substituted ring (compound IB-2(b)(2)). Among the embodiments of compounds IB-2(b)(2) are those compounds where one or $R^1$ and $R^2$ is lower alkyl sulfonyl and the other is halogen, perfluoro lower alkyl or hydrogen.

Another embodiment of the compound IB-2 are those compounds where R is cycloheptyl (compound IB-2(d)) or cyclooctyl (compound IB-2(e)). An embodiment of the compounds (compound IB-2(d) and compound IB-2(e)) are those compounds where $R^{11}$ is unsubstituted thiazolyl (compounds IB-2(d)(1) and IB-2(e)(1)) respectively. In this case, the compounds of IB-2(d)(1) and IB-2(e)(1) that are preferred are those compounds where one of $R^1$ and $R^2$ is lower alkyl, sulfonyl, hydrogen, halogen or perfluoro lower alkyl and the other is lower alkyl sulfonyl, halogen or perfluoro lower alkyl.

Another embodiment of the compound IB-2(d) and compound IB-2(e) are those compounds where $R^{11}$ is a mono-substituted thiazolyl ring and the substitution is a halo group. In these cases, one of $R^1$ and $R^2$ can be hydrogen, lower alkyl sulfonyl, perfluoro lower alkyl or halogen and the other can be halogen, lower alkyl sulfonyl or perfluoro lower alkyl. In the compound IB-2(d) and IB-2(e), $R^{11}$ is a monosubstituted thiazolyl, the substitution can be

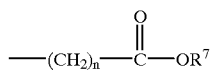

where n and $R^7$ are as above.

In this case, these compounds are one of $R^1$ and $R^2$ in these compounds can be lower alkyl sulfonyl and the other of said $R^1$ and $R^2$ is lower alkyl sulfonyl or hydrogen.

Another class of compounds of formula IB are those compounds where R is —$CH_2$—$R^3$ and $R^3$ is as above. Among the compounds included within this embodiment are compounds where R is a —$CH_2$-cyclohexyl group (compound IB-3). Included among compounds IB-3 are compounds where $R^{11}$ is a substituted or unsubstituted thiazolyl ring and particularly those compounds where $R^{11}$ is an unsubstituted thiazolyl ring and where the substitution on the thiazolyl ring is:

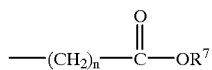

wherein n and $R^7$ are as above.

In this case compounds where one of $R^1$ and $R^2$ is lower alkyl sulfonyl and the other is lower alkyl sulfonyl or hydrogen are preferred.

In accordance with embodiment of the compound of formula IB, R can be cyclopentyl. An embodiment of this class includes compounds where $R^{11}$ is unsubstituted or mono-substituted pyridinyl ring. A preferred embodiment of this class is those compounds where one of $R^1$ and $R^2$ is hydrogen, lower alkyl sulfonyl or halogen and the other of said $R^1$ and $R^2$ is lower alkyl sulfonyl or halogen.

In accordance with this invention, the compounds of formula IA and IB can be prepared from the following compounds of the formula:

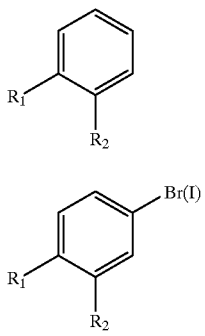

wherein $R^1$ and $R^2$ are as above.

In accordance with this invention, the compounds of formula IA and IB are prepared from the compounds of formula V via the following reaction scheme:

Scheme 1

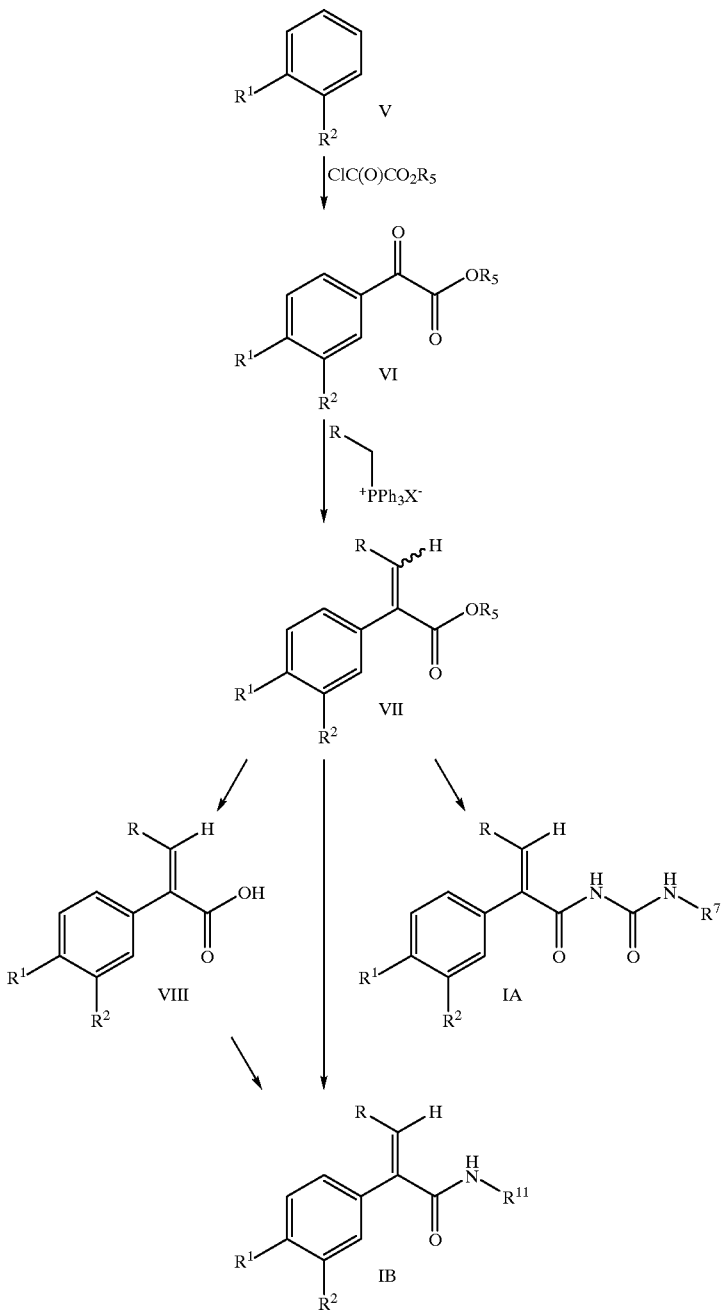

wherein R, $R^1$, $R^2$, $R^7$ and $R^{11}$ are as above;

R5 taken together with its attached oxygen atom forms a hydrolyzable acid protecting group and X is halogen.

The compound of formula V or XIX wherein one of $R^1$ and $R^2$ is nitro, thio, amino, halo, and the other is hydrogen are known materials. The amino substituted compounds of formula V or XIX can be converted to other substituents either before or after conversion to the compounds of formula IA or IB. In this respect, the amino groups can be diazotized to yield the corresponding diazonium compound, which in situ can be reacted with the desired lower alkyl thiol, perfluoro-lower alkyl thiol (see for example, Baleja, J. D. *Synth. Comm.* 1984, 14, 215; Giam, C. S.; Kikukawa, K., *J. Chem. Soc, Chem. Comm.* 1980, 756; Kau, D.; Krushniski, J. H.; Robertson, D. W, *J. Labelled Compd Rad.* 1985, 22, 1045; Oade, S.; Shinhama, K.; Kim, Y. H., *Bull Chem Soc. Jpn.* 1980, 53, 2023; Baker, B. R.; et al, *J. Org. Chem.* 1952, 17, 164) to yield corresponding compounds of formula V or XIX, where one of the substituents is lower alkyl thio, perfluoro-lower alkyl thio and the other is hydrogen. If desired, the lower alkyl thio or perfluoro-lower alkyl thio compounds can then be converted to the corresponding lower alkyl sulfonyl or perfluoro-lower alkyl sulfonyl substituted compounds of formula V or XIX by oxidation. Any conventional method of oxidizing alkyl thio substituents to sulfones can be utilized to effect this conversion. If it is desired to produce compounds of perfluoro-lower alkyl groups of compounds of formula V or XIX, the corresponding halo substituted compounds of formula V or XIX can be used as starting materials. Any conventional method of converting an aromatic halo group to the corresponding perfluoro lower alkyl group (see for example, Katayama, T.; Umeno, M., *Chem. Lett.* 1991, 2073; Reddy, G. S.; Tam., *Organometallics*, 1984, 3, 630; Novak, J.; Salemink, C. A., *Synthesis*, 1983, 7, 597; Eapen, K. C.; Dua, S. S.; Tamboroski, C., *J. Org. Chem.* 1984, 49, 478; Chen, Q, -Y.; Duan, J. -X. *J. Chem. Soc. Chem. Comm.* 1993, 1389; Clark, J. H.; McClinton, M. A.; Jone, C. W.; Landon, P.; Bisohp, D.; Blade, R. J., *Tetrahedron Lett.* 1989, 2133; Powell, R. L.; Heaton, C. A, U.S. Pat. No. 5,113,013) can be utilized to effect this conversion.

The compounds of formula V or XIX where both $R^1$ and $R^2$ substituents are amino can be obtained from the corresponding dinitro compound of formula V or XIX. Any conventional method of reducing a nitro group to an amine can be utilized to effect this conversion. The compound of formula V or XIX where both $R^1$ and $R^2$ are amine groups can be used to prepare the corresponding compound of formula V or XIX where both $R^1$ and $R^2$ are iodine or bromine via a diazotization reaction. Any conventional method of converting amino group to an iodo or bromo group (see for example, Lucas, H. J.; Kennedy, E. R. *Org. Synth. Coll. Vol, II* 1943, 351) can be utilized to effect this conversion. If it is desired to produce compounds of formula V or XIX, where both $R^1$ and $R^2$ are lower alkyl thio or perfluoro-lower alkyl thio groups, the compound of formula V or XIX where $R^1$ and $R^2$ are amino can be used as starting material. Any conventional method of converting aryl amino group to aryl thioalkyl group can be utilized to effect this conversion. If it is desired to produce compound of formula V or XIX where $R^1$ and $R^2$ are lower alkyl sulfonyl or lower perfluoro alkyl sulfonyl, the corresponding compounds of formula V or XIX where $R^1$ and $R^2$ are lower alkyl thio or perfluoro-lower alkyl thio can be used as starting material. Any conventional method of oxidizing alkyl thio substituents to sulfones can be utilized to effect this conversion. If it is desired to produce compounds of formula V or XIX, where both $R^1$ and $R^2$ are substituted with perfluoro-lower alkyl groups, the corresponding halo substituted compounds of formula V or XIX can be used as starting materials. Any conventional method of converting an aromatic halo group to the corresponding perfluoro-lower alkyl group can be utilized to effect this conversion.

The compounds of formula V or XIX where one of $R^1$ and $R^2$ is nitro and the other is halo are known from the literature (see for 4-chloro-3-nitrophenyl acetic acid, Tadayuki, S.; Hiroki, M.; Shinji, U.; Mitsuhiro, S. Japanese patent, JP 71–99504, *Chemical Abstracts* 80:59716; see for 4-nitro-3-chlorophenyl acetic acid, Zhu, J.; Beugelmans, R.; Bourdet, S.; Chastanet, J.; Rousssi, G. *J. Org. Chem.* 1995, 60, 6389; Beugelmans, R.; Bourdet, S.; Zhu, J. *Tetrahedron Lett.* 1995, 36, 1279). Thus, if it is desired to produce the compound of formula V or XIX where one of $R^1$ and $R^2$ is nitro and the other is lower alkyl thio or perfluoro-lower alkyl thio, the corresponding compound where one of $R^1$ and $R^2$ is nitro and the other is chloro can be used as starting material. In this reaction, any conventional method of nucleophilic displacement of aromatic chlorine group with a lower alkyl thiol can be used (see for example, Singh, P.; Batra, M. S.; Singh, H, *J. Chem. Res.-S* 1985 (6), S204; Ono, M.; Nakamura, Y.; Sata, S.; Itoh, I, *Chem. Lett*, 1988, 1393; Wohrle, D.; Eskes, M.; Shigehara, K.; Yamada, A, *Synthesis*, 1993, 194; Sutter, M.; Kunz, W, U.S. Pat. No. , U.S. Pat. No. 5,169,951). Once the compounds of formula V or XIX where one of $R^1$ and $R^2$ is nitro and the other is lower alkyl thio or perfluoro-lower alkyl thio are available, they can be converted to the corresponding compounds of formula V or XIX where one of $R^1$ and $R^2$ is nitro and the other is lower alkyl sulfonyl or perfluoro-lower alkyl sulfonyl using conventional oxidation procedures. If it is desired to produce compounds of formula V or XIX where one of $R^1$ and $R^2$ is amino and the other is lower alkyl thio or perfluoro-lower alkyl thio, the corresponding compound where one of $R^1$ and $R^2$ is nitro and the other is lower alkyl thio or perfluoro-lower alkyl thio can be used as starting materials. Any conventional method of reducing an aromatic nitro group to an amine can be utilized to effect this conversion. If it is desired to produce compounds of formula V or XIX where one of $R^1$ and $R^2$ is lower alkyl thio and the other is perfluoro-lower alkyl thio, the corresponding compound where one of $R^1$ and $R^2$ is amino and the other is lower alkyl thio or perfluoro-lower alkyl thio can be used as starting materials. Any conventional method of diazotizing aromatic amino group and reacting it in situ with the desired lower alkyl thio can be utilized to effect this conversion. If it is desired to produce compounds of formula V or XIX where one of $R^1$ and $R^2$ is lower alkyl sulfonyl and the other is periluoro-lower alkyl sulfonyl, the corresponding compounds where one of $R^1$ and $R^2$ is lower alkyl thio and the other is perfluoro-lower alkyl thio, can be used as starting materials. Any conventional method of oxidizing an aromatic thio ether group to the corresponding sulfone group can be utilized to effect this conversion. If it is desired to produce compounds of formula V or XIX where one of $R^1$ and $R^2$ is halo and the other is lower alkyl thio or perfluoro-lower alkyl thio, the corresponding compounds where one of $R^1$ and $R^2$ is amino and the other is lower alkyl thio or perfluoro-lower alkyl thio can be used as starting materials. Any conventional method of diazotizing an aromatic amino group and conversion of it in situ to an aromatic halide can be utilized to effect this conversion. If it is desired to produce compounds of formula V or XIX where one of $R^1$ and $R^2$ is halo and the other is lower alkyl sulfonyl or perfluoro-lower alkyl sulfonyl, the corresponding compounds where one of $R^1$ and $R^2$ is halo and the other is lower alkyl thio or perfluoro-lower alkyl thio can be used as starting materials. Any conventional method of oxidizing an aromatic thio ether to the corresponding sulfone can be utilized to effect this conversion. If one wishes to prepare the compound formula V or XIX where one of $R^1$ and $R^2$ is nitro and the other is amino, the compound of formula V or XIX where one of $R^1$ and $R^2$ is nitro and other is chloro can be used as a starting material. The chloro substituent on the phenyl ring can be converted to an iodo substituent (see for example, Bunnett, J. F.; Conner, R. M.; *Org. Synth. Coll Vol V*, 1973, 478; Clark, J. H.; Jones, C. W. *J. Cheni. Soc. Chemn. Comrnnun.* 1987, 1409), which in turn can be reacted with an azide transferring agent to form the corresponding azide (see for example, Suzuki, H.; Miyoshi, K.; Shinoda, *M. Bull. Cheni. Soc. Jpn*, 1980, 53, 1765). This azide can then be reduced in a conventional manner to form the amine substituent by reducing it with commonly used reducing agent for converting azides to amines (see for example, Soai, K.; Yokoyama, S.; Ookawa, A. Synthesis, 1987, 48).

To produce a compound where $R^1$ and/or $R^2$ are lower alkyl sulfonyl methyl in the compound of formula I, one can start with the known compound of formula V where one or both $R^1$ and $R^2$ are methyl. The methyl groups in these compounds can be brominated by any conventional means for brominating the methyl groups on phenyl rings. This brominated compound is then treated with the sodium salt of a lower alkyl thiol (such as sodium thiomethoxide) to form the lower alkyl thio methyl compound. To produce the lower alkyl sulfonyl methyl substituent, any conventional method of oxidizing lower alkyl thio substituents to sulfones, such as described above, can be utilized to effect this conversion.

The substituents which form $R^1$ and $R^2$ can be added to the ring after forination of the compounds of formulas IA and IB. Hence, all of the reactions described to produce various sustituents of $R^1$ and $R^2$ in the compound of formula I can be carried out on the compounds of formulas IA and IB after their formation.

The compounds of formula IA and IB are prepared from the compound of formulae V or XIX as set forth in Schemes 1 or 2. In the first step of this reaction in Scheme 1, the compound of formula V is reacted with oxalyl chloride wherein the free hydrolyzable organic acid group of the oxalyl chloride is protected by any conventional acid protecting groups. Among the preferred acid protecting groups are hydrolyzable esters of oxalyl chloride. The protecting group is formed by $R^5$. The reaction of the protected oxalyl chloride with the compound of formula V to produce the compound of formula VI is carried out via a Friedel-Crafts reaction. In carrying out this reaction, any of the conditions conventional in carrying out a Friedel-Crafts reaction can be utilized. In this reaction, $R^1$ and $R^2$ cannot be a nitro group. On the other hand, $R^1$ and $R^2$ can be an amino group. However, this amino group must be protected with a conventional hydrolyzable amino protecting group prior to carrying out the reaction. At some later stage in the reaction, these amino groups can be removed and the amino groups converted to nitro groups as described hereinbefore.

The compound of formula VI can be reacted with a triphenylphosphonium halide salt of formula IX via a Wittig reaction to produce the compound of formula VII. In carrying out this reaction any of the conditions conventional in carrying out a Wittig reaction can be utilized to effect these synthesis of the compound of formula VI with the compound of formula IX to produce the compound of formula VII. The compound of formula VII is formed as a mixture of cis and trans isomers about the double bond formed through the Wittig reaction. The mixture of cis and trans isomers of the compound of formula VII is directly hydrolyzed to the compound of formula VIII. In this hydrolysis reaction, the compound of formula VIII is produced as predominantly the trans isomer in this mixture. In addition, the trans isomer produced by this hydrolysis reaction is formed as a solid whereas the cis isomer is formed as an oily material. In view of this, it is very easy to separate the trans isomer by conventional methods of crystallization from this mixture to produce the compound of formula VIII as the pure trans isomer substantially free of the corresponding cis isomer. This crystallization can take place at this stage or at later stages of the reaction in the formation of the compounds of formula IA or IB. Therefore, by this procedure, the compound of formula IA and IB can be produced in pure trans form substantially free of the corresponding cis isomer.

In isolating the trans isomer, purification is best accomplished by hydrolyzing the protecting group —$OR^5$ to the corresponding free acid the compound of formula VIII and recovering this free acid via crystallization in the form of the trans isomer free of the corresponding cis isomer. In producing the compound of formula IB in its trans form, it is preferred to carry out the crystallization procedure with this compound of formula VIII. On the other hand, purification by crystallization can be carried out utilizing the compounds of formula IB and IA. Since the trans isomer of these compounds are solid and the cis isomer are oily material, any conventional method of crystallization can be used to effect this purification.

In the next step of this process, the compound of formula VIII is coupled to a compound of formula:

    XIV wherein $R^{11}$ is as above to produce the compound of formula IB. This coupling reaction can be carried out utilizing any of the conventional means by coupling an acid with a primary amino to produce an amide. On the other hand, the compound of formula VII can be directly coupled to the compound of formula XIV to produce the compound of formula IB without any intermediate hydrolysis steps.

In producing the compound of formula IA, the compound of formula VII is coupled with

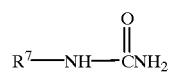    XV

This reaction can be carried out by converting the compound of formula VII to the corresponding free acid by removing the protecting group $R^5$ to form the carboxylic acid. The carboxylic acid of formula VIII can be converted to the corresponding amide by converting the acid to the acid chloride and thereafter reacting this acid chloride with ammonia. Conditions which are conventional for converting an acid to an acid chloride can be utilized in this procedure. This acid chloride is then reacted with an alkyl isocyanate of formula XV to form the urea adduct of formula IA. Any conventional method of reacting an alkyl isocyanate with an amide to form a urea linkage utilize the compound of formula IA.

The compound of formula IA can be formed as a mixture of cis and trans provided the compound of formula VII has not been purified. If desired, purification can take place with respect to the compound of formula IA to produce the compound of formula IA as the all-trans isomer free of the cis isomer. In the same maimer as the compound of formula IB or the compound of formula VIII can be purified, the compound of formula IA can be purified to produce this all trans isomer.

In accordance with another embodiment of this invention, the compound of formula VII can also be produced by the following reaction scheme. The reaction scheme 2 is applicable for producing compounds of formula IA or IB where one or both $R^1$ and $R^2$ is nitro. The coupling reaction can be easily carried out with any of the designated $R^1$ and $R^2$ groups, particularly those where $R^1$ and $R^2$ is nitro.

Scheme 2

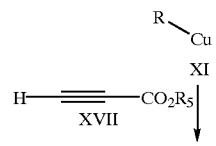

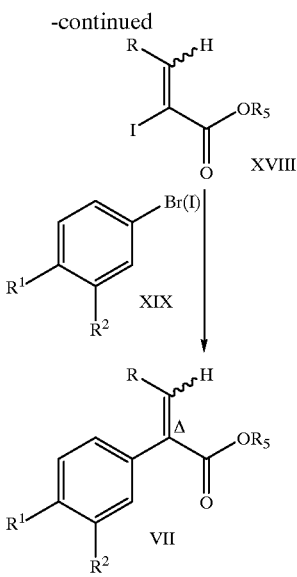

wherein $R^5$ taken together with its attached oxygen forms an acid protecting hydrolyzable carboxylic acid protecting group, R, $R^1$, $R^2$ and Δ are as above.

In scheme 2, the compound of formula XI can be generated in situ from either the corresponding organomagnesium reagent or organozinc reagent and soluble copper reagent (CuCN and 2LiCl) (see for example, Knochel, P.; Singer, R. D, Chem. Rev. 1993, 93, 2117). Then, the compound of formula XI is added to the compound of formula XVII in a 1,4-conjugate addition in a highly regio- and stereoselective manner to obtain a vinylcopper intermediate, which upon iodolysis with iodine produced the compound of formula XVIII in which the R and iodide are in syn relationship to each other. Compound of formula XVIII is thereafter reacted with activated zinc metal (see for example, Knochel, P.; Janakiram Rao. C, Tetrahedron, 1993, 49, 29) to produce a vinylzinc intermediate which then is coupled with the bromide or iodide compound of formula XIX in the presence of a source of Pd(0) to give the compound of formula VII. When this reaction is used, the aromatic substituent is added so that the <u>trans</u> formation across the double bond in the compound of formula VII occurs.

All of the compounds of formula I which include the compounds set forth in the Examples, activated glucokinase in vitro by the procedure of Example A. In this manner, they increase the flux of glucose metabolism which causes increased insulin secretion. Therefore, the compounds of formula I are glucokinase activators useful for increasing insulin secretion.

The following compounds exemplified were tested and found to have excellent glucokinase activator in vivo activity when administered in accordance with the assay described in Example B:

(E)-3-Cyclopentyl-2-(4-methanesulfonyl-phenyl)-N-thiazol-2-yl-acrylamide;

(E)-3-Cyclohexyl-2-(4-methanesulfonyl-phenyl)-N-thiazol-2-yl-acrylamide;

(E)-3-Cycloheptyl-2-(4-methanesulfonyl-phenyl)-N-thiazol-2-yl-acrylamide;

(E)-2-(3-Chloro-4-methanesulfonyl-phenyl)-3-cyclopentyl-N-thiazol-2-yl-acrylamide;

(E)-3-Cyclohexyl-2-(4-methanesulfonyl-3-trifluoromethyl-phenyl)-N-thiazol-2-yl-acrylamide;

(E)-3-Cyclohexyl-2-(4-methanesulfonyl-3-nitro-phenyl)-N-thiazol-2-yl-acrylamide;

(E)-N-(5-Bromo-thiazol-2-yl)-3-cycloheptyl-2-(4-methanesulfonyl-phenyl)-acrylamide;

(E)-2-(3-Chloro-4-methanesulfonyl-phenyl)-3-cyclopentyl-N-pyridin-2-yl-acrylamide;

(E)-N-(5-Bromo-pyridin-2-yl)-3-cyclohexyl-2-(4-methanesulfonyl-3-trifluoromethyl-phenyl)-acrylamide;

(E)-4-Cyclopentyl-2-(4-methanesulfonyl-phenyl)-but-2-enoic acid thiazol-2-ylamide;

(E)-2-[4-Cyclopentyl-2-(4-methanesulfonyl-phenyl)-but-2-enoylamino]-thiazole-4-carboxylic acid methyl ester; and (E)-4-Cyclopentyl-2-(4-methanesulfonyl-3-trifluoromethyl-phenyl)-but-2-enoic acid thiazol-2-ylamide.

This invention will be better understood from the following examples, which are for purposes of illustration and are not intended to limit the invention defined in the claims which follow thereafter.

EXAMPLES

Biological Activity Examples

Example A: In Vitro Glucokinase Activity

Glucokinase Assay: Glucokinase (GK) was assayed by coupling the production of glucose-6-phosphate to the generation of NADH with glucose-6-phosphate dehydrogenase (G6PDH, 0.75–1 kunits/mg; Boehringer Mannheim, Indianapolis, Ind.) from *Leuconostoc mesenteroides* as the coupling enzyme (Scheme 3). Recombinant Scheme 3

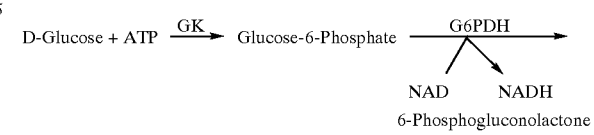

Human liver GK1 was expressed in *E. coli* as a glutathione S-transferase fusion protein (GST-GK) [Liang et al, 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 25° C. in a flat bottom 96-well tissue culture plate from Costar (Cambridge, Mass.) with a final incubation volume of 120 μl. The incubation mixture contained: 25 mM Hepes buffer (pH, 7.1), 25 mM KCl, 5 mM D-glucose, 1 mM ATP, 1.8 mM NAD, 2 mM $MgCl_2$, 1 μM sorbitol-6-phosphate, 1 mM dithiothreitol, test drug or 10% DMSO, 1.8 unit/ml G6PDH, and GK (see below). All organic reagents were >98% pure and were from Boehringer Mannheim with the exceptions of D-glucose and Hepes that were from Sigma Chemical Co, St Louis, Mo. Test compounds were dissolved in DMSO and were added to the incubation mixture minus GST-GK in a volume of 12 μl to yield a final DMSO concentration of 10%. This mix was preincubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 μl GST-GK.

After addition of enzyme, the increase in optical density (OD) at 340 nm was monitored over a 10 minute incubation period as a measure of GK activity. Sufficient GST-GK was added to produce an increase in $OD_{340}$ of 0.08 to 0.1 units over the 10 minute incubation period in wells containing 10% DMSO, but no test compound. Preliminary experiments established that the GK reaction was linear over this period of time even in the presence of activators that produced a 5-fold increase in GK activity. The GK activity in control wells was compared with the activity in wells containing test GK activators, and the concentration of activator that produced a 50% increase in the activity of GK, i.e., the $SC_{1.5}$, was calculated. All of the compounds of formula I described in the Synthesis Examples had an $SC_{1.5}$ less than or equal to 30 µM.

Example B: In Vivo Activity
Glucokinase Activator in vivo Screen Protocol

C57BL/6J. mice are orally dosed via gavage with Glucokinase (GK) activator at 50 mg/kg body weight following a two hour fasting period. Blood glucose determinations are made five times during the six hour post-dose study period.

Mice (n=6) are weighed and fasted for a two hour period prior to oral treatment. GK activators are formulated at 6.76 mg/ml in Gelucire vehicle (Ethanol:Gelucire44/14:PEG400q.s. 4:66:30 v/w/v. Mice are dosed orally with 7.5 µl formulation per gram of body weight to equal a 50 mg/kg dose. Immediately prior to dosing, a pre dose (time zero) blood glucose reading is acquired by snipping off a small portion of the animals tail (~1 mm) and collecting 15 µl blood into a heparinized capillary tube for analysis. Following GK activator administration, additional blood glucose readings are taken at 1, 2, 4 and 6 hours post dose from the same tail wound. Results are interpreted by comparing the mean blood glucose values of six vehicle treated mice with six GK activator treated mice over the six hour study duration. Compounds are considered active when they exhibit a statistically significant ($p \leq 0.05$) decrease in blood glucose compared to vehicle for two consecutive assay time points.

Example 1

(E)-2-(4-Methanesulfonyl-phenyl)-pent-2-enoic acid thiazol-2-ylamide

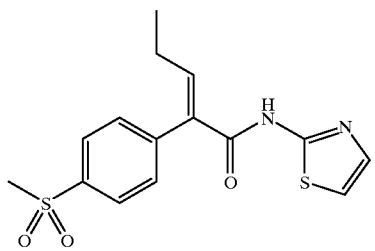

A mixture of lithium chloride (1.7 g, 40 mmol, predried at 130° C. under high vacuum for 2 h) and copper cyanide (1.78 g, 20 mmol) in dry tetrahydrofuran (20 mL) was stirred at 25° C. under argon for 10 min to obtain a clear solution. The reaction mixture was cooled to −70° C. and then slowly treated with a 1 M solution of ethylmagnesium bromide in tetrahydrofuran (20 mL, 20 mmol). After addition, the reaction mixture was allowed to warm to −30° C. where it was stirred for 5 min. The resulting reaction mixture was again cooled back to −70° C. and then slowly treated with methyl propiolate (1.52 g, 18 mmol). The reaction mixture was stirred for 4 h at −40° C. to −30° C. and then cooled to −70° C. to −60° C., at which time, the reaction mixture was treated slowly with a solution of iodine (6.86 g, 27 mmol) in dry tetrahydrofuran (20 mL). After addition of the iodine solution, the cooling bath was removed, and the reaction mixture was allowed to warm to 25° C. where it was stirred for 1 h. The reaction mixture was then poured into a solution consisting of a saturated aqueous ammonium chloride solution (90 mL) and ammonium hydroxide (10 mL), and the organic compound was extracted into diethyl ether (3×50 mL). The combined organic extracts were successively washed with a saturated aqueous sodium thiosulfate solution (1×100 mL) and a saturated aqueous sodium chloride solution (1×100 mL). The organic layer was dried over anhydrous magnesium sulfate, filtered, and concentrated in vacuo. Biotage chromatography (FLASH 40M, Silica, 19/1 hexanes/diethyl ether) afforded (E)-2-iodo-pentenoic acid methyl ester (2.9 g, 67%) as a colorless oil: EI-HRMS m/e calcd for $C_6H_9IO_2$ ($M^+$) 239.9647, found 239.9646.

A mixture of zinc dust (2.36 g, 36 mmol, Aldrich, −325 mesh) and dry tetrahydrofuran (3 mL) under argon was treated with 1,2-dibromoethane (0.28 g, 1.5 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (163 mg, 1.5 mmol), and the suspension was stirred for 15 min at 25° C. The reaction mixture was then treated dropwise with a solution of (E)-2-iodo-pentenoic acid methyl ester (2.9 g, 12 mmol) in dry tetrahydrofuran (3 mL) over 3 min. The reaction mixture was then stirred at 40–45° C. for 1 h and then stirred overnight at 25° C. The reaction mixture was then diluted with dry tetrahydrofuran (10 mL), and the stirring was stopped to allow the excess zinc dust to settle down (~2 h). In a separate reaction flask, bis(dibenzylideneacetone)palladium(0) (135 mg, 0.25 mmol) and triphenylphosphine (260 mg, 1 mmol) in dry tetrahydrofuran (16 mL) was stirred at 25° C. under argon for 10 min and then treated with 4-bromophenyl methyl sulfone (2.11 g, 9 mmol) and the freshly prepared zinc compound in tetrahydrofuran. The resulting brick red solution was heated at 50° C. for 24 h. The reaction mixture was then cooled to 25° C. and then poured into a saturated aqueous ammonium chloride solution (100 ml.), and the organic compound was extracted into ethyl acetate (3×50 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 3/2 hexanes/ethyl acetate) afforded (E)-2-(4-(methanesulfonyl)-phenyl)-pentenoic acid methyl ester (1.88 g, 78%) as a viscous yellow oil: EI-HRMS m/e calcd for $C_{13}H_{16}O_4S$ ($M^+$) 268.0769, found 268.0772.

A solution of (E)-2-(4-(methanesulfonyl)-phenyl)-pentenoic acid methyl ester (1.83 g, 6.82 mmol) in ethanol (30 mL) was treated with a 1N aqueous sodium hydroxide solution (15 mL). The solution was heated at 45–50° C. for 15 h, at which time, thin layer chromatography analysis of the reaction mixture indicated the absence of starting material. The reaction mixture was concentrated in vacuo to remove ethanol. The residue was diluted with water (50 mL) and extracted with diethyl ether (1×50 mL) to remove any neutral impurities. The aqueous layer was then acidified with a 1N aqueous hydrochloric acid solution, and the resulting acid was extracted into ethyl acetate (2×70 mL). The combined organic layers were washed with a saturated aqueous sodium chloride solution (1×100 mL), dried over anhydrous magnesium sulfate, filtered, and concentrated in vacuo to afford (E)-2-(4-(methanesulfonyl)-phenyl)-pentenoic acid (1.43 g, 82%) as a black solid: EI-HRMS m/e calcd for $C_{12}H_{14}O_4S$ (M+H)$^+$ 254.0621, found 254.0623.

A solution of triphenylphosphine (1.23 g, 4.7 mmol) in methylene chloride (15 mL) was cooled to 0° C. and then treated with N-bromosuccinimide (836 mg, 4.7 mmol). The reaction mixture was stirred at 0° C. for 30 min and then treated with a solution of (E)-2-(4-(methanesulfonyl)-phenyl)-pentenoic acid (703 mg, 2.76 mmol) in methylene chloride (5 mL). The clear solution was stirred for 10 min at 0° C. and then allowed to warm to 25° C. where it was stirred for 1.5 h. The reaction mixture was then treated with 2-aminothiazole (829 mg, 8.28 mmol), and the resulting suspension was stirred for 15 h at 25° C. The reaction mixture was then concentrated in vacuo to remove methylene chloride, and the residue was diluted with ethyl acetate (100 mL) and a 1N aqueous hydrochloric acid solution (100 mL). The two layers were separated, and the aqueous layer was extracted with ethyl acetate (1×50 mL). The combined organic extracts were successively washed with a saturated aqueous sodium bicarbonate solution (2×50 mL) and a saturated aqueous sodium chloride solution (1×100 mL), dried over anhydrous magnesium sulfate, filtered, and concentrated in vacuo. Biotage chromatography (FLASH 40M, Silica, 4/1 to 1/1 hexanes/ethyl acetate) afforded (E)-2-(4-methanesulfonyl-phenyl)-pent-2-enoic acid thiazol-2-ylamide (150 mg, 16%) as crystalline solid: mp 155–158° C.; EI-HRMS m/e calcd for $C_{15}H_{16}N_2O_3S_2$ (M$^+$) 336.0602, found 336.0601.

Example 2

(E)-2-(4-Methanesulfonyl-phenyl)-4-methyl-pent-2-enoic acid thiazol-2-ylamide

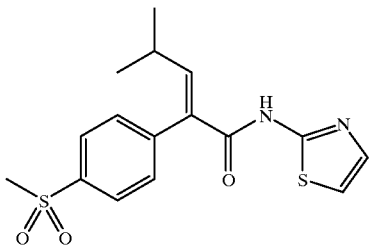

A mixture of lithium chloride (1.69 g, 40 mmol, predried at 130° C. under high vacuum for 2 h) and copper cyanide (1.79 g, 20 mmol) in dry tetrahydrofuran (20 mL) was stirred at 25° C. under argon for 10 min to obtain a clear solution. The reaction mixture was cooled to −70° C. and then slowly treated with a 2M solution of isopropylmagnesium chloride in tetrahydrofuran (10 mL, 20 mmol). After addition, the reaction mixture was allowed to warm to −30° C. where it was stirred for 5 min. The resulting reaction mixture was again cooled back to −70° C. and then slowly treated with methyl propiolate (1.52 g, 18 mmol). The reaction mixture was stirred for 4 h at −40° C. to −30° C. and then cooled to −70° C. to −60° C., at which time, the reaction mixture was treated slowly with a solution of iodine (6.86 g, 27 mmol) in dry tetrahydrofuran (20 mL). After addition of the iodine solution, the cooling bath was removed, and the reaction mixture was allowed to warm to 25° C. where it was stirred for 1 h. The reaction mixture was then poured into a solution consisting of a saturated aqueous ammonium chloride solution (90 mL) and ammonium hydroxide (10 mL), and the organic compound was extracted into diethyl ether (3×50 mL). The combined organic extracts were successively washed with a saturated aqueous sodium thiosulfate solution (1×100 mL) and a saturated aqueous sodium chloride solution (1×100 mL). The organic layer was dried over anhydrous magnesium sulfate, filtered, and concentrated in vacuo. Biotage chromatography (FLASH 40M, Silica, 20/1 hexanes/diethyl ether) afforded (E)-2-iodo-4-methyl-pentenoic acid methyl ester (2.23 g, 49%) as a colorless oil: EI-HRMS m/e calcd for $C_7H_{11}IO_2$ (M$^+$) 253.9804, found 253.9805.

A mixture of zinc dust (1.71 g, 26 mmol, Aldrich, −325 mesh) and dry tetrahydrofuran (2 mL) under argon was treated with 1,2-dibromoethane (0.28 g, 1.5 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (163 mg, 1.5 mmol), and the suspension was stirred for 15 min at 25° C. The reaction mixture was then treated dropwise with a solution of (E)-2-iodo-4-methyl-pentenoic acid methyl ester (2.22 g, 8.7 mmol) in dry tetrahydrofuran (3 mL) over 2 min. The reaction mixture was then stirred at 40–45° C. for 1 h and then stirred overnight at 25° C. The reaction mixture was then diluted with dry tetrahydrofuran (8 mL), and the stirring was stopped to allow the excess zinc dust to settle down (~2 h). In a separate reaction flask, bis(dibenzylideneacetone) palladium(0) (81 mg, 0.15 mmol) and triphenylphosphine (156 mg, 0.6 mmol) in dry tetrahydrofuran (15 mL) was stirred at 25° C. under argon for 10 min and then treated with 4-bromophenyl methyl sulfone (1.64 g, 7 mmol) and the freshly prepared zinc compound in tetrahydrofuran. The resulting brick red solution was heated at 50° C. for 24 h. The reaction mixture was then cooled to 25° C. and then poured into a saturated aqueous ammonium chloride solution (100 mL), and the organic compound was extracted into ethyl acetate (3×50 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 3/2 hexanes/ethyl acetate) afforded (E)-2-(4-(methanesulfonyl)-phenyl)-4-methyl-pentenoic acid methyl ester (1.876 g, 95%) as a viscous yellow oil: EI-HRMS m/e calcd for $C_{14}H_{18}O_4S$ (M$^+$) 282.0926, found 282.0933.

A solution of (E)-2-(4-(methanesulfonyl)-phenyl)-4-methyl-pentenoic acid methyl ester (1.83 g, 6.48 mmol) in ethanol (35 mL) was treated with a 1N aqueous sodium hydroxide solution (15 mL). The solution was heated at 45–50° C. for 15 h, at which time, thin layer chromatography analysis of the reaction mixture indicated the absence of starting material. The reaction mixture was concentrated in vacuo to remove ethanol. The residue was diluted with water (50 mL) and extracted with diethyl ether (1×50 mL) to remove any neutral impurities. The aqueous layer was then acidified with a 1N aqueous hydrochloric acid solution, and the resulting acid was extracted into ethyl acetate (2×70 mL). The combined organic layers were washed with a saturated aqueous sodium chloride solution (1×100 mL), dried over anhydrous magnesium sulfate, filtered, and concentrated in vacuo to afford (E)-2-(4-(methanesulfonyl)-phenyl)-4-methyl-pentenoic acid (1.6 g, 92%) as a white solid: mp 179–182° C.; EI-HRMS m/e calcd for $C_{13}H_{16}O_4S$ (M+H)$^+$ 269.0847, found 269.0858.

A solution of triphenylphosphine (1.11 g, 4.24 mmol) in methylene chloride (15 mL) was cooled to 0° C. and then treated with N-bromosuccinimide (755 mg, 4.24 mmol). The reaction mixture was stirred at 0° C. for 30 min and then treated with a solution of (E)-2-(4-(methanesulfonyl)-phenyl)-4-methyl-pentenoic acid (655 mg, 2.12 mmol) in methylene chloride (4 mL). The clear solution was stirred for 10 min at 0° C. and then allowed to warm to 25° C. where it was stirred for 1.5 h. The reaction mixture was then treated with 2-aminothiazole (636 mg, 6.36 mmol), and the resulting suspension was stirred for 15 h at 25° C. The reaction mixture was then concentrated in vacuo to remove methylene chloride, and the residue was diluted with ethyl acetate (100 mL) and a 1N aqueous hydrochloric acid solution (100 mL). The two layers were separated, and the aqueous layer was extracted with ethyl acetate (1×50 mL). The combined organic extracts were successively washed with a saturated aqueous sodium bicarbonate solution (2×50 mL) and a saturated aqueous sodium chloride solution (1×100 mL), dried over anhydrous magnesium sulfate, filtered, and concentrated in vacuo. Biotage chromatography (FLASH 40M, Silica, 4/1 to 1/1 hexanes/ethyl acetate) afforded an impure mixture of compounds (365 mg). This mixture was dissolved in ethyl acetate (5 mL) and diethyl ether (5 mL) and then treated with hexanes (10 mL). The solids were collected by filtration and washed with hexanes to afford (E)-2-(4-Methanesulfonyl-phenyl)-4-methyl-pent-2-enoic acid thiazol-2-ylamide (219 mg, 29%) as an amorphous solid: EI-HRMS m/e calcd for $C_{16}H_{18}N_2O_3S_2$ (M$^+$) 350.0759, found 350.0754.

Example 3

(E)-3-Cyclopentyl-2-(4-methanesulfonyl-phenyl)-N-thiazol-2-yl-acrylamide

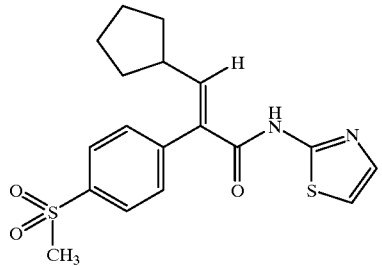

A mixture of aluminum chloride (412.65 g, 3.09 mol) in methylene chloride (1.11 L) was cooled to 0° C. and stirred until the solid material dissolved. The reaction mixture was then slowly treated with ethyl oxalyl chloride (300 mL, 2.69 mol), and the resulting reaction mixture changed from yellow to orange in color. The reaction mixture was then slowly treated with a solution of thioanisole (300 mL, 2.56 mol) in methylene chloride (244 mL) in small portions over 1 h. During the addition of thioanisole, the reaction temperature was kept below 10° C. The resulting reaction mixture was allowed to warm to 25° C. where it was stirred for 1 h. The reaction mixture was then cooled back to 0° C. and then slowly treated with ice/water (800 mL) over 1 h. The reaction mixture was then transferred to a separatory funnel in one-liter portions. The one-liter portions were continuously extracted with methylene chloride until the aqueous layer showed absence of product by thin layer cliromatography. The combined organic layers were dried over magnesium sulfate, filtered, and concentrated in vacuo to afford (4-methylsulfanyl-phenyl)-oxo-acetic acid ethyl ester (481.67 g, 84%) as a yellow liquid which was used without further purification: EI-HRMS m/e calcd for $C_{11}H_{12}O_3S$ (M$^+$) 224.0507, found 224.0500.

A solution of iodomethylcyclopentane (129.38 g, 0.616 mol) and triphenylphosphine (161.54 g, 0.616 mol) in acetonitrile (308 mL) was heated under reflux for 9 d. The reaction mixture was allowed to cool to 25° C. and then concentrated in vacuo to provide a solid. The solid was triturated with diethyl ether and then filtered. The solid was washed well with diethyl ether until the washings showed the absence of iodomethylcyclopentane and triphenylphosphine by thin layer chromatography. The resulting solid was allowed to air dry to afford cyclopentylmethyl triphenylphosphonium iodide (266.92 g, 92%) as a light yellow solid: mp 195–198° C.; FAB-HRMS m/e calcd for $C_{24}H_{26}P$ (M+H)$^+$ 345.1772, found 345.1784.

A suspension of cyclopentylmethyl triphenylphosphonium iodide (151.73 g, 0.321 mol) in dry tetrahydrofuran (494 mL) was cooled to 0° C. and then treated slowly with a 1.0 M solution of lithium bis(trimethylsilyl)amide (309 mL, 0.309 mol). The bright orange reaction mixture was stirred at 0° C. for 1 h. The reaction mixture was then treated with a solution of (4-methylsulfanyl-phenyl)-oxo-acetic acid ethyl ester (55.42 g, 0.247 mol) in dry tetrahydrofuran (100 mL) in small portions. The resulting reaction mixture was stirred at 0° C. for 30 min and then allowed to warm to 25° C. where it was stirred for 6 h. The reaction mixture was then diluted with water (500 mL), at which time, the reaction mixture indicated a pH=11. The reaction mixture was adjusted to pH=6 with a 10% aqueous hydrochloric acid solution and then allowed to sit at 25° C. overnight. The reaction mixture was concentrated in vacuo to remove tetrahydrofuran and then diluted with diethyl ether (1 L). A solid began to precipitate, and the reaction mixture was allowed to sit at 25° C. for 1 h. The solid was filtered and washed well with diethyl ether. The resulting two-layer filtrate was transferred to a separatory funnel, and the layers were separated. The aqueous layer was further extracted with diethyl ether (1×500 mL). The combined organic layers were washed with a saturated aqueous sodium chloride solution (1×500 mL), dried over sodium sulfate, filtered, and concentrated in vacuo. Purification using a plug of silica (Merck Silica gel 60, 230–400 mesh, 9/1 hexanes/ethyl acetate) afforded 3-cyclopentyl-2-(4-methylsulfanyl-phenyl)-acrylic acid ethyl ester (58.93 g, 82%) as a yellow oil consisting of a 1.44:1 mixture of (E):(Z) isomers. The material was used without further separation and characterization.

A solution of the isomeric mixture of 3-cyclopentyl-2-(4-methylsulfanyl-phenyl)-acrylic acid ethyl ester [58.93 g, 0.203 mol, (E):(Z)=1.44:1] in formic acid (203 mL) was cooled to 0° C. and then slowly treated with a 30% aqueous hydrogen peroxide solution (62.2 mL, 0.609 mol). The reaction mixture was stirred at 0° C. for 30 min then allowed to warm to 25° C. where it was stirred for 2 h. The reaction mixture was cooled back to 0° C. and then slowly treated with a saturated aqueous sodium bisulfite solution (1 L). The reaction mixture was then extracted with ethyl acetate (2×700 mL). The combined organic layers were washed with a saturated aqueous sodium chloride solution (1×700 mL), dried over magnesium sulfate, filtered, and concentrated in vacuo to afford 3-cyclopentyl-2-(4-methanesulfonyl-phenyl)-acrylic acid ethyl ester (65.02 g, 99%) as a yellow oil consisting of a 1.63:1 mixture of (E):(Z) isomers. The material was used without further purification and characterization.

A solution of the isomeric mixture of 3-cyclopentyl-2-(4-meth-anesulfonyl-phenyl)-acrylic acid ethyl ester [65.02 g, 0.202 mol, (E):(Z)=1.63:1] in methanol (504 mL) was treated with a 1N aqueous sodium hydroxide solution (423 mL, 0.423 mol). The reaction mixture was stirred at 25° C. for 20 h, at which time, thin layer chromatography indicated the presence of starting material. The reaction mixture was then concentrated in vacuo to remove some of the methanol (300 mL). The resulting reaction mixture was heated under reflux for 1 h, at which time, thin layer indicated the absence of starting material. The reaction mixture was then concentrated in vacuo to remove methanol. The remaining aqueous layer was acidified to pH=1 with concentrated hydrochloric acid and then extracted with ethyl acetate (2×1 L). The combined organic layers were dried over magnesium sulfate, filtered, and concentrated in vacuo to afford 3-cyclopentyl-2-(4-methanesulfonyl-phenyl)-acrylic acid (62.58 g) as a cream solid consisting of a 16.2:1 mixture of (E):(Z) isomers. The cream solid was treated with ethyl acetate (200 mL), and the resulting slurry was heated to a boil. The resulting white solid surrounded by a light yellow liquid of ethyl acetate was allowed to cool to 25° C. The solid was filtered to afford pure (E)-3-cyclopentyl-2-(4-methanesulfonyl-phenyl)-acrylic acid (41.18 g, 69%) as a white solid: mp 200–202° C.; EL-HRMS m/e calcd for $C_{15}H_{18}O_4S$ $(M^+)$ 294.0926, found 294.0921.

A solution of N,N-dimethylformamide (17.5 mL, 226.61 mmol) in dry tetrahydrofuran (420 mL) was cooled to −25° C. under a nitrogen atmosphere and then treated with oxalyl chloride (18.8 mL, 215.42 mmol). The solution became turbid soon after the addition of the oxalyl chloride. The reaction mixture was allowed to warm to 25° C. Upon warming to 25° C., gas evolution began around −20° C., and white solids precipitated with increasing warming temperatures. The reaction mixture was stirred at 25° C. for 15 min, resulting in a thick suspension of white solids. The reaction mixture was then cooled back to −25° C. and then treated with a solution of the (E)-3-cyclopentyl-2-(4-methanesulfonyl-phenyl)-acrylic acid (41.18 g, 139.88 mmol) in dry tetrahydrofuran (300 mL) over a period of 10 min. After complete addition of the (E)-3-cyclopentyl-2-(4-methanesulfonyl-phenyl)-acrylic acid solution, the reaction mixture was allowed to warm to 0° C. where it was stirred for 1 h. During the time at 0° C., the thick solids partially dissolved, leaving a fine suspension of white solids. After 1 h at 25° C., the reaction mixture was cooled to −45° C. The reaction mixture was then treated with a precooled (−45° C.) solution of 2-aminothiazole (44.97 g, 449.02 mmol) and triethylamine (62.6 mL, 449.02 mmol) in dry tetrahyfdrofuran (280 mL) via cannulation over a period of 10 min. The reaction mixture changed from a white suspension to a light brown color after the complete addition of the 2-aminothiazole/triethylamine solution. The reaction mixture was then allowed to warm to 0° C. over 15 min using an ice/water bath. Next, the reaction mixture was allowed to warm to 25° C. over a period of 30 min and then stirred at 25° C. for 1 h. After this time, the reaction mixture was cooled to −25° C. and then treated with a 1 M aqueous citric acid solution (250 mL), and the resulting reaction mixture was allowed to warm to 25° C. The reaction mixture was filtered through a plug of celite to remove the precipitated solids. The celite was washed well with ethyl acetate until the washings showed the absence of product by thin layer chromatography. The two-layer filtrate was transferred to a separatory funnel, and the layers were separated. The aqueous layer was extracted with ethyl acetate (1×500 mL). The organic layer was concentrated in vacuo to remove tetrahydrofuran, and the resulting residue was diluted with ethyl acetate (700 mL). The combined organic layers were washed successively with a 2M aqueous sodium hydrogen sulfate solution (3×200 mL), a saturated aqueous sodium chloride solution (1×200 mL), a 10% aqueous potassium carbonate solution (4×200 mL), and a saturated aqueous sodium chloride solution (1×300 mL). The organic layer was then dried over magnesium sulfate, filtered, and concentrated in vacuo. Flash chromatography (Merck Silica gel 60, 70–230 mesh, 3/2 hexanes/ethyl acetate) afforded (E)-3-cyclopentyl-2-(4-methanesulfonyl-phenyl)-N-thiazol-2-yl-acrylamide (27.93 g, 53%) as a white solid: mp 172–173° C.; FAB-HRMS m/e calcd for $C_{18}H_{20}N_2O_3S_2$ $(M+H)^+$ 377.0993, found 377.0986.

Example 4

(E)-3-Cyclohexyl-2-(4-methanesulfonyl-phenyl)-N-thiazol-2-yl-acrylamide

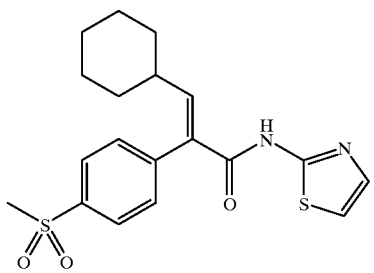

A mixture of zinc dust (16.34 g, 250 mmol, Aldrich, −325 mesh) and dry tetrahydrofuran (6 mL) under argon was treated with 1,2-dibromoethane (0.94 g, 5 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (0.54 g, 5 mmol), and the suspension was stirred for 15 min at 25° C. The reaction mixture was then treated dropwise with a solution of cyclohexyl iodide (21 g, 100 mmol) in dry tetrahydrofuran (30 mL) over 15 min. During the addition, the temperature rose to 60° C., The reaction mixture was then stirred for 3 h at 40–45° C. The reaction mixture was then cooled to 25° C. and diluted with dry tetrahydrofuran (60 mL). The stirring was stopped to allow the excess zinc dust to settle down (~3 h). In a separate reaction flask, a mixture of lithium chloride (8.48 g, 200 mmol, predried at 130° C. under high vacuum for 3 h) and copper cyanide (8.95 g, 100 mmol) in dry tetrahydrofuran (110 mL) was stirred for 10 min at 25° C. to obtain a clear solution. The reaction mixture was cooled to −70° C. and then slowly treated with the freshly prepared zinc solution using a syringe. After the addition, the reaction mixture was allowed to warm to 0° C. where it was stirred for 5 min. The reaction mixture was again cooled back to −70° C. and then slowly treated with methyl propiolate (7.56 g, 90 mmol). The resulting reaction mixture was stirred for 15 h at −70° C. to −50° C. and then slowly treated with a solution of iodine (34.26 g, 135 mmol) in dry tetrahydrofuran (30 mL), with the temperature kept at −70° C. to −60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (400 mL) and ammonium hydroxide (100 mL), and the organic compound was extracted into ethyl acetate (3×250 mL). The combined organic extracts were successively washed with a saturated aqueous sodium thiosulfate solution (1×500 mL) and a saturated aqueous sodium chloride solution (1×500 mL), dried over anhydrous magnesium sulfate, filtered, and concentrated in vacuo. Flash chromatography (Merck Silica gel 60, 230–400 mesh, 9/1 hexanes/diethyl ether) afforded (E)-3-cyclohexyl-2-iodo-acrylic acid methyl ester (26.3 g, 99%) as a light pink oil: EI-HRMS m/e calcd for $C_{10}H_{15}IO_2$ ($M^+$) 294.0117, found 294.0114.

A mixture of zinc dust (2.6 g, 40 mmol, Aldrich, −325 mesh) and dry tetrahydrofuran (3 mL) under argon was treated with 1,2-dibromoethane (0.37 g, 2 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (217 mg, 2 mmol), and the suspension was stirred for 15 min at 25° C. The reaction mixture was then treated dropwise with a solution of (E)-3-cyclohexyl-2-iodo-acrylic acid methyl ester (5.88 g, 20 mmol) in dry tetrahydrofuran (5 mL) over 5 min. During the addition, the temperature rose to 50° C. The reaction mixture was then stirred at 40–45° C. for 1 h and then stirred overnight at 25° C. The reaction mixture was then diluted with dry tetrahydrofuran (10 mL), and the stirring was stopped to allow the excess zinc dust to settle down (~2 h). In a separate reaction flask, bis(dibenzylideneacetone)palladium(0) (270 mg, 0.5 mmol) and triphenylphosphine (520 mg, 2 mmol) in dry tetrahydrofuran (25 mL) was stirred at 25° C. under argon for 10 min and then treated with 4-bromophenyl methyl sulfone (4.23 g, 18 mmol) and the freshly prepared zinc compound in tetrahydrofuran. The resulting brick red solution was heated at 50° C. for 24 h, at which time, thin layer chromatography analysis of the reaction mixture indicated the absence of starting material. The reaction mixture was cooled to 25° C. and then poured into a saturated aqueous ammonium chloride solution (150 mL), and the organic compound was extracted into ethyl acetate (3×100 mL). The combined organic extracts were washed with a saturated aqueous sodium chloride solution (1×200 mL), dried over anhydrous magnesium sulfate, filtered, and concentrated in vacuo. Flash chromatography (Merck Silica gel 60, 230–400 mesh, 3/2 hexanes/ethyl acetate) afforded (E)-3-cyclohexyl-2-(4-methanesulfonyl-phenyl)-acrylic acid methyl ester (5.79 g, 99%) as a low melting white solid: EI-HRMS m/e calcd for $C_{17}H_{22}O_4S$ ($M^+$) 322.1238, found 322.1236.

A solution of (E)-3-cyclohexyl-2-(4-methanesulfonyl-phenyl)-acrylic acid methyl ester (5.7 g, 17.95 mmol) in ethanol (65 mL) was treated with a 1N aqueous sodium hydroxide solution (54 mL). The solution was heated at 45–50° C. for 15 h, at which time, thin layer chromatography analysis of the mixture indicated the absence of starting material. The reaction mixture was then concentrated in vacuo to remove ethanol, and the residue was diluted with water (100 mL) and extracted with diethyl ether (1×150 mL) to remove any neutral impurities. The aqueous layer was acidified with a 1N aqueous hydrochloric acid solution. The resulting acid was extracted into ethyl acetate (2×150 mL). The combined organic layers were washed with a saturated aqueous sodium chloride solution (1×250 mL), dried over anhydrous magnesium sulfate, filtered, and concentrated in vacuo to afford (E)-3-cyclohexyl-2-(4-(methanesulfonyl)-phenyl)-acrylic acid (5.18 g, 94%) as a white solid: mp 195–197° C.; EI-HRMS m/e calcd for $C_{16}H_{20}O_4S$ $(M+H)^+$ 309.1160, found 309.1165.

A solution of triphenylphosphine (8.79 g, 33.52 mmol) in methylene chloride (100 mL) was cooled to 0° C. and then treated with N-bromosuccinimide (5.97 g, 33.52 mmol). The reaction mixture was stirred at 0° C. for 30 min and then treated with a solution of (E)-3-cyclohexyl-2-(4-(methanesulfonyl)-phenyl)-acrylic acid (5.17 g, 16.76 mmol) in methylene chloride (20 mL). The clear solution was stirred for 15 min at 0° C. and then allowed to warm to 25° C. where it was stirred for 1.5 h. The reaction mixture was then treated with 2-aminothiazole (5.04 g, 50.3 mmol), and the resulting suspension was stirred for 2 d at 25° C. The reaction mixture was concentrated in vacuo to remove methylene chloride, and the residue was diluted with ethyl acetate (250 mL) and a 1N aqueous hydrochloric acid solution (150 mL). The two layers were separated, and the aqueous layer was extracted with ethyl acetate (1×100 mL). The combined organic extracts were successively washed with a saturated aqueous sodium bicarbonate solution (1×150 mL) and a saturated aqueous sodium chloride solution (1×250 mL), dried over anhydrous magnesium sulfate, filtered, and, concentrated in vacuo. Flash chromatography (Merck Silica gel 60, 230–400 mesh, 8.5/1.5 to 3/2 hexanes/ethyl acetate) afforded (E)-3-cyclohexyl-2-(4-methanesulfonyl-phenyl)-N-thiazol-2-yl-acrylamide (2.8 g, 42%) as an amorphous solid: mp 167–1694° C.; EI-HRMS m/e calcd for $C_{19}H_{22}O_3S_2$ ($M^+$) 390.1072, found 390.1073.

Example 5

(E)-3-Cycloheptyl-2-(4-methanesulfonyl-phenyl)-N-thiazol-2-yl-acrylamide

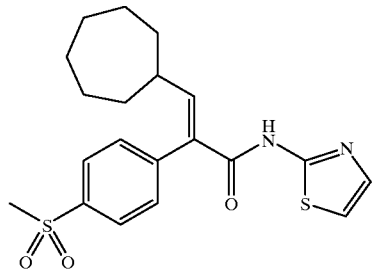

A mixture of magnesium metal (4.81 g, 200 mmol) and dry tetrahydrofuran (10 mL) under argon was treated with a solution of 1,2-dibromoethane (0.94 g, 5 mmol) in dry tetrahydrofuran (5 mL). The resulting reaction mixture was stirred for 10 min to activate the magnesium metal. The reaction mixture was then treated dropwise with a solution of cycloheptyl bromide (17.7 g, 100 mmol) in dry tetrahydrofuran (30 mL), one-fifth portion over a period of 5 min. The resulting reaction mixture was stirred for 5–10 min to initiate the exothermic reaction. The remaining portion of the cycloheptyl bromide solution was then added dropwise while controlling the inside temperature below 50° C. After complete addition, the solution was stirred for 1 h and then diluted with dry tetrahydrofuran (80 mL). In a separate reaction flask, a mixture of lithium chloride (8.48 g, 200 mmol, predried at 130° C. under high vacuum for 3 h) and copper cyanide (8.96 g, 100 mmol) in dry tetrahydrofuran (110 mL) was stirred at 25° C. under argon for 10 min to obtain a clear solution. The reaction mixture was cooled to −70° C. and then slowly treated with the freshly prepared cycloheptylmagnesium bromide. After the addition, the reaction mixture was allowed to warm to −10° C. where it was stirred for 5 min. The resulting reaction mixture was again cooled back to −70° C. and then treated with methyl propiolate (7.57 g, 90 mmol). The reaction mixture was stirred for 15 h at −70° C. to −50° C. and then slowly treated with a solution of iodine (34.3 g, 135 mmol) in dry tetrahydrofuran (30 mL), with the temperature kept at −70° C. to −60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (400 mL) and ammonium hydroxide (100 mL), and the organic compound was extracted into ethyl acetate (3×200 mL). The combined organic extracts were successively washed with a saturated aqueous sodium thiosulfate solution (1×400 mL) and a saturated aqueous sodium chloride solution (1×400 mL). The organic layer was then dried over anhydrous magnesium sulfate, filtered, and concentrated in vacuo. Flash chromatography (Merck Silica gel 60, 230–400 mesh, 20/1 to 10/1 hexanes/diethyl ether) afforded (E)-3-cycloheptyl-2-iodo-acrylic acid methyl ester (17.86 g, 64%) as a colorless oil: EI-IIRMS m/e calcd for $C_{11}H_{17}IO_2$ ($M^+$) 308.0273, found 308.0273.

A mixture of zinc dust (2.6 g, 40 mmol, Aldrich, −325 mesh) and dry tetrahydrofuran (3 mL) under argon was treated with 1,2-dibromoethane (0.38 g, 2 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (220 mg, 2 mmol), and the suspension was stirred for 15 min at 25° C. The reaction mixture was then treated dropwise with a solution of (E)-3-cycloheptyl-2-iodo-acrylic acid methyl ester (6.16 g, 20 mmol) in dry tetrahydrofuran (5 mL) over 10 min. The reaction mixture was then stirred at 40–45° C. for 1 h and then stirred overnight at 25° C. The reaction mixture was then diluted with dry tetrahydrofuran (10 mL), and the stirring was stopped to allow the excess zinc dust to settle down (~2 h). In a separate reaction flask, bis(dibenzylideneacetone) palladium(0) (270 mg, 0.5 mmol) and triphenylphosphine (520 mg, 2 mmol) in dry tetrahydrofuran (25 mL) was stirred at 25° C. under argon for 10 min and then treated with 4-bromophenyl methyl sulfone (4.23 g, 18 mmol) and the freshly prepared zinc compound in tetrahydrofuran. The resulting brick red solution was heated at 50° C. for 24 h. The reaction mixture was cooled to 25° C. and then poured into a saturated aqueous ammonium chloride solution (150 mL), and the organic compound was extracted into ethyl acetate (3×150 mL). The combined organic extracts were washed with a saturated aqueous sodium chloride solution (1×300 mL), dried over anhydrous magnesium sulfate, filtered, and concentrated in vacuo. Flash chromatography (Merck Silica gel 60, 230–400 mesh, 4/1 to 1/1 hexanes/ethyl acetate) afforded (E)-3-cycloheptyl-2-(4-methanesulfonyl-phenyl)-acrylic acid methyl ester (6.01 g, 99%) as a viscous yellow oil: EI-HRMS m/e calcd for $C_{18}H_{24}O_4S$ ($M^+$) 336.1395, found 336.1395.

A solution of (E)-3-cycloheptyl-2-(4-methanesulfonyl-phenyl)-acrylic acid methyl ester (6.01 g, 17.8 mmol) in ethanol (65 mL) was treated with a 1N aqueous sodium hydroxide solution (55 mL). The solution was heated at 45–50° C. for 15 h, at which time, thin layer chromatography analysis of the reaction mixture indicated the absence of starting material. The reaction mixture was concentrated in vacuo to remove ethanol. The residue was diluted with water (100 mL) and extracted with diethyl ether (1×150 mL) to remove any neutral impurities. The aqueous layer was then acidified with a 1N aqueous hydrochloric acid solution, and the resulting acid was extracted into ethyl acetate (2×150 mL). The combined organic layers were washed with a saturated aqueous sodium chloride solution (1×150 mL), dried over anhydrous magnesium sulfate, filtered, and concentrated in vacuo to afford (E)-3-cycloheptyl-2-(4-(methanesulfonyl)-phenyl)-acrylic acid (4.99 g, 86%) as a white solid: mp 164–166° C.; EI-HRMS m/e calcd for $C_{17}H_{22}O_4S$ $(M+H)^+$ 322.1239, found 322.1237.

A solution of triphenylphosphine (8.08 g, 30.8 mmol) in methylene chloride (100 mL) was cooled to 0° C. and then treated with N-bromosuccinimide (5.48 g, 30.8 mmol). The reaction mixture was stirred at 0° C. for 30 min and then treated with a solution of (E)-3-cycloheptyl-2-(4-(methanesulfonyl)-phenyl)-acrylic acid (4.97 g, 15.41 mmol) in methylene chloride (20 mL). The clear solution was stirred for 15 min at 0° C. and then allowed to warm to 25° C. where it was stirred for 1.5 h. The reaction mixture was then treated with 2-aminothiazole (4.63 g, 46.23 mmol), and the resulting suspension was stirred for 2 d at 25° C. The reaction mixture was then concentrated in vacuo to remove methylene chloride, and the residue was diluted with ethyl acetate (250 mL) and a 1N aqueous hydrochloric acid solution (150 mL). The two layers were separated, and the aqueous layer was extracted with ethyl acetate (1×150 mL). The combined organic extracts were successively washed with a saturated aqueous sodium bicarbonate solution (1×250 mL) and a saturated aqueous sodium chloride solution (1×200 mL), dried over anhydrous magnesium sulfate, filtered, and concentrated in vacuo. Flash chromatography (Merck Silica gel 60, 230–400 mesh, 5/1 to 3/2 hexanes/ethyl acetate) afforded (E)-3-cycloheptyl-2-(4-methanesulfonyl-phenyl)-N-thiazol-2-yl-acrylamide (2.7 g, 43%) as an amorphous solid. This compound was dissolved in acetonitrile (~55 mL) and stored overnight at 25° C. The solids were collected by filtration and washed with acetonitrile (5 mL) to obtain (E)-3-cycloheptyl-2-(4-methanesulfonyl-phenyl)-N-thiazol-2-yl-acrylamide (2.1 g, 33%) as a crystalline solid: mp 163–165° C.; EI-HRMS m/e calcd for $C_{20}H_{24}N_2O_3S_2$ ($M^+$) 404.1253, found 404.1251.

Example 6

(E)-3-Cyclooctyl-2-(4-meth anesulfonyl-phenyl)-N-thiazol-2-yl-acrylamide

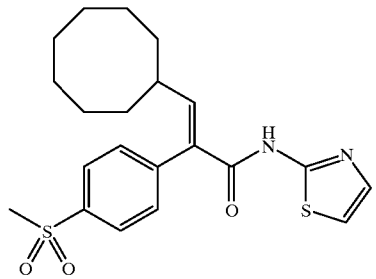

A mixture of magnesium metal (1.94 g, 80 mmol) and dry tetrahydrofuran (3 mL) under argon was treated with a solution of 1,2-dibromoethane (0.56 g, 3 mmol) in dry tetrahydrofuran (2 mL). The resulting reaction mixture was stirred for 10 min to activate the magnesium metal. The reaction mixture was then treated dropwise with a solution of cyclooctyl bromide (7.64 g, 40 mmol) in dry tetrahydrofuran (15 mL), one-fifth portion over a period of 5 min. The resulting reaction mixture was stirred for 5–10 min to initiate the exothermic reaction. The remaining portion of the cyclooctyl bromide solution was then added dropwise while controlling the inside temperature below 50° C. After complete addition, the solution was stirred for 1 h and then diluted with dry tetrahydrofuran (30 mL). In a separate reaction flask, a mixture of lithium chloride (3.39 g, 80 mmol, predried at 130° C. under high vacuum for 3 h) and copper cyanide (3.58 g, 40 mmol) in dry tetrahydrofuran (40 mL) was stirred at 25° C. under argon for 10 min to obtain a clear solution. The reaction mixture was cooled to –70° C. and then slowly treated with the freshly prepared cyclooctylmagnesium bromide. After the addition, the reaction mixture was allowed to warm to –10° C. where it was stirred for 5 min. The resulting reaction mixture was again cooled back to –70° C. and then treated with methyl propiolate (3.02 g, 36 mmol). The reaction mixture was stirred for 15 h at –70° C. to –50° C. and then slowly treated with a solution of iodine (15.22 g, 60 mmol) in dry tetrahydrofuran (15 mL), with the temperature kept at –70° C. to –60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (200 mL) and ammonium hydroxide (50 mL), and the organic compound was extracted into ethyl acetate (3×100 mL). The combined organic extracts were successively washed with a saturated aqueous sodium thiosulfate solution (1×200 mL) and a saturated aqueous sodium chloride solution (1×200 mL). The organic layer was then dried over anhydrous magnesium sulfate, filtered, and concentrated in vacuo. Biotage chromatography (FLASH 40M, Silica, 20/1 to 10/1 hexanes/diethyl ether) afforded (E)-3-cyclooctyl-2-iodo-acrylic acid methyl ester (5.04 g, 43%) as a colorless oil: EI-HRMS m/e calcd for $C_{12}H_{19}IO_2$ ($M^+$) 322.0430, found 322.0432.

A mixture of zinc dust (1.3 g, 20 mmol, Aldrich, –325 mesh) and dry tetrahydrofuran (3 mL) under argon was treated with 1,2-dibromoethane (0.38 g, 2 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (220 mg, 2 mmol), and the suspension was stirred for 15 min at 25° C. The reaction mixture was then treated dropwise with a solution of (E)-3-cyclooctyl-2-iodo-acrylic acid methyl ester (3.22 g, 10 mmol) in dry tetrahydrofuran (4 mL) over 10 min. The reaction mixture was then stirred at 40–45° C. for 1 h and then stirred overnight at 25° C. The reaction mixture was then diluted with dry tetrahydrofuran (8 mL), and the stirring was stopped to allow the excess zinc dust to settle down (~2 h). In a separate reaction flask, bis(dibenzylideneacetone)palladium(0) (135 mg, 0.25 mmol) and triphenylphosphine (260 mg, 1 mmol) in dry tetrahydrofuran (10 mL) was stirred at 25° C. under argon for 10 min and then treated with 4-bromophenyl methyl sulfone (2.12 g, 9 mmol) and the freshly prepared zinc compound in tetrahydrofuran. The resulting brick red solution was heated at 50° C. for 24 h The reaction mixture was cooled to 25° C. and then poured into a saturated aqueous ammonium chloride solution (100 mL), and the organic compound was extracted into ethyl acetate (3×75 mL). The combined organic extracts were washed with a saturated aqueous sodium chloride solution (1×200 mL), dried over anhydrous magnesium sulfate, filtered, and concentrated in vacuo. Flash chromatography (Merck Silica gel 60, 230–400 mesh, 4/1 to 1/1 hexanes/ethyl acetate) afforded (E)-3-cyclooctyl-2-(4-(methanesulfonyl)-phenyl)-acrylic acid methyl ester (2.85 g, 90%) as a light yellow semi-solid: EI-HRMS m/e calcd for $C_{19}H_{26}O_4S$ ($M^+$) 350.1552, found 350.1554.

A solution of (E)-3-cyclooctyl-2-(4-(methanesulfonyl)-phenyl)-acrylic acid methyl ester (2.82 g, 8.05 mmol) in ethanol (30 mL) was treated with a 1N aqueous sodium hydroxide solution (20 mL). The solution was heated at 45–50° C. for 15 h, at which time, thin layer chromatography analysis of the reaction mixture indicated the absence of starting material. The reaction mixture was concentrated in vacuo to remove ethanol. The residue was diluted with water (100 mL) and extracted with diethyl ether (1×75 mL) to remove any neutral impurities. The aqueous layer was then acidified with a 1N aqueous hydrochloric acid solution, and the resulting acid was extracted into ethyl acetate (2×100 mL). The combined organic layers were washed with a saturated aqueous sodium chloride solution (1×150 mL), dried over anhydrous magnesium sulfate, filtered, and concentrated in vacuo to afford (E)-3-cyclooctyl-2-(4-(methanesulfonyl)-phenyl)-acrylic acid (2.64 g, 97%) as a light yellow solid: EI-HRMS m/e calcd for $C_{18}H_{24}O_4S$ ($M^+$) 336.1395, found 336.1390.

A solution of triphenylphosphine (2.09 g, 8 mmol) in methylene chloride (25 mL) was cooled to 0° C. and then treated with N-bromosuccinimide (1.42 g, 8 mmol). The reaction mixture was stirred at 0° C. for 30 min and then treated with a solution of (E)-3-cyclooctyl-2-(4-(methanesulfonyl)-phenyl)-acrylic acid (1.345 g, 4 mmol) in methylene chloride (10 mL). The clear solution was stirred for 15 min at 0° C. and then allowed to warm to 25° C. where it was stirred for 1.5 h. The reaction mixture was then treated with 2-aminothiazole (1.2 g, 12 mmol), and the resulting suspension was stirred for 2 d at 25° C. The reaction mixture was then concentrated in vacuo to remove methylene chloride, and the residue was diluted with ethyl acetate (100 mL) and a 1N aqueous hydrochloric acid solution (100 mL). The two layers were separated, and the aqueous layer was extracted with ethyl acetate (1×50 mL). The combined organic extracts were successively washed with a saturated aqueous sodium bicarbonate solution (1×150 mL) and a saturated aqueous sodium chloride solution (1×100 mL), dried over anhydrous magnesium sulfate, filtered, and concentrated in vacuo. Flash chromatography (Merck Silica gel 60, 230–400 mesh, 5/1 to 3/2 hexanes/ethyl acetate) afforded (E)-3-cyclooctyl-2-(4-methanesulfonyl-phenyl)-N-thiazol-2-yl-acrylamide (1.22 g, 73%) as an amorphous solid: EI-HRMS m/e calcd for $C_{21}H_{26}N_2O_3S_2$ ($M^+$) 418.1385, found 418.1385.

Example 7

(E)-N-(5-Bromo-thiazol-2-yl)-3-cyclopentyl-2-(4-methanesulfonyl-phenyl)-acrylamide

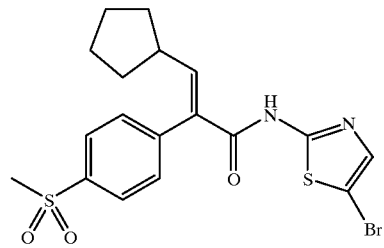

A suspension of (E)-3-cyclopentyl-2-(4-methanesulfonyl-phenyl)-N-thiazol-2-yl-acrylamide (prepared in Example 3, 0.44 g, 1.17 mmol) and N-bromosuccinimide (0.20 g, 1.17 mmol) in carbon tetrachloride (4 mL) at 25° C. was treated with benzoyl peroxide (14.17 mg, 0.058 mmol). The resulting reaction mixture was heated to 90° C. where it was stirred overnight at this temperature. The reaction mixture was allowed to cool to 25° C. and then concentrated in vacuo. The residue was dissolved in ethyl acetate (50 mL). The organic phase was then washed with water (1×50 mL) and a saturated aqueous sodium chloride solution (1×50 mL), dried over anhydrous magnesium sulfate, filtered, and concentrated in vacuo. Biotage chromatography (FLASH 40M, Silica, 4/1 to 1/1 hexanes/ethyl acetate) afforded (E)-N-(5-bromo-thiazol-2-yl)-3-cyclopentyl-2-(4-methanesulfonyl-phenyl)-acrylamide (115 mg, 22%) as white solid: mp 202–205° C.

Example 8

(E)-3-Cyclopentyl-2-(3,4-dichloro-phenyl)-N-thiazol-2-yl-acrylamide

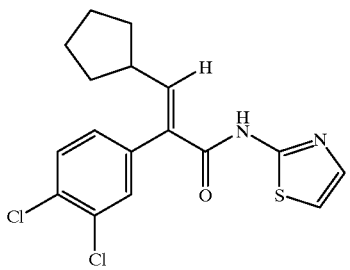

A mixture of aluminum chloride (16.81 g, 126.05 mmol) in methylene chloride (105 mL) was cooled to 5° C. and stirred until the solid material dissolved. The reaction mixture was then slowly treated with methyl oxalyl chloride (8.1 mL, 88.24 mmol), and the resulting reaction mixture was stirred at 5° C. for 30 min. The reaction mixture was then slowly treated with 1,2-dichlorobenzene (12.35 g, 84.04 mmol). The resulting reaction mixture was allowed to warm to 25° C. where it was stirred for 6 h. The reaction mixture was then stored at 0° C. for 15 h. The reaction mixture was slowly poured into ice/water (400 mL). The layers were shaken and separated. The aqueous layer was further extracted with methylene chloride (1×200 mL). The combined organic layers were washed with a saturated aqueous sodium bicarbonate solution (1×200 mL) and water (1×100 mL), dried over magnesium sulfate, filtered, and concentrated in vacuo. Flash chromatography (Merck Silica gel 60, 230–400 mesh, 9/1 hexanes/ethyl acetate) afforded (3,4-dichloro-phenyl)-oxo-acetic acid methyl ester (0.78 g, 4%) as a yellow solid: mp 58.2–63° C.; EL-HRMS m/e calcd for $C_9H_6Cl_2O_3$ (M$^+$) 231.9694, found 231.9699.

A suspension of cyclopentylmethyl triphenylphosphonium iodide (prepared in Example 3, 3.95 g, 8.37 mmol) in dry tetrahydrofuran (10 mL) was cooled to 0° C. and then treated dropwise with a 1.0M solution of sodium bis(trimethylsilyl)amide (8.4 mL, 8.37 mmol). The bright orange reaction mixture was stirred at 0° C. for 45 min. The reaction mixture was then treated with a solution of (3,4-dichloro-phenyl)-oxo-acetic acid methyl ester (1.30 g, 5.58 mmol) in tetrahydrofuran (4 mL). The resulting reaction mixture was allowed to warm to 25° C. where it was stirred for 64 h. The reaction mixture was then concentrated in vacuo to remove tetrahydrofuran. The residue was diluted with water (150 mL) and then extracted with diethyl ether (1×200 mL). The organic layer was dried over sodium sulfate, filtered, and concentrated in vacuo. Flash chromatography (Merck Silica gel 60, 70–230 mesh, 19/1 hexanes/ethyl acetate) afforded the 3 cyclopentyl-2-(3,4-dichloro-phenyl)-acrylic acid methyl ester (821.1 mg, 49%) as a yellow oil consisting of a 4.5:1 mixture of (E):(Z) isomers. The isomeric mixture was used without further separation and characterization.

A solution of the isomeric mixture of 3-cyclopentyl-2-(3,4-dichloro-phenyl)-acrylic acid methyl ester [821.1 mg, 2.74 mmol, (E):(Z)=4.5:1] in tetrahydrofuran (3.4 mL) was treated with a 0.8M aqueous lithium hydroxide solution (3.4 mL, 2.74 mmol). The reaction mixture was stirred at 25° C. for 17 h and then heated under reflux for 4 h. The reaction mixture was allowed to cool to 25° C. and then concentrated in vacuo to remove tetrahydrofuran. The remaining aqueous layer was acidified to pH=2 with a 10% aqueous hydrochloric acid solution and then extracted with ethyl acetate (2×150 mL). The combined organic layers were dried over sodium sulfate, filtered, and concentrated in vacuo. Flash chromatography (Merck Silica gel 60, 70–230 mesh, 1/1 hexanes/ethyl acetate) afforded pure (E)-3-cyclopentyl-2-(3,4-dichloro-phenyl)-acrylic acid (205.4 mg, 26%) as a white solid: mp 119–120° C.; EI-HRMS m/e calcd for $C_{14}H_{14}Cl_2O_2$ (M$^+$) 284.0371, found 284.0370.

A solution of (E)-3-cyclopentyl-2-(3,4-dichloro-phenyl)-acrylic acid (73.9 mg, 0.26 mmol), 0-benzotriazol-1-yl-N,N,N', N'-tetramethyluronium hexafluorophosphate (108.1 mg, 0.29 mmol), and N,N-diisopropylethylamine (136 µL, 0.78 mmol) in dry N,N-dimethylformamide (1.3 mL) was stirred at 25° C. for 15 min and then treated with 2-aminothiazole (51.9 mg, 0.52 mmol). The resulting reaction mixture was stirred at 25° C. for 21 h. The reaction mixture was then concentrated in vacuo to remove N,N-dimethylformamide. The residue was then diluted with ethyl acetate (100 mL). The organic layer was washed with a 10% aqueous hydrochloric acid solution (1×100 mL), a saturated aqueous sodium bicarbonate solution (1×100 mL), and a saturated aqueous sodium chloride solution (1×100 mL). The organic layer was dried over sodium sulfate, filtered and concentrated in vacuo. Flash chromatography (Merck Silica gel 60, 70–230 mesh, 4/1 hexanes/ethyl acetate) afforded two isomeric products. The higher $R_f$ product corresponded to the desired product of (E)-3-cyclopentyl-2-(3,4-dichloro-phenyl)-N-thiazol-2-yl-acrylamide (15.3 mg, 16%), isolated as a white, waxy solid: mp 57–59° C.; EI-HRMS m/e calcd for $C_{17}H_{16}Cl_2N_2OS$ (M$^+$) 366.0360, found 366.0360.

Example 9

(E)-2-(3-Chloro-4-methanesulfonyl-phenyl)-3-cyclopentyl-N-thiazol-2-yl-acrylamide

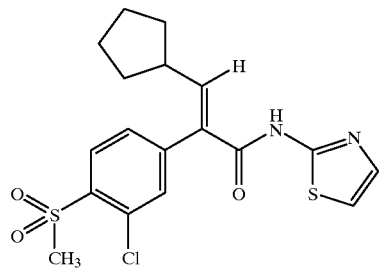

A solution of aluminum chloride (34.8 g, 261.4 mmol) in chloroform (120 mL) under argon was cooled to 0° C. and then treated dropwise with a solution of ethyl oxalyl chloride (18.7 mL, 167.5 mmol) in chloroform (120 mL). The reaction mixture was stirred at 0° C. for 30 min and then treated dropwise with a solution of 2-chlorothioanisole (25.0 g, 156.5 mmol) in chloroform (120 mL). The resulting reaction mixture turned red in color. The reaction mixture was allowed to warm to 25° C. where it was stirred for an additional 3.5 h. The reaction mixture was then slowly quenched with water (500 mL), and upon addition of the water, the reaction mixture turned yellow in color. The resulting solution was then extracted with chloroform (3×50 mL). The organic phase was dried over sodium sulfate, filtered and concentrated in vacuo. Flash chromatography (Merck Silica gel 60, 230–400 mesh, 80/20 hexanes/ethyl acetate) afforded (3-chloro-4-methylsulfanyl-phenyl)-oxo-acetic acid ethyl ester (31.37 g, 77%) as a yellow oil.

A suspension of cyclopentylmethyl triphenylphosphine iodide (prepared in Example 3, 725 mg, 1.53 mmol) in tetrahydrofuran (10 mL) was cooled to 0° C. and then treated with a 1.0M solution of sodium bis(trimethylsilyl)amide in tetrahydrofuran (2.14 ml, 2.14 mmol). The resulting red reaction mixture was stirred at 0° C. for 45 minutes and then slowly treated with a solution of (3-chloro-4-methylsulfanyl-phenyl)-oxo-acetic acid ethyl ester (355 mg, 1.37 mmol) in tetrahydrofuran (5 mL). The reaction mixture was warmed to 25° C. where it was stirred for 20 h. The reaction mixture was then diluted with water (50 mL) and extracted with diethyl ether (3×25 mL). The combined organic layers were dried over sodium sulfate, filtered and concentrated in vacuo. Biotage chromatography (Flash 12M, Silica, 80/20 hexanes/ethyl acetate) afforded 2-(3-chloro-4-methylsulfanyl-phenyl)-3-cyclopentyl-acrylic acid ethyl ester (267 mg, 60%) as a yellow oil consisting of a 2:1 mixture of (E):(Z) isomers. The isomeric mixture was used without further separation and characterization.

A solution of the isomeric mixture of 2-(3-chloro-4-methylsulfanyl-phenyl)-3-cyclopentyl-acrylic acid ethyl ester [100 mg, 0.31 mmol, (E):(Z)=2:1] in methylene chloride (5 mL) was cooled to 0° C. and then treated with 3-chloroperoxybenzoic acid (80% grade, 157 mg, 0.729 mmol). The reaction mixture was stirred at 0° C. for 3.5 h and then diluted with methylene chloride (25 mL). The organic phase was washed with a saturated aqueous sodium carbonate solution (2×10 mL) and a saturated aqueous sodium chloride solution (2×10 mL). The organic layer was dried over sodium sulfate, filtered and concentrated in vacuo. Biotage chromatography (Flash 12M, Silica, 80/20 hexanes/ethyl acetate) afforded 2-(3-chloro-4-methanesulfonyl-phenyl)-3-cyclopentyl-acrylic acid ethyl ester (95 mg, 86%) as a colorless oil consisting of a 2:1 mixture of (E):(Z) isomers. The isomeric mixture was used without further separation and characterization.

A solution of the isomeric mixture of 2-(3-chloro-4-methanesulfonyl-phenyl)-3-cyclopentyl-acrylic acid ethyl ester [500 mg, 1.40 mmol, (E):(Z)=2:1] in ethanol (16 mL) was treated with a solution of potassium hydroxide (393.6 mg, 7.00 mmol) in water (3.7 mL). The yellow solution was stirred for 3 h at 25° C. and then concentrated in vacuo to remove the ethanol. The remaining aqueous layer was acidified to pH=2 with a 1N aqueous hydrochloric acid solution and then extracted with methylene chloride (3×15 mL). The combined organic layers were then dried over sodium sulfate, filtered and concentrated in vacuo. Flash chromatography (Merck Silica gel 60, 230–400 mesh, 75/25 hexanes/ethyl acetate plus 1% acetic acid) afforded (E)-2-(3-chloro-4-methanesulfonyl-phenyl)-3-cyclopentyl-acrylic acid (458 mg, 99%, 95% is the E isomer) as a white foam: FAB-HRMS m/e calcd for $C_{15}H_{17}ClO_4S$ $(M+H)^+$ 329.0614, found 329.0628.

A solution of triphenylphosphine (120 mg, 0.46 mmol) in methylene chloride (5 mL) was cooled to 0° C. and then slowly treated with N-bromosuccinimide (92 mg, 0.52 mmol). The reaction mixture was stirred at 0° C. until the reaction mixture became homogeneous. The resulting light purple reaction mixture was then treated with (E)-2-(3-chloro-4-methanesulfonyl-phenyl)-3-cyclopentyl-acrylic acid (100 mg, 0.30 mmol), and the reaction mixture was stirred at 0° C. for 20 min. The reaction mixture was then allowed to warm to 25° C. where it was stirred for 30 min. After such time, the reaction mixture was treated with 2-aminothiazole (46 mg, 0.46 mmol) and pyridine (0.044 mL, 0.55 mmol), and the resulting reaction mixture was stirred at 25° C. for 16 h. The reaction was then diluted with water (10 mL) and extracted with methylene chloride (3×15 mL). The combined organic layers were dried over sodium sulfate, filtered and concentrated in vacuo. Flash chromatography (Merck Silica gel 60, 230–400 mesh, 70/30 hexanes/ethyl acetate) afforded the (E)-2-(3-chloro-4-methanesulfonyl-phenyl)-3-cyclopentyl-N-thiazol-2-yl-acrylamide (63 mg, 50%) as a yellow oil: EI-HRMS m/e calcd for $C_{18}H_{19}ClN_2O_3S_2$ $(M^+)$ 410.0526, found 410.0529.

Example 10

(E)-2-(3-Bromo-4-methanesulfonyl-phenyl)-3-cyclopentyl-N-thiazol-2-yl-acrylamide

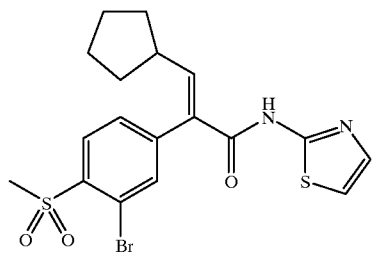

A solution of isoamyl nitrite (8.06 mL, 60 mmol) in dimethyl disulfide (36.02 mL, 400 mmol) at 25° C. was slowly treated with 2,4-dibromoaniline (4.8 g, 20 mmol). The reaction was exothermic with gas evolution. The resulting brown reaction mixture was heated to 80–90° C. for 2 h, at which time, thin layer chromatography analysis of the reaction mixture indicated the absence of starting material. The reaction mixture was cooled to 25° C. and then concentrated in vacuo. The resulting residue was dissolved in ethyl acetate (200 mL). The organic layer was washed successively with a 1N aqueous hydrochloric acid solution (1×200 mL) and a saturated aqueous sodium chloride solution (1×200 mL), dried over anhydrous magnesium sulfate, filtered, and concentrated in vacuo. Purification using a plug of silica (Merck Silica gel 60, 230–400 mesh, 4/1 hexanes/ethyl acetate) afforded 2,4-dibromothioanisole (1 1.04 g, 99%) as a brown oil: EI-HRMS m/e calcd for $C_7H_6Br_2S$ $(M^+)$ 279.8623, found 279.8619.

A solution of 2,4-dibromothioanisole (11.04 g, 39.15 mmol) in methylene chloride (280 mL) was cooled to −10° C. and then treated with 3-chloroperoxybenzoic acid (86% grade, 20.26 g, 117.4 mmol). The reaction mixture was stirred at −10° C. for 10 min and then allowed to warm to 25° C. where it was stirred overnight. At this time, thin layer chromatography analysis of the reaction mixture indicated the absence of starting material. The reaction mixture was then filtered, and the solids were washed with methylene chloride (1×100 mL). The filtrate was then diluted with a 1N aqueous sodium hydroxide solution (100 mL), and the two layers were separated. The organic layer was concentrated in vacuo to afford a brown solid. The brown solid was dissolved in ethyl acetate (200 mL). The organic layer was washed successively with a saturated aqueous sodium bicarbonate solution (2×100 mL) and a saturated aqueous sodium chloride solution (1×100 mL), dried over anhydrous magnesium sulfate, filtered, and concentrated in vacuo to afford a syrup. This syrup was treated with diethyl ether and hexanes to obtain a white solid. The resulting solids were collected by filtration to afford 2,4-dibromophenyl methyl sulfone (10.3 g, 84%) as a white solid: mp 124–126° C.; EI-HRMS m/e calcd for $C_7H_6Br_2O_2S$ (M$^+$) 311.8455, found 311.8455.

A mixture of lithium chloride (8.48 g, 200 mmol, predried at 130° C. under high vacuum for 2 h) and copper cyanide (8.96 g, 100 mmol) in dry tetrahydrofuran (100 mL) was stirred at 25° C. under argon for 10 min to obtain a clear solution. The reaction mixture was cooled to −70° C. and then slowly treated with a 2M solution of cyclopentylmagnesium chloride in diethyl ether (55 mL, 110 mmol). After addition, the reaction mixture was allowed to warm to −30° C. where it was stirred for 5 min. The resulting reaction mixture was again cooled back to −70° C. and then slowly treated with methyl propiolate (7.99 g, 95 mmol). The reaction mixture was stirred for at −60° C. to −50° C. overnight and then cooled to −70° C. to −60° C., at which time, the reaction mixture was treated slowly with a solution of iodine (34.3 g, 135 mmol) in dry tetrahydrofuran (30 mL). After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (200 mL) and ammonium hydroxide (50 mL), and the organic compound was extracted into diethyl ether (3×100 mL). The combined organic extracts were successively washed with a saturated aqueous sodium thiosulfate solution (1×300 mL) and a saturated aqueous sodium chloride solution (1×300 mL). The organic layer was dried over anhydrous magnesium sulfate, filtered, and concentrated in vacuo. Flash chromatography (Merck Silica gel 60, 230–400 mesh, 20/1 hexanes/diethyl ether) afforded (E)-3-cyclopentyl-2-iodo-acrylic acid methyl ester (25.8 g, 97%) as an yellow oil: EI-HRMS m/e calcd for $C_9H_{13}IO_2$ (M$^+$) 279.9960, found 279.9961.

A mixture of zinc dust (650 mg, 10 mmol, Aldrich, −325 mesh) and dry tetrahydrofuran (1 mL) under argon was treated with 1,2-dibromoethane (187 mg, 1.5 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (108 mg, 1 mmol), and the suspension was stirred for 15 min at 25° C. The reaction mixture was then treated dropwise with a solution of (E)-3-cyclopentyl-2-iodo-acrylic acid methyl ester (660 mg, 2.25 mmol) in dry tetrahydrofuran (2 mL) over 3 min. The reaction mixture was then stirred at 40–45° C. for 1 h and then stirred overnight at 25° C. The reaction mixture was then diluted with dry tetrahydrofuran (4 mL), and the stirring was stopped to allow the excess zinc dust to settle down (~2 h). In a separate reaction flask, bis(dibenzylideneacetone) palladium(0) (37 mg, 0.07 mmol) and triphenylphosphine (72 mg, 0.3 mmol) in dry tetrahydrofuran (6 mL) was stirred at 25° C. under argon for 10 min and then treated with 2,4-bromophenyl methyl sulfone (1.05 g, 3.5 mmol) and the freshly prepared zinc compound in tetrahydrofuran. The resulting brick red solution was heated at 40–45° C. over the weekend. The reaction mixture was then cooled to 25° C. and then poured into a saturated aqueous ammonium chloride solution (50 mL), and the organic compound was extracted into ethyl acetate (3×35 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 5/1 hexanes/ethyl acetate) afforded (E)-3-cyclopentyl-2-[3-bromo-4-(methanesulfonyl)-phenyl]-acrylic acid methyl ester (1.03 g, 77.6%) as a light yellow oil.

A solution of (E)-3-cyclopentyl-2-[3-bromo-4-(methanesulfonyl)-phenyl]-acrylic acid methyl ester (357 mg, 0.92 mmol) in ethanol (6 mL) was treated with a 1N aqueous sodium hydroxide solution (2 mL). The solution was heated at 45–50° C. for 15 h, at which time, thin layer chromatography analysis of the reaction mixture indicated the absence of starting material. The reaction mixture was concentrated in vacuo to remove ethanol. The residue was diluted with water (10 mL) and extracted with diethyl ether (1×30 mL) to remove any neutral impurities. The aqueous layer was then acidified with a 1N aqueous hydrochloric acid solution, and the resulting acid was extracted into ethyl acetate (2×20 mL). The combined organic layers were washed with a saturated aqueous sodium chloride solution (1×50 mL), dried over anhydrous magnesium sulfate, filtered, and concentrated in vacuo to afford (E)-3-cyclopentyl-2-[3-bromo-4-(methanesulfonyl)-phenyl]-acrylic acid (339 g, 98%) as an amorphous solid: EI-HRMS m/e calcd for $C_{15}H_{17}BrO_4S$ (M$^+$) 372.0031, found 372.0028.

A solution of triphenylphosphine (467 mg, 1.78 mmol) in methylene chloride (8 mL) was cooled to 0° C. and then treated with N-bromosuccinimide (317 mg, 1.78 mmol). The reaction mixture was stirred at 0° C. for 30 min and then treated with a solution (E)-3-cyclopentyl-2-[3-bromo-4-(methanesulfonyl)-phenyl]-acrylic acid (334 mg, 0.89 mmol) in methylene chloride (4 mL). The reaction mixture was stirred for 15 min at 0° C. and then allowed to warm to 25° C. where it was stirred for 1.5 h. The reaction mixture was then treated with 2-aminothiazole (713 mg, 7.12 mmol), and the resulting suspension was stirred for 2 d at 25° C. The reaction mixture was then concentrated in vacuo to remove methylene chloride, and the residue was diluted with ethyl acetate (40 mL) and a 1N aqueous hydrochloric acid solution (50 mL). The two layers were separated, and the aqueous layer was extracted with ethyl acetate (1×25 mL). The combined organic extracts were successively washed with a 1N aqueous hydrochloric acid solution (1×50 mL), a saturated aqueous sodium bicarbonate solution (1×50 mL) and a saturated aqueous sodium chloride solution (1×50 mL). The organic layer was dried over anhydrous magnesium sulfate, filtered, and concentrated in vacuo. Biotaoe chromatography (FLASH 40S, Silica, 3/1 hexanes/ethyl acetate) afforded the pure (E)-2-(3-bromo-4-methanesulfonyl-phenyl)-3-cyclopentyl-N-thiazol-2-yl-acrylamide (71 mg, 17.5%) as an amorphous white solid: EI-HRMS m/e calcd for $C_{18}H_{19}BrN_2O_3S_2$ (M$^+$) 454.0020, found 454.0025.

Example 11

(E)-3-Cyclohexyl-2-(3,4-difluoro-phenyl)-N-thiazol-2-yl-acrylamide

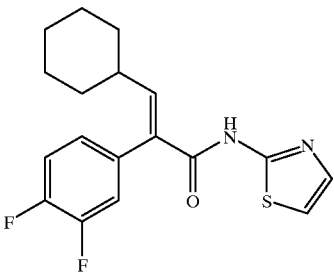

A mixture of zinc dust (980 mg, 15 mmol, Aldrich, −325 mesh) and dry tetrahydrofuran (3 mL) under argon was treated with 1,2-dibromoethane (0.37 g, 2 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (82 mg, 0.75 mmol), and the suspension was stirred for 15 min at 25° C. The reaction mixture was then treated dropwise with a solution of (E)-3-cyclohexyl-2-iodo-acrylic acid methyl ester (prepared in Example 4, 1.47 g, 5 mmol) in dry tetrahydrofuran (1.5 mL) over 3 min. During the addition, the temperature rose to 45° C. The reaction mixture was then stirred at 40–45° C. for 1 h and then stirred overnight at 25° C. The reaction mixture was then diluted with dry tetrahydrofuran (5 mL), and the stirring was stopped to allow the excess zinc dust to settle down (~2 h). In a separate reaction flask, bis(dibenzylideneacetone) palladium(0) (54 mg, 0.1 mmol) and triphenylphosphine (104 mg, 0.4 mmol) in dry tetrahydrofuran (10 mL) was stirred at 25° C. under argon for 10 min and then treated with 3,4-difluoro-iodobenzene (960 mg, 4 mmol) and the freshly prepared zinc compound in tetrahydrofuran. The resulting brick red solution was heated at 25° C. for 15 h, at which time, thin layer chromatography analysis of the reaction mixture indicated the absence of starting material. The reaction mixture was then poured into a saturated aqueous ammonium chloride solution (50 mL), and the organic compound was extracted into diethyl ether (2×50 mL), The combined organic extracts were washed with a saturated aqueous sodium chloride solution (1×50 mL), dried over anhydrous magnesium sulfate, filtered, and concentrated in vacuo. Biotage chromatography (FLASH 40M, Silica, 5/1 hexanes/diethyl ether) afforded (E)-3-cyclohexyl 2-(3,4-difluoro-phenyl)-acrylic acid methyl ester (1.06 g, 95%) as an oil: EI-HRMS m/e calcd for $C_{16}H_{18}F_2O_2$ (M$^+$) 280.1275, found 280.1275.

A solution of (E)-3-cyclohexyl 2-(3,4-difluoro-phenyl)-acrylic acid methyl ester (0.55 g, 1.97 mmol) in ethanol (10 mL) was treated with a 1N aqueous sodium hydroxide solution (4 mL). The solution was heated at 40° C. For 15 h, at which time, thin layer chromatography analysis of the mixture indicated the absence of starting material. The reaction mixture was then concentrated in vacuo to remove ethanol, and the residue was diluted with water (30 mL) and then acidified with a 1N aqueous hydrochloric acid solution. The resulting acid was extracted into ethyl acetate (2×30 mL). The combined organic layers were washed with a saturated aqueous sodium chloride solution (1×50 mL), dried over anhydrous magnesium sulfate, filtered, and concentrated in vacuo to afford (E)-3-cyclohexyl-2-(3,4-difluoro-phenyl)-acrylic acid (0.51 g, 97%) as a white solid: mp 119–121° C.; EI-HRMS m/e calcd for $C_{15}H_{16}F_2O_2$ (M+H)$^+$267.1196, found 267.1200.

A solution of triphenylphosphine (847 mg, 3.2 mmol) in methylene chloride (10 mL) was cooled to 0° C. and then treated with N-bromosuccinimide (575 mg, 3.2 mmol). The reaction mixture was stirred at 0° C. For 30 min and then treated with a solution of (E)-3-cyclohexyl-2-(3,4-difluoro-phenyl)-acrylic acid (507 mg, 1.9 mmol) in methylene chloride (4 mL). The clear solution was stirred for 10 min at 0° C. and then allowed to warm to 25° C. where it was stirred for 1 h. The reaction mixture was then treated with 2-aminothiazole (476 mg, 4.75 mmol), and the resulting suspension was stirred for 15 h at 25° C. The reaction mixture was concentrated in vacuo to remove methylene chloride, and the residue was diluted with ethyl acetate (75 mL). The organic layer was washed successively with a 1N aqueous hydrochloric acid solution (2×30 mL), a saturated aqueous sodium bicarbonate solution (2×30 mL), and a saturated aqueous sodium chloride solution (1×50 mL). The organic layer was then dried over anhydrous magnesium sulfate, filtered, and, concentrated in vacuo. Biotage chromatography (FLASH 40M, Silica, 8/1 to 4/1 hexanes/ethyl acetate) afforded (E)-3-cyclohexyl-2-(3,4-difluoro-phenyl)-N-thiazol-2-yl-acrylamide (520 mg, 78%) as an amorphous solid: EI-HRMS m/e calcd for $C_{18}H_{18}F_2N_2OS$ (M$^+$) 348.1108, found 348.1104.

Example 12

(E)-3-Cyclohexyl-2-(4-methanesulfonyl-3-trifluoromethyl-phenyl)-N-thiazol-2-yl-acrylamide

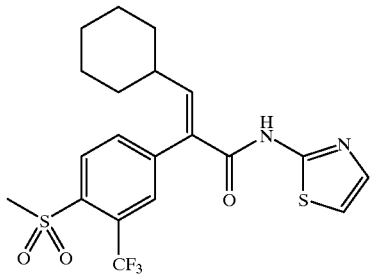

A solution of isoamyl nitrite (4.02 mL, 30 mmol) in dimethyl disulfide (19.8 mL, 220 mmol) at 25° C. was slowly treated with 4-bromo-2-(trifluoromethyl)aniline (4.8 g, 20 mmol). The reaction was exothermic with gas evolution. The resulting brown reaction mixture was heated to 80–90° C. For 2 h, at which time, thin layer chromatography analysis of the reaction mixture indicated the absence of starting material. The reaction mixture was cooled to 25° C. and then concentrated in vacuo. The resulting residue was dissolved in ethyl acetate (200 mL). The organic layer was washed successively with a 1N aqueous hydrochloric acid solution (1×200 mL) and a saturated aqueous sodium chloride solution (1×200 mL), dried over anhydrous magnesium sulfate, filtered, and concentrated in vacuo. Biotage chromatography (FLASH 40M, Silica, 8/1 hexanes/ethyl acetate) afforded 4-bromo-1-methylsulfanyl-2-trifluoromethyl-benzene (4.73 g, 87%) as a brown oil: EI-HRMS m/e calcd for $C_8H_6BrF_3S$ (M$^+$) 269.9326, found 269.9327.

A solution of 4-bromo-1-methylsulfanyl-2-trifluoromethyl-benzene (4.71 g, 17.4 mmol) in methylene chloride (100 mL) was cooled to -10° C. and then treated with 3-chloroperoxybenzoic acid (86% grade, 9.0 g, 52.2 mmol). The reaction mixture was stirred at -10° C. For 10 min and then allowed to warm to 25° C. where it was stirred overnight. At this time, thin layer chromatography analysis of the reaction mixture indicated the absence of starting material. The reaction mixture was then filtered, and the solids were washed with methylene chloride (1×50 mL). The filtrate was concentrated in vacuo. The resulting residue was dissolved in ethyl acetate (100 mL). The organic layer was washed successively with a saturated aqueous sodium bicarbonate solution (2×100 mL) and a saturated aqueous sodium chloride solution (1×100 mL), dried over anhydrous magnesium sulfate, filtered, and concentrated in vacuo to afford a yellow solid. Recrystallization from methylene chloride (20 mL), diethyl ether (10 mL), and hexanes afforded 4-bromo-1-methanesulfonyl-2-trifluoromethyl-benzene (3.46 g, 57%) as a white solid: mp 110–112° C.; EI-HRMS m/e calcd for $C_8H_6BrF_3O_2S$ (M$^+$) 301.9224, found 301.9223.

A mixture of zinc dust (1.3 g, 20 mmol, Aldrich, -325 mesh) and dry tetrahydrofuran (2 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (110 mg 1 mmol), and the suspension was stirred for 15 min at 25° C. The reaction mixture was then treated dropwise with a solution of (E)-3-cyclohexyl-2-iodo-acrylic acid methyl ester (prepared in Example 4, 2.5 g, 8.5 mmol) in dry tetrahydrofuran (3 mL) over 5 min. After the addition, the reaction mixture was stirred for 1 h at 40–45° C. and then stirred overnight at 25° C. The reaction mixture was then diluted with dry tetrahydrofuran (4 mL), and the stirring was stopped to allow the excess zinc dust to settle down (~2 h). In a separate reaction flask, bis (dibenzylideneacetone)palladium(0) (108 mg, 0.2 mmol) and triphenylphosphine (209 mg, 0.8 mmol) in dry tetrahydrofuran (10 mL) was stirred at 25° C. under argon for 10 min and then treated with 4-bromo-1-methanesulfonyl-2-trifluoromethyl-benzene (2.12 g, 7 mmol) and the freshly prepared zinc compound in tetrahydrofuran. The resulting brick red solution was heated at 40–45° C. For 2 d. The reaction mixture was cooled to 25° C. and then poured into a saturated aqueous ammonium chloride solution (100 mL), and the organic compound was extracted into ethyl acetate (3×75 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 9/1 to 3/1 hexanes/ethyl acetate) afforded (E)-3-cyclohexyl-2-(4-methanesulfonyl-3-trifluoromethyl-phenyl)-acrylic acid methyl ester (2.7 g, 99%) as a viscous oil: EI-HRMS m/e calcd for $C_{18}H_{21}F_3O_4S$ (M$^+$) 391.1191, found 391.1200.

A solution of (E)-3-cyclohexyl-2-(4-methanesulfonyl-3-trifluoromethyl-phenyl)-acrylic acid methyl ester (1.8 g, 4.6 mmol) in ethanol (20 mL) was treated with a 1N aqueous sodium hydroxide solution (15 mL). The solution was heated at 45–50° C. For 15 h, at which time, thin layer chromatography analysis of the mixture indicated the absence of starting material. The reaction mixture was then concentrated in vacuo to remove ethanol, and the residue was diluted with water (40 mL) and extracted with diethyl ether (1×50 mL) to remove any neutral impurities. The aqueous layer was acidified with a 1N aqueous hydrochloric acid solution. The resulting acid was extracted into ethyl acetate (2×75 mL). The combined organic layers were washed with a saturated aqueous sodium chloride solution (1×100 mL), dried over anhydrous magnesium sulfate, filtered, and concentrated in vacuo to afford (E)-3-cyclohexyl-2-(4-(methanesulfonyl)-3-(trifluoromethyl)-phenyl)-acrylic acid (1.74 g, 99%) as a white solid: mp 62–64° C.; EI-HRMS m/e calcd for $C_{17}H_{19}F_3O_4S$ (M+H)$^+$ 377.1034, found 377.1041.

A solution of triphenylphosphine (1.39 g, 5.3 mmol) in methylene chloride (50 mL) was cooled to 0° C. and then treated with N-bromosuccinimide (0.94 g, 5.3 mmol). The reaction mixture was stirred at 0° C. For 30 min and then treated with a solution of (E)-3-cyclohexyl-2-(4-(methanesulfonyl)-3-(trifluoromethyl)-phenyl)-acrylic acid (1.00 g, 2.66 mmol) in methylene chloride (10 mL). The clear solution was stirred for 15 min at 0° C. and then allowed to warm to 25° C. where it was stirred for 1.5 h. The reaction mixture was then treated with 2-aminothiazole (800 mg, 7.98 mmol), and the resulting suspension was stirred for 2 d at 25° C. The reaction mixture was concentrated in vacuo to remove methylene chloride, and the residue was diluted with ethyl acetate (100 mL) and a 1N aqueous hydrochloric acid solution (100 mL). The two layers were separated, and the aqueous layer was extracted with ethyl acetate (1×50 mL). The combined organic extracts were successively washed with a 1N aqueous hydrochloric acid solution (1×100 mL), a saturated aqueous sodium bicarbonate solution (1×100 mL) and a saturated aqueous sodium chloride solution (1×100 mL). The organic layer was then dried over anhydrous magnesium sulfate, filtered, and concentrated in vacuo. Biotage chromatography (FLASH 40M, Silica, 5/1 to 3/2 hexanes/ethyl acetate) afforded the (E)-3-cyclohexyl-2-(4-methanesulfonyl-3-trifluoromethyl-phenyl)-N-thiazol-2-yl-acrylamide (367 mg, 30%) as an amorphous solid: EI-HRMS m/e calcd for $C_{20}H_{21}F_3N_2O_3S_2$ (M$^+$) 458.0946, found 458.0947.

Example 13

(E)-N-(5-Bromo-thiazol-2-yl)-3-cyclohexyl-2-(4-methanesulfonyl-3-trifluoromethyl-phenyl)-acrylamide

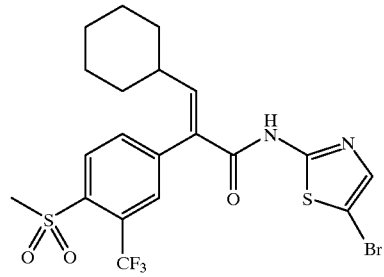

A suspension of (E)-3-cyclohexyl-2-(4-methanesulfonyl-3-trifluoromethyl-phenyl)-N-thiazol-2-yl-acrylamide (prepared in Example 12, 150 mg, 3.27 mmol) and N-bromosuccinimide (69 mg, 0.384 mmol) in carbon tetrachloride (2 mL) at 25° C. was treated with benzoyl peroxide (4.65 mg, 0.02 mmol). The resulting reaction mixture was heated to 90° C. where it was stirred overnight at this temperature. The reaction mixture was then allowed to cool to 25° C. and then concentrated in vacuo. The residue was dissolved in ethyl acetate (25 mL). The organic phase was then washed with water (1×30 mL) and a saturated aqueous sodium chloride solution (1×30 mL), dried over anhydrous magnesium sulfate, filtered, and concentrated in vacuo. Biotage chromatography (FLASH 40S, Silica, 4/1 hexanes/ ethyl acetate) afforded (E)-N-(5-bromo-thiazol-2-yl)-3-cyclohexyl-2-(4-methanesulfonyl-3-trifluoromethyl-phenyl)-acrylamide (59 mg, 33%) as an amorphous white solid.

Example 14

(E)-3-Cyclohexyl-2-(4-methanesulfonyl-3-nitro-phenyl)-N-thiazol-2-yl-acrylamide

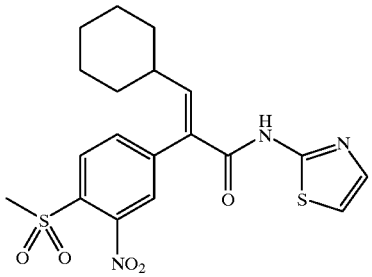

A solution of isoamyl nitrite (2.01 mL, 15 mmol) in dimethyl disulfide (9.9 mL, 110 mmol) at 25° C. was slowly treated with 4-bromO-2-nitrooaniline (2.17 g, 10 mmol). The reaction was exothermic with gas evolution. The resulting brown reaction mixture was heated to 80–90° C. For 2 h, at which time, thin layer chromatography analysis of the reaction mixture indicated the absence of starting material. The reaction mixture was cooled to 25° C. and then concentrated in vacuo. The resulting residue was dissolved in ethyl acetate (100 mL). The organic layer was washed successively with a 1N aqueous hydrochloric acid solution (1×100 mL) and a saturated aqueous sodium chloride solution (1×100 mL), dried over anhydrous magnesium sulfate, filtered, and concentrated in vacuo. Biotage chromatography (FLASH 40M, Silica, 6/1 to 5/1 hexanes/ethyl acetate) afforded 5-bromo-2-thiomethoxy-nitrobenzene (1.9 g, 76%) as a brown solid: EI-HRMS m/e calcd for $C_7H_6BrNO_2S$ ($M^+$) 246.9372, found 246.9368.

A solution of 5-bromo-2-thiomethoxy-nitrobenzene (1.37 g, 5.5 mmol) in methylene chloride (40 mL) was cooled to −10° C. and then treated with 3-chloroperoxybenzoic acid (86% grade, 2.80 g, 16.56 mmol). The reaction mixture was stirred at −10° C. For 10 min and then allowed to warm to 25° C. where it was stirred for 2 h. At this time, thin layer chromatography analysis of the reaction mixture indicated the absence of starting material. The reaction mixture was then concentrated in vacuo. The resulting residue was dissolved in ethyl acetate (100 mL). The organic layer was washed successively with a saturated aqueous sodium bicarbonate solution (2×100 mL) and a saturated aqueous sodium chloride solution (1×100 mL), dried over anhydrous magnesium sulfate, filtered, and concentrated in vacuo. Biotage chromatography (FLASH 40M, Silica, 3/1 hexanes/ethyl acetate) afforded impure 4-bromo-2-nitrophenyl methyl sulfone (1.5 g) as a solid. This solid was dissolved in methylene chloride, treated with hexanes, and then filtered to afford pure 4-bromo-2-nitrophenyl methyl sulfone (0.98 g, 63%) as a white solid: mp 175–177° C.; EI-HRMS m/e calcd for $C_7H_6BrNO_4S$ ($M^+$) 278.9201, found 278.9210.

A mixture of zinc dust (650 mg, 10 mmol, Aldrich, −325 mesh) and dry tetrahydrofuran (1 mL) under argon was treated with 1,2-dibromoethane (187 mg, 1.5 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (110 mg, 1 mmol), and the suspension was stirred for 15 min at 25° C. The reaction mixture was then treated dropwise with a solution of (E)-3-cyclohexyl-2-iodo-acrylic acid methyl ester (prepared in Example 4, 1.2 g, 4.2 mmol) in dry tetrahydrofuran (2 mL) over 5 min. The reaction mixture was then stirred at 40–45° C. For 1 h and then stirred overnight at 25° C. The reaction mixture was then diluted with dry tetrahydrofuran (4 mL), and the stirring was stopped to allow the excess zinc dust to settle down (~2 h). In a separate reaction flask, bis (dibenzylideneacetone)palladium(0) (54 mg, 0.1 mmol) and triphenylphosphine (104 mg, 0.4 mmol) in dry tetrahydrofuran (4 mL) was stirred at 25° C. under argon for 10 min and then treated with 4-bromo-2-nitrophenyl methyl sulfone (0.94 g, 3.35 mmol) and the freshly prepared zinc compound in tetrahydrofuran. The resulting brick red solution was heated at 50° C. For 15 h. The reaction mixture was then cooled to 25° C. and then poured into a saturated aqueous ammonium chloride solution (70 mL), and the organic compound was extracted into ethyl acetate (3×50 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 9/1 to 3/1 hexanes/ethyl acetate) afforded (E)-3-cyclohexyl-2-(4-(methanesulfonyl)-3-nitro-phenyl)-acrylic acid methyl ester (1 g, 82%) as an amorphous white solid: EI-HRMS m/e calcd for $C_{17}H_{21}NO_6S$ ($M^+$) 367.1090, found 367.1091.

A solution of (E)-3-cyclohexyl-2-(4-(methanesulfonyl)-3-nitro-phenyl)-acrylic acid methyl ester (597 mg, 1.62 mmol) in ethanol (10 mL) was treated with a 1N aqueous sodium hydroxide solution (8 mL). The solution was heated at 45–50° C. For 15 h, at which time, thin layer chromatography analysis of the reaction mixture indicated the absence of starting material. The reaction mixture was concentrated in vacuo to remove ethanol. The residue was diluted with water (20 mL) and extracted with diethyl ether (1×50 mL) to remove any neutral impurities. The aqueous layer was then acidified with a 1N aqueous hydrochloric acid solution, and the resulting acid was extracted into ethyl acetate (2×50 mL). The combined organic layers were washed with a saturated aqueous sodium chloride solution (1×100 mL), dried over anhydrous magnesium sulfate, filtered, and concentrated in vacuo to afford (E)-3-cyclohexyl-2-(4-(methanesulfonyl)-3-nitro-phenyl)-acrylic acid (0.514 g, 90%) as a white solid: mp 244–247° C.; EI-HRMS m/e calcd for $C_{16}H_{19}NO_6S$ ($M^+$) 353.0933, found 353.0929.

A solution of triphenylphosphine (720 mg, 2.75 mmol) in methylene chloride (25 mL) was cooled to 0° C. and then treated with N-bromosuccinimide (490 mg, 2.75 mmol). The reaction mixture was stirred at 0° C. For 30 min and then treated with a solution of (E)-3-cyclohexyl-2-(4-(methanesulfonyl)-3-nitro-phenyl)-acrylic acid (485 mg, 1.37 mmol) in methylene chloride (5 mL). The reaction mixture was stirred for 15 min at 0° C. and then allowed to warm to 25° C. where it was stirred for 1.5 h. The reaction mixture was then treated with 2-aminothiazole (412 mg, 4.12 mmol), and the resulting suspension was stirred for 2 d at 25° C. The reaction mixture was then concentrated in vacuo to remove methylene chloride, and the residue was diluted with ethyl acetate (70 mL) and a 1N aqueous hydrochloric acid solution (50 mL). The two layers were separated, and the aqueous layer was extracted with ethyl acetate (1×50 mL). The combined organic extracts were successively washed with a 1N aqueous hydrochloric acid solution (1×100 mL), a saturated aqueous sodium bicarbonate solution (1×100 mL), and a saturated aqueous sodium chloride solution (1×100 mL). The organic layer was dried over anhydrous magnesium sulfate, filtered, and concentrated in vacuo. Biotage chromatography (FLASH 40S, Silica, 5/1 to 3/2 hexanes/ethyl acetate) afforded the (E)-3-cyclohexyl-2-(4-methanesulfonyl-3-nitro-phenyl)-N-thiazol-2-yl-acrylamide (122 mg, 20%) as an amorphous solid: EI-HRMS m/e calcd for $C_{19}H_{21}N_3O_5S_2$ ($M^+$) 435.0923, found 435.0923.

Example 15

(E)-2-(3-Chloro-4-methanesulfonylmethyl-phenyl)-3-cyclohexyl-N-thiazol-2-yl-acrylamide

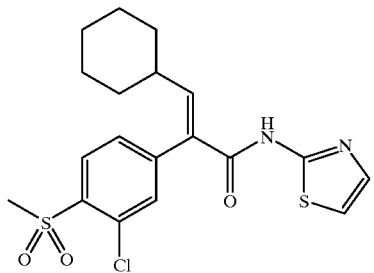

A suspension of 2-chloro-4-iodotoluene (7.57 g, 30 mmol) and N-bromosuccimide (5.34 g, 30 mmol) in carbon tetrachloride (40 mL) was treated with benzoyl peroxide (0.3 g, 1.2 mmol). The reaction mixture was then heated at 90° C. For 15 h, at which time, thin layer chromatography analysis of the reaction mixture indicated the absence of starting material. The reaction mixture was then cooled to 25° C. and concentrated in vacuo. The resulting pink residue was dissolved in ethyl acetate (200 mL). The organic layer was washed successively with water (2×100 mL) and a saturated aqueous sodium chloride solution (1×100 mL), dried over anhydrous magnesium sulfate, filtered, and concentrated in vacuo. Biotage chromatography (FLASH 40M, Silica, hexanes) afforded 2-chloro-4-iodobenzyl bromide (4.83 g, 48%) as a white solid: mp 44–45.5° C.; EI-HRMS m/e calcd for $C_7H_5BrCII$ ($M^+$) 329.8308, found 329.8319.

A solution of 2-chloro-4-iodobenzyl bromide (4.82 g, 14.54 mmol) in N,N-dimethylformamide (30 mL) was treated with sodium thiomethoxide (2.04 g, 29.08 mmol). After the addition, the solution became cloudy and turned to a yellow color. The resulting reaction mixture was stirred for 3 h at 25° C. The reaction mixture was then diluted with ethyl acetate (100 mL). The organic layer was washed successively with water (2×100 mL) and a saturated aqueous sodium chloride solution (1×100 mL), dried over anhydrous magnesium sulfate, filtered, and concentrated in vacuo to afford 2-chloro-4-iodobenzyl methyl sulfide (4.24 g, 97%) as a colorless oil which was used without further purification: EI-HRMS m/e calcd for $C_8H_8CIIS$ ($M^+$) 297.9080, found 297.9078.

A solution of 2-chloro-4-iodobenzyl methyl sulfide (4.24 g, 14.2 mmol) in methylene chloride (100 mL) was cooled to −5° C. and then treated with 3-chloroperoxybenzoic acid (86% grade, 7.35 g, 42.6 mmol). The reaction mixture was stirred at −5° C. for 15 min and then allowed to warm to 25° C. where it was stirred for 3 h. At this time, thin layer chromatography analysis of the reaction mixture indicated the absence of starting material. The solids were filtered and then washed with methylene chloride (1×50 mL). The filtrate was then concentrated in vacuo, and the resulting residue was dissolved in a mixture of ethyl acetate (20 mL) and diethyl ether (100 mL). The organic layer was washed successively with a saturated aqueous sodium bicarbonate solution (2×100 mL), a saturated aqueous sodium bisulfite solution (1×100 mL), and a saturated aqueous sodium chloride solution (1×100 mL). The organic layer was then dried over anhydrous magnesium sulfate, filtered, and concentrated in vacuo. Biotage chromatography (FLASH 40M, Silica, 10/1/10 hexanes/ethyl acetate/methylene chloride) afforded 2-chloro-4-iodobenzyl methyl sulfone (3.67 g, 78%) as a white solid: mp 125–127° C.; EI-HRMS m/e calcd for $C_8H_8CIIO_2S$ ($M^+$) 329.8979, found 329.8969.

A mixture of zinc dust (650 mg, 10 mmol, Aldrich, −325 mesh) and dry tetrahydrofuran (2 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (110 mg, 1 mmol), and the suspension was stirred for 15 min at 25° C. The reaction mixture was then treated dropwise with a solution of (E)-3-cyclohexyl-2-iodo-acrylic acid methyl ester (prepared in Example 4, 1.17 g, 4 mmol) in dry tetrahydrofuran (2 mL) over 5 min. The reaction mixture was then stirred at 40–45° C. for 1 h and then stirred overnight at 25° C. The reaction mixture was then diluted with dry tetrahydrofuran (4 mL), and the stirring was stopped to allow the excess zinc dust to settle down (~2 h). In a separate reaction flask, bis (dibenzylideneacetone)palladium(0) (54 mg, 0.1 mmol) and triphenylphosphine (104 mg, 0.4 mmol) in dry tetrahydrofuran (4 mL) was stirred at 25° C. under argon for 10 min and then treated with 2-chloro-4-iodobenzyl methyl sulfone (0.85 g, 2.57 mmol) and the freshly prepared zinc compound in tetrahydrofuran. The resulting brick red solution was heated at 50° C. for 2 d. The reaction mixture was then cooled to 25° C. and then poured into a saturated aqueous ammonium chloride solution (50 mL), and the organic compound was extracted into ethyl acetate (3×30 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 9/1 to 3/1 hexanes/ethyl acetate) afforded (E)-3-cyclohexyl-2-(3-chloro-4-((methylene)-methylsulfonyl)-phenyl)-acrylic acid methyl ester (0.94 g, 98%) as an amorphous white solid: EI-HRMS m/e calcd for $C_{18}H_{23}CIO_4S$ ($M^+$) 370.1005, found 370.1001.

A solution of (E)-3-cyclohexyl-2-(3-chloro-4-((methylene)-methylsulfonyl)-phenyl)-acrylic acid methyl ester (887 mg, 2.4 mmol) in ethanol (10 mL) was treated with a 1N aqueous sodium hydroxide solution (8 mL). The solution was heated at 45–50° C. for 15 h, at which time, thin layer chromatography analysis of the reaction mixture indicated the absence of starting material. The reaction mixture was concentrated in vacuo to remove ethanol. The residue was diluted with water (20 mL) and extracted with diethyl ether (1× 50 mL) to remove any neutral impurities. The aqueous layer was then acidified with a 1N aqueous hydrochloric acid solution, and the resulting acid was extracted into ethyl acetate (2×50 mL). The combined organic layers were washed with a saturated aqueous sodium chloride solution (1×100 mL), dried over anhydrous magnesium sulfate, filtered, and concentrated in vacuo to afford the (E)-3-cyclohexyl-2-(3-chloro-4-((methylene)-methylsulfonyl)-phenyl)-acrylic acid (0.847 g, 99%) as a white solid: mp 105–108° C.; EI-HRMS m/e calcd for $C_{17}H_{21}ClO_4S$ ($M^+$) 356.0849, found 356.0844.

A solution of triphenylphosphine (1.23 g, 4.69 mmol) in methylene chloride (15 mL) was cooled to 0° C. and then treated with N-bromosuccinimide (830 mg, 4.69 mmol). The reaction mixture was stirred at 0° C. for 30 min and then treated with a solution of (E)-3-cyclohexyl-2-(3-chloro-4-((methylene)-methylsulfonyl)-phenyl)-acrylic acid (837 mg, 2.34 mmol) in methylene chloride (6 mL). The reaction mixture was stirred for 1 5 min at 0° C. and then allowed to warm to 25° C. where it was stirred for 1.5 h. The reaction mixture was then treated with 2-aminothiazole (702 mg, 7.02 mmol), and the resulting suspension was stirred for 2 d at 25° C. The reaction mixture was then concentrated in vacuo to remove methylene chloride, and the residue was diluted with ethyl acetate (70 mL) and a 1N aqueous hydrochloric acid solution (50 mL). The two layers were separated, and the aqueous layer was extracted with ethyl acetate (1×50 mL). The combined organic extracts were successively washed with a 1N aqueous hydrochloric acid solution (1×100 mL), a saturated aqueous sodium bicarbonate solution (1×100 mL), and a saturated aqueous sodium chloride solution (1×100 mL). The organic layer was dried over anhydrous magnesium sulfate, filtered, and concentrated in vacuo. Biotage chromatography (FLASH 40M, Silica, 5/1 to 3/2 hexanes/ethyl acetate) afforded the pure (E)-2-(3-chloro-4-methanesulfonylmethyl-phenyl)-3-cyclohexyl-N-thiazol-2-yl-acrylamide (596 mg, 58%) as a white solid: mp 218–221° C.; EI-HRMS m/e calcd for $C_{20}H_{23}Cl\ N_2O_3S_2$ ($M^+$) 438.0839, found 438.0834.

Example 16

(E)-N-(5-Bromo-thiazol-2-yl)-3-cycloheptyl-2-(4-methanesulfonyl-phenyl)-acrylamide

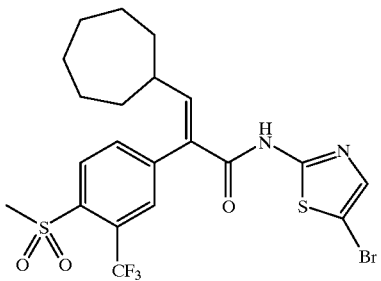

A suspension of (E)-3-cycloheptyl-2-(4-methanesulfonyl-phenyl)-N-thiazol-2-yl-acrylamide (prepared in Example 5, 202 mg, 0.5 mmol) and N-bromosuccinimide (89 mg, 0.5 mmol) in carbon tetrachloride (2 mL) at 25° C. was treated with benzoyl peroxide (6 mg, 0.025 mmol). The resulting reaction mixture was heated to 90° C. where it was stirred overnight at this temperature. The reaction mixture was allowed to cool to 25° C. and then concentrated in vacuo. The residue was dissolved in ethyl acetate (25 mL). The organic phase was then washed with water (1×30 mL) and a saturated aqueous sodium chloride solution (1×30 mL), dried over anhydrous magnesium sulfate, filtered, and concentrated in vacuo. Biotage chromatography (FLASH 40M, Silica, 4/1 hexanes/ethyl acetate) afforded the (E)-N-(5-bromo-thiazol-2-yl)-3-cycloheptyl-2-(4-methanesulfonyl-phenyl)-acrylamide (86 mg, 36%) as a white solid: mp 159–163° C.

Example 17

(E)-3-Cycloheptyl-2-(4-methanesulfonyl-3-trifluoromethyl-phenyl)-N-thiazol-2-yl-acrylamide

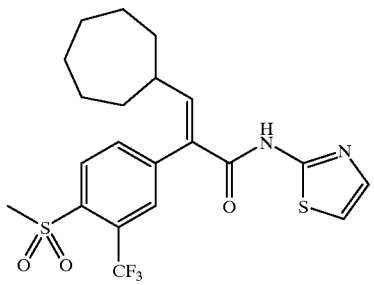

A mixture of zinc dust (390 mg, 6 mmol, Aldrich, −325 mesh) and dry tetrahydrofuran (1 mL) under argon was treated with 1,2-dibromoethane (94 mg, 0.5 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (55 mg, 0.5 mmol), and the suspension was stirred for 15 min at 25° C. The reaction mixture was then treated dropwise with a solution of (E)-3-cycloheptyl-2-iodo-acrylic acid methyl ester (prepared in Example 5, 616 mg, 2 mmol) in dry tetrahydrofuran (2 mL). After the addition, the reaction mixture was stirred for 1 h at 40–45° C. and then stirred overnight at 25° C. The reaction mixture was then diluted with dry tetrahydroftiran (2 mL), and the stirring was stopped to allow the excess zinc dust to settle down (~2 h). In a separate reaction flask, bis(dibenzylideneacetone)palladium(0) (27 mg, 0.05 mmol) and triphenylphosphine (52 mg, 0.2 mmol) in dry tetrahydrofuran (4 mL) was stirred at 25° C. under argon for 10 min and then treated with 4-bromo-1-methanesulfonyl-2-trifluoromethyl-benzene (prepared in Example 12, 303 mg, 1 mmol) and the freshly prepared zinc compound in tetrahydrofuran. The resulting brick red solution was heated at 40–45° C. for 24 h. The reaction mixture was cooled to 25° C. and then poured into a saturated aqueous ammonium chloride solution (30 mL), and the organic compound was extracted into ethyl acetate (3×25 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 4/1 hexanes/ethyl acetate) afforded (E)-3-cycloheptyl-2-(4-methanesulfonyl-3-trifluoromethyl-phenyl)-acrylic acid methyl ester (387 mg, 95%) as a viscous oil.

A solution of (E)-3-cycloheptyl-2-(4-methanesulfonyl-3-trifluoromethyl-phenyl)-acrylic acid methyl ester (387 mg, 0.96 mmol) in ethanol (6 mL) was treated with a 1N aqueous sodium hydroxide solution (2 mL). The solution was heated at 45–50° C. for 15 h, at which time, thin layer chromatography analysis of the mixture indicated the absence of starting material. The reaction mixture was then concentrated in vacuo to remove ethanol, and the residue was diluted with water (20 mL) and extracted with diethyl ether (1×30 mL) to remove any neutral impurities. The aqueous layer was acidified with a 1N aqueous hydrochloric acid solution. The resulting acid was extracted into ethyl acetate (2×35 mL). The combined organic layers were washed with a saturated aqueous sodium chloride solution (1×100 mL), dried over anhydrous magnesium sulfate, filtered, and concentrated in vacuo to afford the (E)-3-cycloheptyl-2-(4-(methanesulfonyl)-3-(trifluoromethyl)-phenyl)-acrylic acid (268 mg, 72%) as a brown solid: mp 151–156° C.

A solution of triphenylphosphine (341 mg, 1.3 mmol) in methylene chloride (7 mL) was cooled to 0° C. and then treated with N-bromosuccinimide (231 mg, 1.3 mmol). The reaction mixture was stirred at 0° C. for 30 min and then treated with (E)-3-cycloheptyl-2-(4-(methanesulfonyl)-3-(trifluoromethyl)-phenyl)-acrylic acid (255 mg, 0.65 mmol). After 15 min at 0° C., the reaction mixture became clear. The clear solution was then allowed to warm to 25° C. where it was stirred for 1.5 h. The reaction mixture was then treated with 2-aminothiazole (193 mg, 1.95 mmol), and the resulting suspension was stirred for 2 d at 25° C. The reaction mixture was concentrated in vacuo to remove methylene chloride, and the residue was diluted with ethyl acetate (50 mL) and a 1N aqueous hydrochloric acid solution (50 mL). The two layers were separated, and the aqueous layer was extracted with ethyl acetate (1×30) mL). The combined organic extracts were successively washed with a 1N aqueous hydrochloric acid solution (1×50 mL), a saturated aqueous sodium bicarbonate solution (1×50 mL) and a saturated aqueous sodium chloride solution (1×50 mL). The organic layer was then dried over anhydrous magnesium sulfate, filtered, and concentrated in vacuo. Biotage chromatography (FLASH 40S, Silica, 4/1 to 2/1 hexanes/ethyl acetate) afforded the pure (E)-3-cycloheptyl-2-(4-methanesulfonyl-3-trifluoromethyl-phenyl)-N-thiazol-2-yl-acrylamide (133 mg, 43%) as an amorphous solid.

Example 18

(E)-N-(5-Bromo-thiazol-2-yl)-3-cycloheptyl-2-(4-methanesulfonyl-3-trifluoromethyl-phenyl)-acrylamide

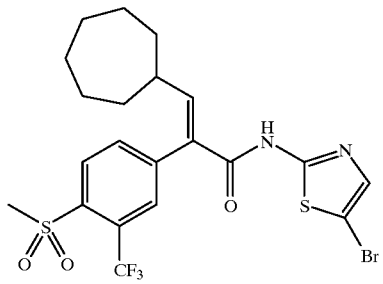

A suspension of (E)-3-cycloheptyl-2-(4-methanesulfonyl-3-trifluoromethyl-phenyl)-N-thiazol-2-yl-acrylamide (prepared in Example 17, 63 mg, 0.133 mmol) and N-bromosuccinimide (26 mg, 0.146 mmol) in carbon tetrachloride (2 mL) at 25° C. was treated with benzoyl peroxide (2 mg, 0.006 mmol). The resulting reaction mixture was heated to 90° C. where it was stirred overnight at this temperature. The reaction mixture was allowed to cool to 25° C. and then concentrated in vacuo. The residue was dissolved in ethyl acetate (25 mL). The organic phase was then washed with water (1×30 mL) and a saturated aqueous sodium chloride solution (1×30 mL), dried over anhydrous magnesium sulfate, filtered, and concentrated in vacuo. Biotage chromatography (FLASH 40S, Silica, 5/1 hexanes/ethyl acetate) afforded the (E)-N-(5-bromo-thiazol-2-yl)-3-cycloheptyl-2-(4-methanesulfonyl-3-trifluoromethyl-phenyl)-acrylamide (35.5 mg, 48%) as an amorphous white solid.

Example 19

(E)-2-(3-Chloro-4-methanesulfonyl-phenyl)-3-cyclopentyl-N-pyridin-2-yl-acrylamide

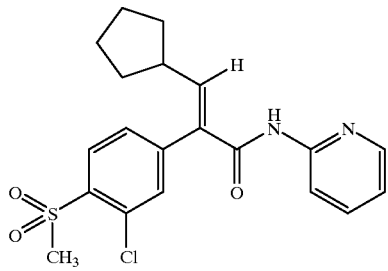

A solution of triphenylphosphine (266 mg, 01.01 mmol) in methylene chloride (11 mL) was cooled to 0° C. and then slowly treated with N-bromosuccinimide (204 mg, 1.15 mmol). The reaction mixture was stirred at 0° C. until the reaction mixture became homogeneous. The resulting light purple reaction mixture was then treated with (E)-2-(3-chloro-4-methanesulfonyl-phenyl)-3-cyclopentyl-acrylic acid (prepared in Example 9, 222 mg, 0.68 mmol), and the reaction mixture was stirred at 0° C. for 20 min. The reaction mixture was then allowed to warm to 25° C. where it was stirred for 30 min. After such time, the reaction mixture was treated with 2-aminopyridine (95 mg, 1.01 mmol) and pyridine (0.098 mL, 1.22 mmol), and the resulting reaction mixture was stirred at 25° C. for 16 h. The reaction was then diluted with water (10 mL) and extracted with methylene chloride (3×15 mL). The combined organic layers were dried over sodium sulfate, filtered and concentrated in vacuo. Biotage chromatography (FLASH 40S, Silica, 75/25 hexanes/ethyl acetate) afforded (E)-2-(3-chloro-4-methanesulfonyl-phenyl)-3-cyclopentyl-N-pyridin-2-yl-acrylamide (70 mg, 25%) as a yellow glassy solid: EI-HRMS m/e calcd for $C_{20}H_{21}ClN_2O_3S$ ($M^+$) 404.0961, found 404.0962.

Example 20

(E)-N-(5-Bromo-pyridin-2-yl)-3-cyclohexyl-2-(4-methanesulfonyl-3-trifluoromethyl-phenyl)-acrylamide

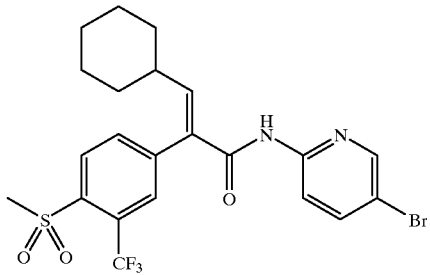

A solution of triphenylphosphine (525 mg, 2 mmol) in methylene chloride (12 mL) was cooled to 0° C. and then treated with N-bromosuccinimide (356 mg, 2 mmol). The reaction mixture was stirred at 0° C. for 30 min and then treated with (E)-3-cyclohexyl-2-(4-(methanesulfonyl)-3-(trifluoromethyl)-phenyl)-acrylic acid (prepared in Example 12, 376 mg, 1 mmol). The reaction mixture was stirred at 25°

C. for 15 min and then allowed to warm to 25° C. where it was stirred for 1.5 h. The reaction mixture was then treated with 2-amino-5-bromopyridine (519 mg, 3 mmol), and the resulting suspension was stirred for 3 d at 25° C. The reaction mixture was concentrated in vacuo to remove methylene chloride, and the residue was diluted with ethyl acetate (50 mL) and a 1N aqueous hydrochloric acid solution (50 mL). The two layers were separated, and the aqueous layer was extracted with ethyl acetate (1×30 mL). The combined organic extracts were successively washed with a saturated aqueous sodium bicarbonate solution (1×50 mL) and a saturated aqueous sodium chloride solution (1×50 mL). The organic layer was then dried over anhydrous magnesium sulfate, filtered, and concentrated in vacuo. Biotage chromatography (FLASH 40S, Silica, 4/1 to 2/1 hexanes/ethyl acetate) afforded the (E)-N-(5-bromo-pyridin-2-yl)-3-cyclohexyl-2-(4-methanesulfonyl-3-trifluoromethyl-phenyl)-acrylamide (44 mg, 8.3%) as an amorphous solid: EI-HRMS m/e calcd for $C_{22}H_{22}BrF_3N_2O_3S$ ($M^+$) 530.0487, found 530.0484.

Example 21

(E)-4-Cyclopentyl-2-(4-methanesulfonyl-phenyl)-but-2-enoic acid thiazol-2-ylamide

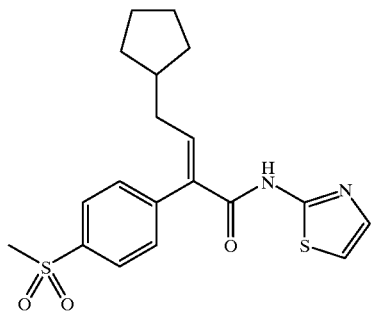

A mixture of zinc dust (3.92 g, 60 mmol, Aldrich, −325 mesh) and dry tetrahydrofuran (4 mL) under argon was treated with 1,2-dibromoethane (0.56 g, 3 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (0.32 g, 3 mmol, and the suspension was stirred for 15 min at 25° C. The reaction mixture was then treated dropwise with a solution of cyclopentylmethyl iodide (4.2 g, 20 mmol) in dry tetrahydrofuran (7 mL) over 5 min. During the addition, the temperature rose to 50° C., and the reaction mixture was stirred overnight at 40–45° C. The reaction mixture was then cooled to 25° C. and diluted with dry tetrahydrofuran (5 mL). The stirring was stopped to allow the excess zinc dust to settle down (~2 h). In a separate reaction flask, a mixture of lithium chloride (1.7 g, 40 mmol, predried at 130° C. under high vacuum for 2 h) and copper cyanide (1.79 g, 20 mmol) in dry tetrahydrofuran (20 mL) was stirred for 10 min at 25° C. to obtain a clear solution. The reaction mixture was cooled to −70° C. and then the slowly treated with the freshly prepared zinc solution using a syringe. After the addition, the reaction mixture was allowed to warm to −30° C., where it was stirred for 5 min. The reaction mixture was again cooled back to −70° C. and then slowly treated with methyl propiolate (1.52 g, 18 mmol). The reaction mixture was stirred for 4 h at −40° C. to −30° C. and then slowly treated with a solution of iodine (6.85 g, 27 mmol) in dry tetrahydrofuran (10 mL), with the temperature kept at −70° C. to −60° C. After the addition of the iodine solution, the cooling bath was removed, and the reaction mixture was allowed to warm to 25° C. where it was stirred for 1 h. The reaction mixture was then poured into a solution consisting of a saturated aqueous ammonium chloride solution (90 mL) and ammonium hydroxide (10 mL), and the organic compound was extracted into diethyl ether (3×50 mL). The combined ether extracts were successively washed with a saturated aqueous sodium thiosulfate solution (1×100 mL) and a saturated aqueous sodium chloride solution (1×100 mL), dried over anhydrous magnesium sulfate, filtrated, and concentrated in vacuo. Biotage chromatography (FLASH 40M, Silica, 9/1 hexanes/diethyl ether) afforded (E)-4-cyclopentyl-2-iodo-but-2-enoic acid methyl ester (4.56 g, 86%) as a colorless oil: EI-HRMS m/e calcd for $C_{10}H_{15}IO_2$ ($M^+$) 294.0116, found 294.0114.

A mixture of zinc dust (0.98 g, 15 mmol, Aldrich, −325 mesh) and dry tetrahydrofuran (3 mL) under argon was treated with 1,2-dibromoethane (0.14 g, 0.75 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (82 mg, 0.75 mmol), and the suspension was stirred for 15 min at 25° C. The reaction mixture was then treated dropwise with a solution of (E)-4-cyclopentyl-2-iodo-but-2-enoic acid methyl ester (1.47 g, 5 mmol) in dry tetrahydrofuran (1.5 mL) over 3 min. After the addition, the reaction mixture was stirred for 1 h at 40–45° C. and then stirred overnight at 25° C. The reaction mixture was then diluted with dry tetrahydrofuran (5 mL), and the stirring was stopped to allow the excess zinc dust to settle down (~2 h). In a separate reaction flask, bis(dibenzylideneacetone)palladium(0) (54 mg, 0.1 mmol) and triphenylphosphine (104 mg, 0.4 mmol) in dry tetrahydrofuran (10 mL) was stirred at 25° C. under argon for 10 min and then treated with 4-bromophenyl methyl sulfone (0.94 g, 4 mmol) and the freshly prepared zinc compound in tetrahydrofuran. The resulting brick red solution was heated at 50° C. for 24 h, at which time, thin layer chromatography analysis of the reaction mixture indicated the absence of starting material. The reaction mixture was cooled to 25° C. and then poured into a saturated aqueous ammonium chloride solution (75 mL), and the organic compound was extracted into diethyl ether (3×50 mL). The combined ether extracts were washed with a saturated aqueous sodium chloride solution (1×100 mL), dried over anhydrous magnesium sulfate, filtered, and concentrated in vacuo. Biotage chromatography (FLASH 40M, Silica, 3/7 hexanes/diethyl ether) afforded (E)-4-cyclopentyl-2-(4-methanesulfonyl-phenyl)-but-2-enoic acid methyl ester (1.10 g, 86%) as a colorless oil: EI-HRMS m/e calcd for $C_{17}H_{22}O_4S$ ($M^+$) 322.1235, found 322.1239.

A solution of (E)-4-cyclopentyl-2-(4-methanesulfonyl-phenyl)-but-2-enoic acid methyl ester (1.00 g, 3.1 mmol) in ethanol (17 mL) was treated with a 1N aqueous sodium hydroxide solution (7 mL). The solution was heated at 45–50° C. for 15 h, at which time, thin layer chromatography analysis of the mixture indicated the absence of starting material. The reaction mixture was then concentrated in vacuo to remove ethanol, and the residue was diluted with water (30 mL) and extracted with diethyl ether (1×50 mL) to remove any neutral impurities. The aqueous layer was acidified with a 1N aqueous hydrochloric acid solution. The resulting acid was extracted into ethyl acetate (2×30 mL). The combined organic layers were washed with a saturated aqueous sodium chloride solution (1×50 mL), dried over anhydrous magnesium sulfate, filtered, and concentrated in vacuo to afford (E)-4-cyclopentyl-2-(4-methanesulfonyl-phenyl)-but-2-enoic acid (0.95 g, 99%) as a white solid: mp 162–165° C.; EI-HRMS m/e calcd for $C_{16}H_{10}O_4S$ (M+H)$^+$ 309.1160, found 308.1158.

A solution of triphenylphosphine (672 mg, 2.56 mmol) in methylene chloride (7.5 mL) was cooled to 0° C. and then treated with N-bromosuccinimide (456 mg, 2.56 mmol). The reaction mixture was stirred at 0° C. for 30 min and then treated with a solution of (E)-4-cyclopentyl-2-(4-methanesulfonyl-phenyl)-but-2-enoic acid (545.5 mg, 1.47 mmol) in methylene chloride (4 mL). The clear solution was stirred for 10 min at 0° C. and then allowed to warm to 25° C. where it was stirred for 1 h. The reaction mixture was then treated with 2-aminothiazole (378 mg, 3.76 mmol), and the resulting suspension was stirred at 25° C. over the weekend. The reaction mixture was concentrated in vacuo to remove methylene chloride, and the residue was diluted with ethyl acetate (75 mL) and a 1N aqueous hydrochloric acid solution (100 mL). The two layers were separated, and the aqueous layer was extracted with ethyl acetate (1×50 mL). The combined organic extracts were successively washed with a saturated aqueous sodium bicarbonate solution (2×50 mL) and a saturated aqueous sodium chloride solution (1×100 mL), dried over anhydrous magnesium sulfate, filtered, and concentrated in vacuo. Biotage chromatography (FLASH 40M, Silica, 4/1 to 1/1 hexanes/ethyl acetate) afforded (E)-4-cyclopentyl-2-(4-methanesulfonyl-phenyl)-but-2-enoic acid thiazol-2-ylamide (200 mg, 35%) as a white solid: mp 173–176° C.; EI-HRMS m/e calcd for $C_{19}H_{22}N_2O_3S_2$ (M$^+$) 390.1071, found 390.1072.

Example 22

(E)-2-[4-Cyclopentyl-2-(4-methanesulfonyl-phenyl)-but-2-enoylamino]-thiazole-4-carboxylic acid methyl ester

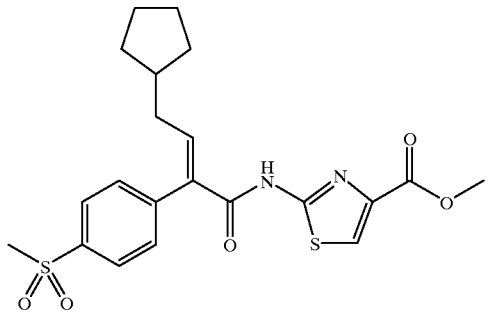

A solution of triphenylphosphine (525 mg, 2 mmol) in methylene chloride (25 mL) was cooled to 0° C. and then treated with N-bromosuecinimide (355 mg, 2 mmol). The reaction mixture was stirred at 0° C. for 30 min and then treated with (E)-4-cyclopentyl-2-(4-methanesulfonyl-phenyl)-but-2-enoic acid (prepared in Example 21, 308 mg, 1 mmol). The clear solution was stirred for 10 min at 0° C. and then allowed to warm to 25° C. where it was stirred for 1 h. The reaction mixture was then treated with 2-aminothiazole-4-carboxylic acid methyl ester (400 mg, 2.52 mmol), and the resulting suspension was stirred at 25° C. over the weekend. The reaction mixture was concentrated in vacuo to remove methylene chloride, and the residue was diluted with ethyl acetate (50 mL) and a 1N aqueous hydrochloric acid solution (50 mL). The two layers were separated, and the aqueous layer was extracted with ethyl acetate (1×25 mL). The combined organic extracts were successively washed with a saturated aqueous sodium bicarbonate solution (2×50 mL) and a saturated aqueous sodium chloride solution (1×100 mL), dried over anhydrous magnesium sulfate, filtered, and concentrated in vacuo. Biotage chromatography (FLASH 40M, Silica, 3/1 to 1/1 hexanes/ethyl acetate) afforded (E)-2-[4-cyclopentyl-2-(4-methanesulfonyl-phenyl)-but-2-enoylamino]-thiazole-4-carboxylic acid methyl ester (250 mg, 56%) as a white solid: mp 85–90° C.; EI-HRMS m/e calcd for $C_{21}H_{24}N_2O_5S_2$ (M$^+$) 448.1127, found 448.1117.

Example 23

(E)-2-[4-Cyclopentyl-2-(4-methanesulfonyl-phenyl)-but-2-enoylamino]-thiazole-5-carboxylic acid ethyl ester

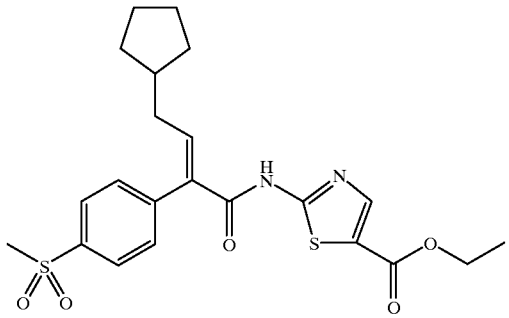

A solution of triphenylphosphine (787 mg, 3 mmol) in methylene chloride (40 mL) was cooled to 0° C. and then treated with N-bromosuccinimide (534 mg, 3 mmol). The reaction mixture was stirred at 0° C. for 30 min and then treated with (E)-4-cyclopentyl-2-(4-methanesulfonyl-phenyl)-but-2-enoic acid (prepared in Example 21, 462 mg, 1.5 mmol). The clear solution was stirred for 10 min at 0° C. and then allowed to warm to 25° C. where it was stirred for 1 h. The reaction mixture was then treated with 2-aminothiazole-5-carboxylic acid ethyl ester (774 mg, 4.5 mmol), and the resulting suspension was stirred at 25° C. over the weekend. The reaction mixture was concentrated in vacuo to remove methylene chloride, and the residue was diluted with ethyl acetate (70 mL) and a 1N aqueous hydrochloric acid solution (70 mL). The two layers were separated, and the aqueous layer was extracted with ethyl acetate (1×50 mL). The combined organic extracts were successively washed with a saturated aqueous sodium bicarbonate solution (1×100 mL) and a saturated aqueous sodium chloride solution (1×100 mL), dried over anhydrous magnesium sulfate, filtered, and concentrated in vacuo. Biotage chromatography (FLASH 40M, Silica, 3/1 to 1/1 hexanes/ethyl acetate) afforded (E)-2-[4-Cyclopentyl-2-(4-methanesulfonyl-phenyl)-but-2-enoylamino]-thiazole-5-carboxylic acid ethyl ester (250 mg, 36%) as an amorphous white solid: ET-HRMS m/e calcd for $C_{22}H_{26}N_2O_5S_2$ (M$^+$) 462.1283, found 462.1282.

Example 24

(E)-4-Cyclopentyl-2-(3,4-difluoro-phenyl)-but-2-enoic acid thiazol-2-ylamide

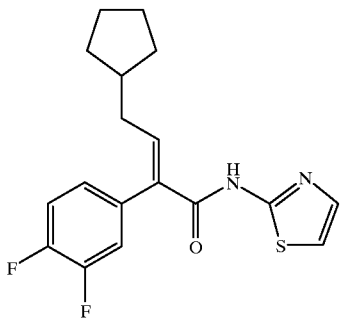

A mixture of zinc dust (0.98 g, 15 mmol, Aldrich, −325 mesh) and dry tetrahydrofuran (3 mL) under argon was treated with 1,2-dibromoethane (0.14 g, 0.75 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (82 mg, 0.75 mmol), and the suspension was stirred for 15 min at 25° C. The reaction mixture was then treated dropwise with a solution of (E)-4-cyclopentyl-2-iodo-but-2-enoic acid methyl ester (prepared in Example 21, 1.47 g, 5 mmol) in dry tetrahydrofuran (1.5 mL) over 3 min. After the addition, the reaction mixture was stirred for 1 h at 40–45° C. and then stirred overnight at 25° C. The reaction mixture was then diluted with dry tetrahydrofuran (5 mL), and the stirring was stopped to allow the excess zinc dust to settle down (~2 h). In a separate reaction flask, bis(dibenzylideneacetone) palladium(0) (54 mg, 0.1 mmol) and triphenylphosphine (104 mg, 0.4 mmol) in dry tetrahydrofuran (10 mL) was stirred at 25° C. under argon for 10 min and then treated with 3,4-difluoro-iodobenzene (0.96 g, 4 mmol) and the freshly prepared zinc compound in tetrahydrofuran. The resulting brick red solution was heated at 25° C. for 15 h, at which time, thin layer chromatography analysis of the reaction mixture indicated the absence of starting material. The reaction mixture was cooled to 25° C. and then poured into a saturated aqueous ammonium chloride solution (50 mL), and the organic compound was extracted into diethyl ether (2×50 mL). The combined ether extracts were washed with a saturated aqueous sodium chloride solution (1×50 mL), dried over anhydrous magnesium sulfate, filtered, and concentrated in vacuo. Biotage chromatography (FLASH 40M, Silica, 4/1 hexanes/diethyl ether) afforded (E)-4-cyclopentyl-2-(3,4-difluoro-phenyl)-but-2-enoic acid methyl ester (0.82 g, 73%) as a viscous oil: EI-HRMS m/e calcd for $C_{16}H_{18}F_2O_2$ (M+) 280.1275, found 280.1275.

A solution of (E)-4-cyclopentyl-2-(3,4-difluoro-phenyl)-but-2-enoic acid methyl ester (0.80 g, 2.85 mmol) in ethanol (14 mL) was treated with a 1N aqueous sodium hydroxide solution (6 mL). The solution was heated at 40° C. for 15 h, at which time, thin layer chromatography analysis of the mixture indicated the absence of starting material. The reaction mixture was then concentrated in vacuo to remove ethanol, and the residue was diluted with water (30 mL) and extracted with diethyl ether (1×50 mL) to remove any neutral impurities. The aqueous layer was acidified with a 1N aqueous hydrochloric acid solution. The resulting acid was extracted into ethyl acetate (2×50 mL). The combined organic layers were washed with a saturated aqueous sodium chloride solution (1×80 mL), dried over anhydrous magnesium sulfate, filtered, and concentrated in vacuo to afford (E)-4-cyclopentyl-2-(3,4-difluoro-phenyl)-but-2-enoic acid (0.65 g, 86%) as a colorless oil: EI-HRMS m/e calcd for $C_{15}H_{16}F_2O_2$ (M+H)+ 267.1196, found 267.1195.

A solution of triphenylphosphine (1.05 g, 4 mmol) in methylene chloride (15 mL) was cooled to 0° C. and then treated with N-bromosuccinimide (712 mg, 4 mmol). The reaction mixture was stirred at 0° C. for 30 min and then treated with a solution of (E)-4-cyclopentyl-2-(3,4-difluoro-phenyl)-but-2-enoic acid (0.63 g, 2.36 mmol) in methylene chloride (4 mL). The clear solution was stirred for 15 min at 0° C. and then allowed to warm to 25° C. where it was stirred for 1.5 h. The reaction mixture was then treated with 2-aminothiazole (0.59 g, 5.9 mmol), and the resulting suspension was stirred at 25° C. over the weekend. The reaction mixture was concentrated in vacuo to remove methylene chloride, and the residue was diluted with ethyl acetate (100 mL) and a 1N aqueous hydrochloric acid solution (100 mL). The two layers were separated, and the aqueous layer was extracted with ethyl acetate (1×50 mL). The combined organic extracts were successively washed with a saturated aqueous sodium bicarbonate solution (2×50 mL) and a saturated aqueous sodium chloride solution (1×100 mL), dried over anhydrous magnesium sulfate, filtered, and concentrated in vacuo. Biotage chromatography (FLASH 40M, Silica, 8/1 hexanes/ethyl acetate) afforded (E)-4-cyclopentyl-2-(3,4-difluoro-phenyl)-but-2-enoic acid thiazol-2-ylamide (435 mg, 53%) as an amorphous solid: EI-HRMS m/e calcd for $C_{18}H_{18}F_2N_2OS$ (M+) 348.1108, found 348.1103.

Example 25

(E)-4-Cyclopentyl-2-(4-methanesulfonyl-3-trifluoromethyl-phenyl)-but-2-enoic acid thiazol-2-ylamide

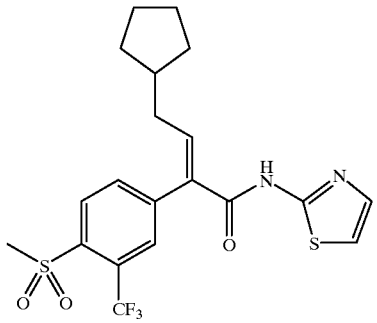

A mixture of zinc dust (0.65 g, 10 mmol, Aldrich, −325 mesh) and dry tetrahydrofuran (2 mL) under argon was treated with 1,2-dibromoethane (140 mg, 0.75 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (82 mg, 0.75 mmol), and the suspension was stirred for 15 min at 25° C. The reaction mixture was then treated dropwise with a solution of (E)-4-cyclopentyl-2-iodo-but-2-enoic acid methyl ester (prepared in Example 21, 1.03 g, 3.5 mmol) in dry tetrahydrofuran (1.5 mL) over 3 min. After the addition, the reaction mixture was stirred for 1 h at 40–45° C. and then stirred overnight at 25° C. The reaction mixture was then diluted with dry tetrahydrofuran (3 mL), and the stirring was stopped to allow the excess zinc dust to settle down (~2 h). In a separate reaction flask, bis(dibenzylideneacetone) palladium(0) (54 mg, 0.1 mmol) and triphenylphosphine (104 mg, 0.4 mmol) in dry tetrahydrofuran (10 mL) was stirred at 25° C. under argon for 10 min and then treated with 4-bromo-1-methanesulfonyl-2-trifluoromethyl-benzene (prepared in Example 12, 0.76 g, 2.5 mmol) and the freshly prepared zinc compound in tetrahydrofuran. The resulting brick red solution was heated at 25° C. for 15 h. The reaction mixture was then poured into a saturated aqueous ammonium chloride solution (50 mL), and the organic compound was extracted into ethyl acetate (2×50 mL). The combined organic extracts were washed with a saturated aqueous sodium chloride solution (1×50 mL), dried over anhydrous magnesium sulfate, filtered, and concentrated in vacuo. Biotage chromatography (FLASH 40M, Silica, 2/1 hexanes/ethyl acetate) afforded (E)-4-cyclopentyl-2-(4-(methanesulfonyl)-3-(trifluoromethyl)-phenyl)-but-2-enoic acid methyl ester (0.85 g, 87%) as a viscous oil: EI-HRMS m/e calcd for $C_{18}H_{21}F_3O_4S$ ($M^+$) 390.1113, found 390.1113.

A solution of (E)-4-cyclopentyl-2-[4-(methanesulfonyl)-3-(trifluoromethyl)-phenyl)-but-2-enoic acid methyl ester (0.82 g, 2.1 mmol) in ethanol (10 mL) was treated with a 1N aqueous sodium hydroxide solution (5 mL). The solution was heated at 40° C. for 15 h, at which time, thin layer chromatography analysis of the mixture indicated the absence of starting material. The reaction mixture was then concentrated in vacuo to remove ethanol, and the residue was diluted with water (30 mL) and extracted with diethyl ether (1×50 mL) to remove any neutral impurities. The aqueous layer was acidified with a 1N aqueous hydrochloric acid solution. The resulting acid was extracted into ethyl acetate (2× 50 mL). The combined organic layers were washed with a saturated aqueous sodium chloride solution (1×80 mL), dried over anhydrous magnesium sulfate, filtered, and concentrated in vacuo to afford (E)-4-cyclopentyl-2-[4-(methanesulfonyl)-3-(trifluoromethyl)-phenyl)-but-2-enoic acid (0.73 g, 92%) as a gummy solid: EI-HRMS m/e calcd for $C_{17}H_{19}F_3O_4S$ ($M^+$) 376.0243, found 376.0261.

A solution of triphenylphosphine (550 mg, 2.1 mmol) in methylene chloride (25 mL) was cooled to 0° C. and then treated with N-bromosuccinimide (374 mg, 2.1 mmol). The reaction mixture was stirred at 0° C. for 30 min and then treated with a solution of (E)-4-cyclopentyl-2-[4-(methanesulfonyl)-3-(trifluoromethyl)-phenyl)-but-2-enoic acid (395 mg, 1.05 mmol) in methylene chloride (5 mL). The clear solution was stirred for 15 min at 0° C. and then allowed to warm to 25° C. where it was stirred for 1.5 h. The reaction mixture was then treated with 2-aminothiazole (320 mg, 3.2 mmol), and the resulting suspension was stirred at 25° C. over the weekend. The reaction mixture was concentrated in vacuo to remove methylene chloride, and the residue was diluted with ethyl acetate (50 mL) and a 1N aqueous hydrochloric acid solution (50 mL). The two layers were separated, and the aqueous layer was extracted with ethyl acetate (1×30 mL). The combined organic extracts were successively washed with a saturated aqueous sodium bicarbonate solution (2×50 mL) and a saturated aqueous sodium chloride solution (1×100 mL). The organic layer was then dried over anhydrous magnesium sulfate, filtered, and concentrated in vacuo. Biotage chromatography (FLASH 40M, Silica, 1/1 hexanes/ethyl acetate) afforded the (E)-4-cyclopentyl-2-(4-methanesulfonyl-3-trifluoromethyl-phenyl)-but-2-enoic acid thiazol-2-ylamide (77 mg, 16%) as an amorphous solid: EI-HRMS m/e calcd for $C_{20}H_{21}F_3N_2O_3S_2$ ($M^+$) 458.0946, found 458.0946.

Example 26

(E)-1-[2-(3,4-Dichloro-phenyl)-4-methyl-pent-2-enoyl]-3-methyl-urea

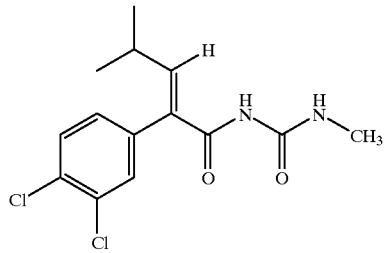

A mixture of aluminum chloride (16.81 g, 126.05 mmol) in methylene chloride (105 mL) was cooled to 5° C. and stirred until the solid material dissolved. The reaction mixture was then slowly treated with methyl oxalyl chloride (8.1 mL, 88.24 mmol), and the resulting reaction mixture was stirred at 5° C. for 30 min. The reaction mixture was then slowly treated with 1,2-dichlorobenzene (12.35 g, 84.04 mmol). The resulting reaction mixture was allowed to warm to 25° C. where it was stirred for 6 h. The reaction mixture was then stored at 0° C. for 15 h. The reaction mixture was slowly poured into ice/water (400 mL). The layers were shaken and separated. The aqueous layer was further extracted with methylene chloride (1×200 mL). The combined organic layers were washed with a saturated aqueous sodium bicarbonate solution (1×200 mL) and water (1×100 mL), dried over magnesium sulfate, filtered, and concentrated in vacuo. Flash chromatography (Merck Silica gel 60, 230–400 mesh, 9/1 hexanes/ethyl acetate) afforded (3,4-dichloro-phenyl)-oxo-acetic acid methyl ester (0.78 g, 4%) as a yellow solid: mp 58.2–63° C.; EI-HRMS m/e calcd for $C_9H_6Cl_2O_3$ ($M^+$) 231.9694, found 231.9699.

A suspension of isobutyl triphenylphosphonium bromide (2.02 g, 4.96 mmol) in dry tetrahydrofuran (5.4 mL) was cooled to 0° C. and then treated dropwise with a 1.0M solution of sodium bis(trimethylsilyl)amide (5 mL, 4.96 mmol). The bright orange reaction mixture was stirred at 0° C. for 1 h. The reaction mixture was then treated with a solution of (3,4-dichloro-phenyl)-oxo-acetic acid methyl ester (0.77 g, 3.30 mmol) in tetrahydrofuran (3 mL). The resulting reaction mixture was allowed to warm to 25° C. where it was stirred for 15 h. The reaction mixture was quenched with water (10 mL) and then concentrated in vacuo to remove tetrahydrofuran. The residue was further diluted with water (50 mL) and then extracted with ethyl acetate (2×75 mL). The combined organic layers were dried over sodium sulfate, filtered, and concentrated in vacuo. Flash chromatography (Merck Silica gel 60, 230–400 mesh, 97/3 hexanes/ethyl acetate) afforded the 2-(3,4-dichloro-phenyl)-4-methyl-pent-2-enoic acid methyl ester (749 mg, 83%) as a yellow viscous oil containing a 3.5:1 mixture of (E):(Z) isomers. The isomeric mixture was used without further separation and characterization.

The isomeric mixture of 2-(3,4-dichloro-phenyl)-4-methyl-pent-2-enoic acid methyl ester [749.0 mg, 2.74 mmol, (E):(Z)=3.5:1] and methyl urea (812.6 mg, 10.97 mmol) were treated with a solution of magnesium methoxide in methanol (7.4 wt %, 16 mL, 10.97 mmol). The resulting reaction mixture was heated under reflux for 15 h. The reaction mixture was allowed to cool to 25° C. and then filtered through celite. The celite was thoroughly washed with ethyl acetate. The filtrate was concentrated in vacuo. Flash chromatography (Merck Silica gel 60, 230–400 mesh, 9/1 hexanes/ethyl acetate) afforded impure 1-[2-(3,4-dichloro-phenyl)-4-methyl-pent-2-enoyl]-3-methyl-urea (280.2 mg) as a white solid. A second flash chromatography (Merck Silica gel 60, 230–400 mesh, 3/2 hexanes/diethyl ether) again afforded impure 1-[2-(3,4-dichloro-phenyl)-4-methyl-pent-2-enoyl]-3-methyl-urea (114.6 mg) as a white solid. Recrystallization from hexanes/ethyl acetate afford pure (E)-1-[2-(3,4-dichloro-phenyl)-4-methyl-pent-2-enoyl]-3-methyl-urea (24.7 mg, 3%) as a white solid: mp 177–178° C.; FAB-HRMS m/e calcd for $C_{14}H_{16}Cl_2N_2O_2$ (M+H)$^+$315.0667, found 315.0652.

Example 27

(E)-1-[3-Cyclohexyl-2-(4-methanesulfonyl-3-trifluoromethyl-phenyl)-acryloyl]-3-methyl-urea

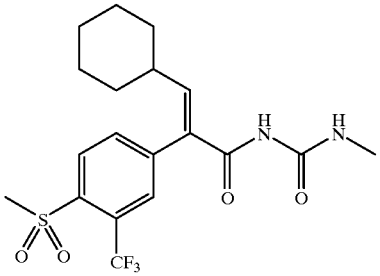

A solution of isoamyl nitrite (4.02 mL, 30 mmol) in dimethyl disulfide (19.8 mL, 220 mmol) at 25° C. was slowly treated with 4-bromo-2-(trifluoromethyl)aniline (4.8 g, 20 mmol). The reaction was exothermic with gas evolution. The resulting brown reaction mixture was heated to 80–90° C. for 2 h, at which time, thin layer chromatography analysis of the reaction mixture indicated the absence of starting material. The reaction mixture was cooled to 25° C. and then concentrated in vacuo. The resulting residue was dissolved in ethyl acetate (200 mL). The organic layer was washed successively with a 1 N aqueous hydrochloric acid solution (1×200 mL) and a saturated aqueous sodium chloride solution (1×200 mL), dried over anhydrous magnesium sulfate, filtered, and concentrated in vacuo. Biotage chromatography (FLASH 40M, Silica, 8/1 hexanes/ethyl acetate) afforded 4-bromo-1-methylsulfanyl-2-trifluoromethyl-benzene (4.73 g, 87%) as a brown oil: EI-HRMS m/e calcd for $C_8H_6BrF_3S$ (M$^+$) 269.9326, found 269.9327.

A solution of 4-bromo-1-methylsulfanyl-2-trifluoromethyl-benzene (4.71 g, 17.4 mmol) in methylene chloride (100 mL) was cooled to -10° C. and then treated with 3-chloroperoxybenzoic acid (86% grade, 9.0 g, 52.2 mmol). The reaction mixture was stirred at -10° C. for 10 min and then allowed to warm to 25° C. where it was stirred overnight. At this time, thin layer chromatography analysis of the reaction mixture indicated the absence of starting material. The reaction mixture was then filtered, and the solids were washed with methylene chloride (1×50 mL). The filtrate was concentrated in vacuo. The resulting residue was dissolved in ethyl acetate (100 mL). The organic layer was washed successively with a saturated aqueous sodium bicarbonate solution (2×100 mL) and a saturated aqueous sodium chloride solution (1×100 mL), dried over anhydrous magnesium sulfate, filtered, and concentrated in vacuo to afford a yellow solid. Recrystallization from methylene chloride (20 mL), diethyl ether (10 mL), and hexanes afforded 4-bromo-1-methanesulfonyl-2-trifluoromethyl-benzene (3.46 g, 57%) as a white solid: mp 110–112° C.; EI-HRMS m/e calcd for $C_8H_6BrF_3O_2S$ (M$^+$) 301,9224, found 301.9223.

A mixture of zinc dust (16.34 g, 250 mmol, Aldrich, -325 mesh) and dry tetrahydrofuran (6 mL) under argon was treated with 1,2-dibromoethane (0.94 g, 5 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (0.54 g, 5 mmol), and the suspension was stirred for 15 min at 25° C. The reaction mixture was then treated dropwise with a solution of cyclohexyl iodide (21 g, 100 mmol) in dry tetrahydrofuran (30 mL) over 15 min. During the addition, the temperature rose to 60° C. The reaction mixture was then stirred for 3 h at 40–45° C. The reaction mixture was then cooled to 25° C. and diluted with dry tetrahydrofuran (60 mL). The stirring was stopped to allow the excess zinc dust to settle down (~3 h). In a separate reaction flask, a mixture of lithium chloride (8.48 g, 200 mmol, predried at 130° C. under high vacuum for 3 h) and copper cyanide (8.95 g, 100 mmol) in dry tetrahydrofuran (110 mL) was stirred for 10 min at 25° C. to obtain a clear solution. The reaction mixture was cooled to -70° C. and then slowly treated with the freshly prepared zinc solution using a syringe. After the addition, the reaction mixture was allowed to warm to 0° C. where it was stirred for 5 min. The reaction mixture was again cooled back to -70° C. and then slowly treated with methyl propiolate (7.56 g, 90 mmol). The resulting reaction mixture was stirred for 15 h at -70° C. to -50° C. and then slowly treated with a solution of iodine (34.26 g, 135 mmol) in dry tetrahydrofuran (30 mL), with the temperature kept at -70° C. to -60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (400 mL) and ammonium hydroxide (100 mL), and the organic compound was extracted into ethyl acetate (3×250 mL). The combined organic extracts were successively washed with a saturated aqueous sodium thiosulfate solution (1×500 mL) and a saturated aqueous sodium chloride solution (1×500 mL), dried over anhydrous magnesium sulfate, filtered, and concentrated in vacuo. Flash chromatography (Merck Silica gel 60, 230–400 mesh, 9/1 hexanes/diethyl ether) afforded (E)-3-cyclohexyl-2-iodo-acrylic acid methyl ester (26.3 g, 99%) as a light pink oil: EI-IIRMS m/e calcd for $C^{10}H_{15}IO_2$ (M$^+$) 294.0117, found 294.0114.

A mixture of zinc dust (1.3 g, 20 mmol, Aldrich, -325 mesh) and dry tetrahydrofuran (2 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (110 mg, 1 mmol), and the suspension was stirred for 15 min at 25° C. The reaction mixture was then treated dropwise with a solution of (E)-3-cyclohexyl-2-iodo-acrylic acid methyl ester (2.5 g, 8.5 mmol) in dry tetrahydrofuran (3 mL) over 5 min. After the addition, the reaction mixture was stirred for 1 h at 40–45° C. and then stirred overnight at 25° C. The reaction mixture was then diluted with dry tetrahydrofuran (4 mL), and the stirring was stopped to allow the excess zinc dust to settle down (~2 h). In a separate reaction flask, bis(dibenzylideneacetone) palladium(0) (108 mg, 0.2 mmol) and triphenylphosphine (209 mg, 0.8 mmol) in dry tetrahydrofuran (10 mL) was stirred at 25° C. under argon for 10 min and then treated with 4-bromo-1-methanesulfonyl-2-trifluoromethyl-benzene (2.12 g, 7 mmol) and the freshly prepared zinc compound in tetrahydrofuran. The resulting brick red solution was heated at 40–45° C. for 2 d. The reaction mixture was cooled to 25° C. and then poured into a saturated aqueous ammonium chloride solution (100 mL), and the organic compound was extracted into ethyl acetate (3×75 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 9/1 to 3/1 hexanes/ethyl acetate) afforded (E)-3-cyclohexyl-2-(4-methanesulfonyl-3-trifluoromethyl-phenyl)-acrylic acid methyl ester (2.7 g, 99%) as a viscous oil: EI-HRMS m/e calcd for $C_{18}H_{21}F_3O_4S$ (M+) 391.1191, found 391.1200.

A solution of (E)-3-cyclohexyl-2-(4-methanesulfonyl-3-trifluoromethyl-phenyl)-acrylic acid methyl ester (1.8 g, 4.6 mmol) in ethanol (20 mL) was treated with a 1N aqueous sodium hydroxide solution (15 mL). The solution was heated at 45–50° C. for 15 h, at which time, thin layer chromatography analysis of the mixture indicated the absence of starting material. The reaction mixture was then concentrated in vacuo to remove ethanol, and the residue was diluted with water (40 mL) and extracted with diethyl ether (1×50 mL) to remove any neutral impurities. The aqueous layer was acidified with a 1N aqueous hydrochloric acid solution. The resulting acid was extracted into ethyl acetate (2×75 mL). The combined organic layers were washed with a saturated aqueous sodium chloride solution (1×100 mL), dried over anhydrous magnesium sulfate, filtered, and concentrated in vacuo to afford (E)-3-cyclohexyl-2-(4-(methanesulfonyl)-3-(trifluoromethyl)-phenyl)-acrylic acid (1.74 g, 99%) as a white solid: mp 62–64° C.; EI-HRMS m/e calcd for $C_{17}H_{19}F_3O_4S$ (M+H)+ 377.1034, found 377.1041.

A solution of (E)-3-cyclohexyl-2-(4-(methanesulfonyl)-3-(trifluoromethyl)-phenyl)-acrylic acid (282 mg, 0.75 mmol) in fluorobenzene (1 mL) and N,N-dimethylformamide (3 μL) at 25° C. was treated dropwise with oxalyl chloride (81 μL, 0.9 mmol) over 2–3 min. The clear solution was stirred at 25° C. for 1 h and then treated with methyl urea (167 mg, 2.25 mmol). The resulting suspension was heated at 70° C. (bath temperature) for 10 min and then treated with pyridine (121 μL, 1.5 mmol). The reaction mixture was then stirred at 70° C. for 20 h. The reaction mixture was then cooled to 25° C. and diluted with ethyl acetate (50 mL) and a 3N aqueous hydrochloric acid solution (40 mL). The two layers were separated, and the aqueous layer was extracted with ethyl acetate (1×20 mL). The combined organic extracts were successively washed with a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40M, Silica, 4/1 hexanes/ethyl acetate) afforded the (E)-1-[3-cyclohexyl-2-(4-methanesulfonyl-3-trifluoromethyl-phenyl)-acryloyl]-3-methyl-urea (104 mg, 32%) as a white solid: mp 199–202° C. EI-HRMS m/e calcd for $C_{19}H_{23}F_3N_2O_4S$ (M+) 432.1331, found 432.1332.

What is claimed is:

1. Compound selected from the group consisting of an olefinic amide of the formula:

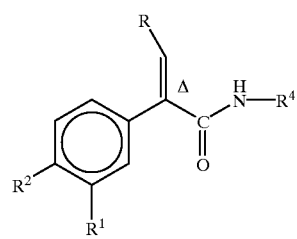

I wherein $R^1$ and $R^2$ are independently hydrogen, halo, amino, nitro, perfluoro-lower alkyl, lower alkyl thio, perfluoro-lower alkyl thio, lower alkyl sulfonyl, lower alkyl sulfonyl methyl, perfluoro-lower alkyl sulfonyl, or lower alkyl sulfinyl;

R is $—(CH_2)_m—R_3$ or lower alkyl containing from 2 to 4 carbon atoms;

$R^3$ is cycloalkyl having from 3 to 8 carbon atoms;

$R^4$ is

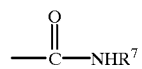

or an unsubstituted or a mono-substituted five- or six-membered heteroaromatic ring connected by a ring carbon atom to the amine group shown, which five- or six-membered heteroaromatic ring contains from 1 to 2 heteroatoms selected from the group consisting of sulfur, or nitrogen, with one heteroatom being nitrogen which is adjacent to the connecting ring carbon atom; said mono-substituted heteroaromatic ring being mono-substituted at a position on a ring carbon atom other than adjacent to said connecting carbon atom with a substituent selected from the group consisting of halo or

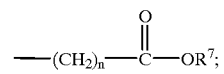

m is 0 or 1;
n is 0, 1, 2, 3 or 4;
$R^7$ is hydrogen or lower alkyl; and
Δ denotes a trans configuration across the double bond;
or a pharmaceutically acceptable salt thereof.

2. The compound of claim 1 wherein said amide has the formula:

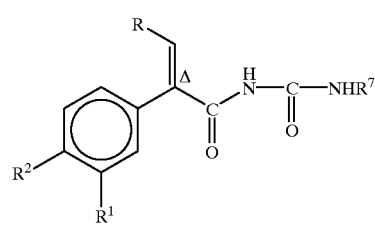

I-A wherein Δ, R, $R^1$ and $R^2$ and $R^7$ are as above.

3. The compound of claim 2 wherein R is cycloalkyl having from 3 to 8 carbon atoms.

4. The compound of claim 3 wherein R is cyclohexyl.

5. The compound of claim 4 wherein one of $R^1$ and $R^2$ is hydrogen, halo, lower alkyl sulfonyl or perfluoro lower alkyl and the other is halo, lower alkyl sulfonyl, or perfluoro lower alkyl.

6. The compound of claim 5 wherein one of $R^1$ and $R^2$ is hydrogen, lower alkyl sulfonyl or perfluoro lower alkyl and the other is lower alkyl sulfonyl or perfluoro lower alkyl.

7. The compound of claim 6 wherein said compound is (E)-1-[3-cyclohexyl-2-(4-methanesulfonyl-3-trifluoromethyl-phenyl)-acryloyl]-3-methyl-urea.

8. The compound of claim 2 wherein R is lower alkyl containing from 2 to 4 carbon atoms.

9. The compound of claim 8 wherein one of $R^1$ and $R^2$ is hydrogen, halo, lower alkyl sulfonyl or perfluoro lower alkyl and the other is halo, lower alkyl sulfonyl, or perfluoro lower alkyl.

10. The compound of claim 9 wherein said amide is (E)-1-[2-(3,4-dichloro-phenyl)-4-methyl-pent-2-enoyl]-3-methyl-urea.

11. The compound of claim 1 wherein said amide has the formula:

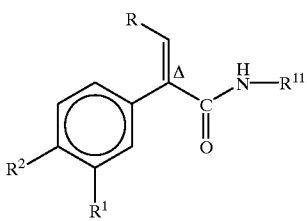

I-B wherein R, $R^2$, $R^1$ and Δ are as above; and $R^{11}$ is an unsubstituted or a mono-substituted five- or six-membered heteroaromatic ring connected by a ring carbon atom to the amine group shown, which five- or six-membered heteroaromatic ring contains from 1 to 2 heteroatoms selected from the group consisting of sulfur or nitrogen, with one heteroatom being nitrogen which is adjacent to the connecting ring carbon atom; said mono-substituted heteroaromatic ring being mono-substituted at a position on a ring carbon atom other than adjacent to said connecting carbon atom with a substituent selected from the group consisting of halo or

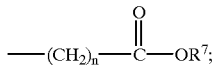

n is 0, 1, 2, 3 or 4;
$R^7$ is hydrogen or lower alkyl.

12. The compound of claim 11 wherein $R^{11}$ is an unsubstituted or monosubstituted thiazolyl ring.

13. The compound of claim 12 wherein said ring is an unsubstituted thiazolyl ring.

14. The compound of claim 13 wherein R is lower alkyl containing from 2 to 4 carbon atoms.

15. The compound of claim 14 wherein one of $R^1$ or $R^2$ is hydrogen, lower alkyl sulfonyl, lower alkyl sulfonyl methyl, perfluoro lower alkyl, halo, nitro and the other is lower alkyl sulfonyl, lower alkyl sulfonyl methyl, perfluoro lower alkyl, halo or nitro.

16. The compound of claim 15 wherein one of $R^1$ and $R^2$ is hydrogen or lower alkyl sulfonyl and the other is lower alkyl sulfonyl.

17. The compound of claim 16 wherein said amide is (E)-2-(4-methanesulfonyl-phenyl)-pent-2-enoic acid thiazol-2-ylamide.

18. The compound of claim 16 wherein said amide is (E)-2-(4-methanesulfonyl-phenyl)-4-methyl-pent-2-enoic acid thiazol-2-ylamide.

19. The compound of claim 12 wherein R is cycloalkyl having from 3 to 8 carbon atoms.

20. The compound of claim 19 wherein R is cyclopentyl.

21. The compound of claim 20 wherein said $R^1$ and $R^2$ is hydrogen, lower alkyl sulfonyl, lower alkyl sulfonyl methyl, perfluoro lower alkyl, halo or nitro and the other is lower alkyl sulfonyl, lower alkyl sulfonyl methyl, perfluoro lower alkyl, halo or nitro.

22. The compound of claim 21 wherein one of $R^1$ or $R^2$ is lower alkyl sulfonyl and the other is hydrogen or lower alkyl sulfonyl, halo or perfluoro lower alkyl.

23. The compound of claim 22 wherein said amide is (E)-3-cyclopentyl-2-(4-methanesulfonyl-phenyl)-N-thiazol-2-yl-acrylamide.

24. The compound of claim 22 wherein said amide is (E)-2-(3-chloro-4-methanesulfonyl-phenyl)-3-cyclopentyl-N-thiazol-2-yl-acrylamide.

25. The compound of claim 22 wherein said compound is (E)-2-(3-bromo-4-methanesulfonyl-phenyl)-3-cyclopentyl-N-thiazol-2-yl-acrylamide.

26. The compound of claim 21 wherein one of $R^1$ and $R^2$ is hydrogen, halogen, perfluoro lower alkyl and the other is halogen or perfluoro lower alkyl.

27. The compound of claim 26 wherein said amide is (E)-3-cyclopentyl-2-(3,4-dichloro-phenyl)-N-thiazol-2-yl-acrylamide.

28. The compound of claim 12 wherein $R^{11}$ is a mono-substituted thiazolyl ring.

29. The compound of claim 28 wherein R is cyclopentyl.

30. The compound of claim 29 wherein $R^{11}$ is a halo substituted thiazole ring.

31. The compound of claim 30 wherein one of $R^1$ and $R^2$ is lower alkyl sulfonyl, hydrogen or halo and the other is lower alkyl sulfonyl or halo.

32. The compound of claim 31 wherein said amide is (E)-N-(5-bromo-thiazol-2-yl)-3-cyclopentyl-2-(4-methanesulfonyl-phenyl)-acrylamide.

33. The compound of claim 13 wherein R is cyclohexyl.

34. The compound of claim 33 wherein one of $R^1$ or $R^2$ is hydrogen, lower alkyl sulfonyl, lower alkyl sulfonyl methyl, perfluoro lower alkyl, halo, nitro and the other is lower alkyl sulfonyl, lower alkyl sulfonyl methyl, perfluoro lower alkyl, halo or nitro.

35. The compound of claim 34 wherein one of $R^1$ or $R^2$ is lower alkyl sulfonyl and the other is hydrogen, nitro, lower alkyl sulfonyl, halo or perfluoro lower alkyl.

36. The compound of claim 34 wherein said amide is (E)-3-cyclohexyl-2-(4-methanesulfonyl-phenyl)-N-thiazol-2-yl-acrylamide.

37. The compound of claim 34 wherein said amide is (E)-3-cyclohexyl-2-(4-methanesulfonyl-3-nitro-phenyl)-N-thiazol-2-yl-acrylamide.

38. The compound of claim 34 wherein said amide is (E)-3-cyclohexyl-2-(4-methanesulfonyl-3-trifluoromethyl-phenyl)-N-thiazol-2-yl-acrylamide.

39. The compound of claim 34 wherein one of $R^1$ and $R^2$ is halo, hydrogen or perfluoro lower alkyl and the other is perfluoro lower alkyl or halogen.

40. The compound of claim 39 wherein said amide is (E)-3-cyclohexyl-2-(3,4-difluoro-phenyl)-N-thiazol-2-yl-acrylamide.

41. The compound of claim 34 wherein one of $R^1$ and $R^2$ is lower alkyl sulfonyl methyl and the other is hydrogen, lower alkyl sulfonyl methyl or halogen.

42. The compound of claim 41 wherein said amide is (E)-2-(3-chloro-4-methanesulfonylmethyl-phenyl)-3-cyclohexyl-N-thiazol-2-yl-acrylamide.

43. The compound of claim 12 wherein said thiazolyl ring is mono-substituted.

44. The compound of claim 43 wherein R is cycloheptyl.

45. The compound of claim 44 wherein said thiazolyl ring is substituted with halogen.

46. The compound of claim 45 wherein one or $R^1$ and $R^2$ is lower alkyl sulfonyl and the other is halogen, perfluoro lower alkyl or hydrogen.

47. The compound of claim 46 wherein said amide is (E)-N-(5-bromo-thiazol-2-yl)-3-cyclohexyl-2-(4-methanesulfonyl-3-trifluoromethyl-phenyl)-acrylamide.

48. The compound of claim 11, wherein R is cycloheptyl or cyclooctyl.

49. The compound of claim 48 wherein $R^{11}$ is mono-substituted or unsubstituted thiazolyl ring.

50. The compound of claim 49 wherein $R^{11}$ is an unsubstituted thiazolyl ring.

51. The compound of claim 50 wherein one of $R^1$ and $R^2$ is lower alkyl sulfonyl, hydrogen, halogen or perfluoro lower alkyl and the other is lower alkyl sulfonyl, halogen or perfluoro lower alkyl.

52. The compound of claim 51 wherein said amide is (E)-3-cycloheptyl-2-(4-methanesulfonyl-phenyl)-N-thiazol-2-yl-acrylamide.

53. The compound of claim 51 wherein said amide is (E)-3-cyclooctyl-2-(4-methanesulfonyl-phenyl)-N-thiazol-2-yl-acrylamide.

54. The compound of claim 51 wherein said amide is (E)-N-(5-bromo-thiazol-2-yl)-3-cycloheptyl-2-(4-methanesulfonyl-phenyl)-acrylamide.

55. The compound of claim 51 wherein said amide is (E)-3-cycloheptyl-2-(4-methanesulfonyl-3-trifluoromethyl-phenyl)-N-thiazol-2-yl-acrylamide.

56. The compound of claim 49 wherein $R^{11}$ is a mono-substituted thiazole ring.

57. The compound of claim 56 wherein said thiazole ring is halo substituted.

58. The compound of claim 57 wherein one of $R^1$ and $R^2$ is lower alkyl sulfonyl, hydrogen, halogen or perfluoro lower alkyl and the other is lower alkyl sulfonyl, halogen or perfluoro lower alkyl.

59. The compound of claim 58 wherein said amide is (E)-N-(5-bromo-thiazol-2-yl)-3-cycloheptyl-2-(4-methanesulfonyl-3-trifluoromethyl-phenyl)-acrylamide.

60. The compound of claim 11 wherein R is —$CH_2$—$R^3$.

61. The compound of claim 60 wherein $R^3$ is cyclopentyl.

62. The compound of claim 61 wherein $R^{11}$ is substituted or unsubstituted or a mono-substituted thiazolyl ring.

63. The compound of claim 62 wherein $R^{11}$ is an unsubstituted thiazolyl ring.

64. The compound of claim 63 wherein one of $R^1$ and $R^2$ is hydrogen, lower alkyl sulfonyl, perfluoro lower alkyl or halogen and the other is halogen, lower alkyl sulfonyl or perfluoro lower alkyl.

65. The compound of claim 64 wherein said amide is (E)-4-cyclopentyl-2-(4-methanesulfonyl-phenyl)-but-2-enoic acid thiazol-2-ylamide.

66. The compound of claim 64 wherein said amide is (E)-4-Cyclopentyl-2-(3,4-difluoro-phenyl)-but-2-enoic acid thiazol-2-ylamide.

67. The compound of claim 64, wherein said amide is (E)-4-Cyclopentyl-2-(4-methanesulfonyl-3-trifluoromethyl-phenyl)-but-2-enoic acid thiazol-2-ylamide.

68. The compound of claim 62 wherein said thiazolyl ring is mono-substituted with

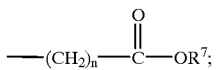

and n and $R^7$ are as above.

69. The compound of claim 68 wherein one of $R^1$ and $R^2$ is lower alkyl sulfonyl, and the other is lower alkyl sulfonyl or hydrogen.

70. The compound of claim 69 wherein said amide is (E)-2-[4-cyclopentyl-2-(4-methanesulfonyl-phenyl)-but-2-enoylamino]-thiazole-4-carboxylic acid methyl ester.

71. The compound of claim 69 wherein said amide is (E)-2-[4-cyclopentyl-2-(4-methanesulfonyl-phenyl)-but-2-enoylamino]-thiazole-5-carboxylic acid ethyl ester.

72. The compound of claim 11 wherein $R^{11}$ is an unsubstituted or mono-substituted pyridinyl ring.

73. The compound of claim 72, wherein said amide is (E)-N-(5-Bromo-pyridin-2-yl)-3-cyclohexyl-2-(4-methanesulfonyl-3-trifluoromethyl-phenyl)-acrylamide.

74. The compound of claim 72 wherein one of $R^1$ and $R^2$ is lower alkyl sulfonyl or halogen and the other is hydrogen, lower alkyl sulfonyl or halogen.

75. The compound of claim 74 wherein said amide is (E)-2-(3-Chloro-4-methanesulfonyl-phenyl)-3-cyclopentyl-N-pyridin-2-yl-acrylamide.

\* \* \* \* \*